US012183452B2

(12) United States Patent
Mathur et al.

(10) Patent No.: US 12,183,452 B2
(45) Date of Patent: Dec. 31, 2024

(54) ALGORITHM ORCHESTRATION OF WORKFLOWS TO FACILITATE HEALTHCARE IMAGING DIAGNOSTICS

(71) Applicant: GE Precision Healthcare LLC, Milwaukee, WI (US)

(72) Inventors: Garima Mathur, Princeton, NJ (US); Dean Whitney, Watertown, MA (US); Paulo Gallotti, San Ramon, CA (US); Chris Diviyanathan, San Ramon, CA (US); Vijay Arlagadda, Hoffman Estates, IL (US); Garrett Rogers, Channahon, IL (US); Flávio Henrique Schuindt da Silva, San Ramon, CA (US); Hrishikesh Nerurkar, San Ramon, CA (US); Eugene Martin Salvetti, Jr., Clayton, CA (US)

(73) Assignee: GE Precision Healthcare LLC, Waukesha, WI (US)

( * ) Notice: Subject to any disclaimer, the term of this patent is extended or adjusted under 35 U.S.C. 154(b) by 467 days.

(21) Appl. No.: 17/102,595

(22) Filed: Nov. 24, 2020

(65) Prior Publication Data
US 2021/0174941 A1 Jun. 10, 2021

Related U.S. Application Data

(60) Provisional application No. 62/939,910, filed on Nov. 25, 2019.

(51) Int. Cl.
*G16H 40/20* (2018.01)
*G06F 9/54* (2006.01)
(Continued)

(52) U.S. Cl.
CPC ............. *G16H 40/20* (2018.01); *G06F 9/541* (2013.01); *G06F 11/3664* (2013.01);
(Continued)

(58) Field of Classification Search
CPC ........ G16H 40/20; G16H 30/20; G16H 30/40; G16H 50/20; G16H 15/00; G06F 9/541;
(Continued)

(56) References Cited

U.S. PATENT DOCUMENTS 9,525,692 B2 * 12/2016 Gaudet .................. G06F 21/60
9,691,167 B1 6/2017 Frenkel et al.
(Continued)

FOREIGN PATENT DOCUMENTS

WO WO-2007002380 A2 * 1/2007 ........... G06T 11/206
WO 2019/157214 A2 8/2019
(Continued)

OTHER PUBLICATIONS

Seeram, et al., "Image Postprocessing in Digital Radiology—A Primer for Technologists," vol. 39, Issue 1, p. 23-41, Mar. 1, 2008.
(Continued)

*Primary Examiner* — Robert A Sorey
*Assistant Examiner* — Kimberly A. Sass
(74) *Attorney, Agent, or Firm* — Amin, Turocy & Watson, LLP

(57) ABSTRACT

Techniques for orchestrating execution of algorithms on medical images according to pre-defined workflows and techniques for managing workflow and model execution are provided. In an embodiment, a system comprises a memory that stores computer executable components and a processor that executes the computer executable components stored in the memory. The computer executable components comprise an algorithm catalog that comprises algorithm information identifying algorithms available for processing medical images, the algorithm information comprising algorithm execution instructions for executing the algorithms as web-services; and an onboarding component that adds the algorithm information to the algorithm catalog in response (Continued)

to reception of the algorithm information via an onboarding user interface of an algorithm management application, wherein based on inclusion of the algorithm information in the algorithm catalog, the algorithms are made available for incorporating into workflows for executing the algorithms on the medical images.

24 Claims, 70 Drawing Sheets

(51) Int. Cl.
*G06F 11/36* (2006.01)
*G06Q 10/067* (2023.01)
*G16H 30/20* (2018.01)
*G16H 30/40* (2018.01)
*G16H 50/20* (2018.01)
*H04L 9/40* (2022.01)
*G16H 15/00* (2018.01)

(52) U.S. Cl.
CPC ........... *G06Q 10/067* (2013.01); *G16H 30/20* (2018.01); *G16H 30/40* (2018.01); *G16H 50/20* (2018.01); *H04L 63/102* (2013.01); *G16H 15/00* (2018.01)

(58) Field of Classification Search
CPC ............... G06F 11/3664; G06F 11/079; G06F 11/3476; G06F 11/0751; G06F 11/0766; G06Q 10/067; H04L 63/102
See application file for complete search history.

(56) References Cited

U.S. PATENT DOCUMENTS

| | | |
|---|---|---|
| 2003/0212580 A1 | 11/2003 | Shen |
| 2010/0049740 A1 | 2/2010 | Iwase et al. |
| 2014/0180699 A1 | 6/2014 | Massa et al. |
| 2016/0350919 A1* | 12/2016 | Steigauf ................. G16H 40/20 |
| 2018/0060512 A1 | 3/2018 | Sorenson et al. |
| 2018/0137244 A1* | 5/2018 | Sorenson ............... G16H 30/20 |
| 2018/0322941 A1 | 11/2018 | Krishnan et al. |
| 2019/0090025 A1 | 3/2019 | Chesson |
| 2019/0180862 A1* | 6/2019 | Wisser ................... G16H 80/00 |
| 2019/0385099 A1 | 12/2019 | Vijayakar et al. |
| 2020/0202273 A1* | 6/2020 | Lehmann ......... G06Q 10/06316 |

FOREIGN PATENT DOCUMENTS

| | | | |
|---|---|---|---|
| WO | WO-2020048421 A1 * | 3/2020 | |
| WO | 2021/014181 A1 | 1/2021 | |

OTHER PUBLICATIONS

Non-Final Office Action for U.S. Appl. No. 17/122,003 dated Dec. 22, 2022, 35 pages.
International Search Report and Written Opinion for PCT/US2020/062208 dated Mar. 6, 2021, 13 pages.
Final Office Action for U.S. Appl. No. 17/122,003 dated Jul. 12, 2023, 50 pages.
Non-Final Office Action for U.S. Appl. No. 17/122,003 dated Sep. 25, 2023, 47 pages.
Notice of Allowance received for U.S. Appl. No. 17/122,003 dated Feb. 22, 2024, 129 pages.

* cited by examiner

FIG. 7

Algorithm Management

AI Orchestrator — Healthcare Edition

Tabs: Algorithms | Workflows | Task Registry | Devices | Activity Log | Dashboard 701 (page), 702 → Onboard Algorithm, 704 → Algorithm Editor

| Display Name | Last Updated ↓ | Algorithm | Provider | Version |
|---|---|---|---|---|
| MockModelPerfCT | Jul 16 2020 10:43:58 | MockModelPerfCT | Third Party | 1.0.0 |
| ptxmodel_ie | Jul 15 2020 16:16:41 | ptxmodel_ie | Internal | 1 |
| MockModelPerf | Jul 15 2020 16:04:57 | MockModelPerf | Third Party | 1.0.0 |
| MockModelPerfXray | Jul 15 2020 14:56:30 | MockModelPerfXray | Third Party | 1.0.0 |
| chestfrontal_ie | Jul 12 2020 16:14:44 | chestfrontal_ie | Internal | 1 |
| TestSth | Jul 09 2020 03:36:30 | TestSth | Third Party | 1.1 |
| qatest1 | Jul 08 2020 06:57:51 | qatest111 | Third Party | 1.1 |
| Mock | Jul 08 2020 03:53:09 | Mock | Third Party | 1.0.0 |
| Intracranial Hemorrhage | Jul 07 2020 08:52:09 | ICH_CT_Brain | Third Party | 1.6.14 |
| Test3rd | Jul 07 2020 02:58:20 | TestSth | Third Party | 1 |

Show [10 ▼] Entries  < Previous 1 2 Next >  Showing 1 – 10 of 12

Algorithms / Onboard Algorithm

Details

Provider: ○ Internal  ● Third Party

Thresholds

○ Algorithm Criticality  00

[Cancel] [Save]

Route*: Select Model Route ▼  ← 902

Name*: Enter Model Name

Version*: Enter Version

Display Name*: Enter Display Name

Input XSL*:
```
<?xml version="1.0" encoding="UTF-8"?>
<xsl:stylesheet xmlns:xsl="http://www.w3.org/1999/XSL/Transform" version="1.0">
  <xsl:output method="text"/>
  <xsl:template match="/">
  {
    "name": "<xsl:value-of select="/Operation/model/name"/>",
    "version": "<xsl:value-of select="/Operation/model/version"/>",
    "input":
```

Output XSL*:
```
<?xml version="1.0" encoding="ISO-8859-1"?>
<xsl:stylesheet version="1.0" xmlns:xsl="http://www.w3.org/1999/XSL/Transform">
  <xsl:output method="text"/>
  <xsl:template match="/">
  </xsl:template>
</xsl:stylesheet>
```

901

Workflow Management

AI Orchestrator — Healthcare Edition

Algorithms | Workflows | Task Registry | Devices | Activity Log | Dashboard

Search: *eg Workflow Name*

[Create New Workflow]

| Workflow Name | Last Updated ∨ | Type | Created by | Status | |
|---|---|---|---|---|---|
| Set2_154_Parent Workflow for Loop Worker - Test | Jul 17 2020 05:33:04 | Workflow | austin | ○ | ⚙ |
| Set2_154_Sub Workflow 1 PTX Model | Jul 17 2020 05:27:38 | Sub-Workflow | austin | | ⚙ |
| Set2_154_Sub Workflow 2 PTX Model | Jul 17 2020 05:23:01 | Sub-Workflow | austin | | ⚙ |
| Set1_154_Parent Workflow for Loop Worker | Jul 17 2020 05:16:01 | Workflow | edison | ○ | ⚙ |
| Set1_154_PTX Sub Workflow | Jul 17 2020 05:14:57 | Sub-Workflow | austin | | ⚙ |
| Set1_154_Sub Workflow 1 PTX Model | Jul 17 2020 05:01:00 | Sub-Workflow | edison | | ⚙ |
| Set1_154_Sub Workflow 2 PTX Model | Jul 17 2020 04:54:49 | Sub-Workflow | edison | | ⚙ |
| Set1_154_PTX Sub Workflow | Jul 17 2020 04:50:10 | Workflow | austin | ● | ⚙ |
| cmovement | Jul 17 2020 04:17:26 | Sub-Workflow | edison | | |
| PTX-Sub-Workflow-2 | Jul 17 2020 03:56:38 | | | | ⚙ |

Show [10 ∨] Entries    < Previous 1 2 3 4 5 6 ... 8 Next >    Showing 1 – 10 of 77

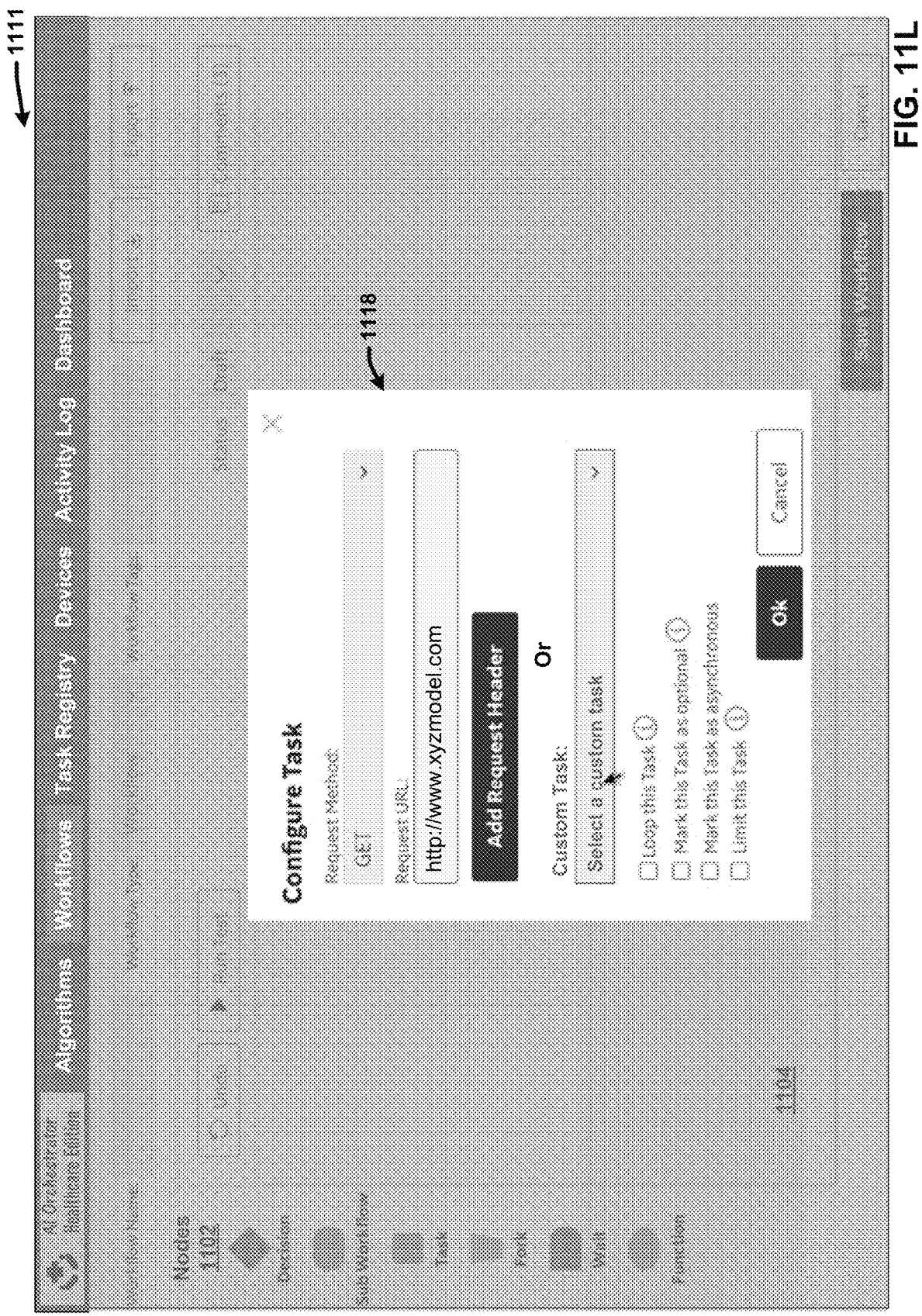

Task Registry

AI Orchestrator — Healthcare Edition

Algorithms | Workflows | Task Registry | Devices | Activity Log | Dashboard

[Create a Task Template]

| Name | Type | Last Updated ∨ | Created By | Description | Tags | |
|---|---|---|---|---|---|---|
| ASYNC HTTP Task 01 | AsyncHttp | Jul 15 2020 09:16:22 | denver | ASYNC HTTP Task 01 | Async Http Task 01 | 🗑 |
| TASK NO COLOR | SyncHttp | Jul 06 2020 16:11:56 | edison | TASK NO COLOR | | 🗑 |
| ASYNC HTTP Task 02 | AsyncHttp | Jul 06 2020 14:12:07 | edison | ASYNC HTTP Task 02 | ASYNC HTTP Task 02 | 🗑 |
| K8s-Job02 | Job | Jul 06 2020 14:11:16 | edison | K8s-Job02 | | 🗑 |
| K8s-Job01 | Job | Jul 06 2020 14:10:00 | edison | K8s-Job01 | k8s-Job01 | 🗑 |
| HTTP Task 01 | SyncHttp | Jul 06 2020 14:06:04 | edison | HTTP Task 01 | httpTaskTag01 | 🗑 |

Show [10 ∨] Entries  Showing 1 – 6 of 6

Task Registry

AI Orchestrator — Healthcare Edition

Algorithms | Workflows | Task Registry | Devices | Activity Log | Dashboard

✓ Task 'PTX Detection' created

| Name | Type | Last Updated ⌄ | Created By | Description | Tags | |
|---|---|---|---|---|---|---|
| PTX Detection | SyncHttp | Jul 17 2020 08:30:49 | edison | PTX Detection | | 🗑 |
| ASYNC HTTP Task 01 | AsyncHttp | Jul 15 2020 09:16:22 | denver | ASYNC HTTP Task 01 | Async Http Task 01 | 🗑 |
| TASK NO COLOR | SyncHttp | Jul 06 2020 16:11:56 | edison | TASK NO COLOR | | 🗑 |
| ASYNC HTTP Task 02 | AsyncHttp | Jul 06 2020 14:12:07 | edison | ASYNC HTTP Task 02 | ASYNC HTTP Task 02 | 🗑 |
| K8s-Job02 | Job | Jul 06 2020 14:11:16 | edison | K8s-Job02 | | 🗑 |
| K8s-Job01 | Job | Jul 06 2020 14:10:00 | edison | K8s-Job01 | k8s-Job01 | 🗑 |
| HTTP Task 01 | SyncHttp | Jul 06 2020 14:06:04 | edison | HTTP Task 01 | httpTaskTag01 | 🗑 |

Show [ 10 ⌄ ] Entries    Showing 1 – 6 of 6

FIG. 13D

Devices

← 1401

| Device name | Last updated ∨ | Type | Host | Port | |
|---|---|---|---|---|---|
| AutomationDevicesE8veemSRK111111111 | Jul 15 2020 00:45:00 | DICOM | 1.0.0.0 | 901 | 🗑 |
| sqat122 | Jul 14 2020 04:54:25 | DICOM | 1111 | 1 | 🗑 |
| poeroiaio iwtuwatoiwwatoiwrt aiyiuuiwruityat | Jul 08 2020 23:16:25 | DICOM | http://google.dooole. | 2000 | 🗑 |
| LOCAL_ORTHANC | Jul 05 2020 22:31:20 | DICOM | 127.0.0.1 | 4242 | 🗑 |
| E2E_TASK_WORKFLOW_DEVICE | Jun 24 2020 08:42:54 | DICOM | task | 1234 | 🗑 |
| ORTHANC_128 | Jun 18 2020 21:05:47 | DICOM | 10.84.115.128 | 4242 | 🗑 |
| CPACS | Jun 18 2020 15:28:12 | DICOM | 10.84.109.149 | 4100 | 🗑 |
| 1112333 | Jun 08 2020 02:31:56 | DICOM | 12334 | 11 | 🗑 |
| test678 | Jun 05 2020 05:44:51 | DICOM | 1234 | 1234 | 🗑 |
| test67 | Jun 05 2020 05:44:28 | DICOM | 1234 | 1321 | 🗑 |

Showing 1 – 10 of 13    Show [10 ∨] Entries    < Previous [1] 2 Next >

AI Orchestrator Healthcare Edition | Algorithms | Workflows | Task Registry | Devices | Activity Log | Dashboard ← 1511

Workflow name    Type    Status    1510 →    Start time    Duration    Version    ▲ Run Test PTX-Parent-Workflow-RISi    Workflow    FAILED    Jul 14 2020 16:48:24    00:03:11    4

Tasks

| Start time ∧ | Duration | Task ref name | Task type | Input data | Output data | Status |
|---|---|---|---|---|---|---|
| Jul 14 2020 16:48:24 | 00:00:00 | decision_140 | DECISION | View Input Data | View Output Data | Completed |
| Jul 14 2020 16:48:24 | 00:00:00 | task_1 | HTTP | View Input Data | View Output Data | Completed |
| Jul 14 2020 16:48:26 | 00:00:00 | loop_worker | loop_worker | View Input Data | View Output Data | Completed |
| Jul 14 2020 16:48:26 | 00:00:05 | forkedTask1 | SUB_WORKFLOW | View Input Data | View Output Data | Completed |
| Jul 14 2020 16:48:27 | 00:03:08 | forkedTask2 | SUB_WORKFLOW | View Input Data ← 1508 | View Output Data | Failed |
| Jul 14 2020 16:48:26 | 00:03:08 | join_sub_wf_23 | JOIN | View Input Data | View Output Data | Failed |

FIG. 15B

LOCAL DEVICE DEPLOYMENT

ALGORITHM ORCHESTRATION OF WORKFLOWS TO FACILITATE HEALTHCARE IMAGING DIAGNOSTICS

RELATED APPLICATION

This application claims priority to U.S. Provisional Application Ser. No. 62/939,910 filed Nov. 25, 2019 and titled "ALGORITHM ORCHESTRATION OF WORKFLOWS TO FACILITATE HEALTHCARE IMAGING DIAGNOSTICS," the entirety of which application is incorporated herein by reference.

TECHNICAL FIELD

This application relates to algorithm orchestration in the medical imaging domain, including techniques for orchestrating execution of algorithms on medical images according to pre-defined workflows and techniques for managing workflow and model execution.

BACKGROUND

The healthcare industry has innumerable opportunities to leverage artificial intelligence (AI), machine learning (ML), and other analytical models to achieve more accurate, proactive, and comprehensive patient care. From reducing administrative burdens to supporting precision medicine, these analytical tools are showing promise across clinical, financial, and operational domains. Learning algorithms, for instance, can become more precise and accurate as they interact with training data, allowing humans to gain unprecedented insights into diagnostics, care processes, treatment variability, and patient outcomes. However, even organizations with industry-leading analytics competencies in hand are facing complex challenges when it comes to applying various analytics to clinical care.

SUMMARY

The following presents a summary to provide a basic understanding of one or more examples of the invention. This summary is not intended to identify key or critical elements or delineate any scope of the different examples or any scope of the claims. Its sole purpose is to present concepts in a simplified form as a prelude to the more detailed description that is presented later. In one or more examples, systems, computer-implemented methods, apparatus and/or computer program products are described herein that facilitate integrating AI informatics into healthcare systems using a centralized orchestration component that orchestrates execution of AI algorithms on medical images according to pre-defined workflows. The disclosed subject matter further provides systems, computer-implemented methods, apparatus and/or computer program products that facilitate managing workflow and model execution by the algorithm orchestration component.

According to an example, a system is provided that includes a memory that stores computer executable components. The system includes a processor that executes the computer executable components stored in the memory. The computer executable components include an algorithm catalog that includes a plurality of diagnostic algorithms employed to analyze at least one medical image of a patient and metadata that describes attributes of the at least one medical image. An algorithm orchestration component executes workflow instructions that describe a computer executable diagnostic routine to be applied to the at least one medical image and the metadata. The algorithm orchestration component selects at least one diagnostic algorithm from the algorithm catalog to execute the diagnostic routine based on the at least one medical image and the metadata in response to the workflow instructions. A workflow execution engine executes the selected at least one diagnostic algorithm from the algorithm catalog in response to a command from the algorithm orchestration component.

The system can further comprise a notification component provides a notification output from the algorithm orchestration component in response to executing the diagnostic routine. The notification output can include at least one of a status output indicating progress of the diagnostic routine and metadata analysis of the metadata in response to the workflow instructions.

In some embodiments, the algorithm orchestration component performs the metadata analysis in response to the workflow instructions, the metadata analysis including at least one test to determine the status of the patient, a test to determine a status of the medical image, a test to determine available algorithms in the algorithm catalog, and a test to determine status of diagnostic thresholds of selected algorithms that have been applied to the medical image from the algorithm catalog. Test results can also be included in the notification output. In various embodiments, the analytical data is determined by at least one AI algorithm selected from the algorithm catalog and applied to the at least one medical image to diagnose the patient in response to the workflow instructions.

The system of can further comprise an algorithm management interface that includes threshold setting adjustments to enable diagnostic thresholds to be set that define whether or not a given medical condition is applicable to the patient based on execution of the at least one artificial intelligence algorithm. The system can further comprise an activity dashboard interface that displays at least one of an overview of potential medical conditions determined by the artificial intelligence algorithms, a number of studies that were employed to analyze the potential medical conditions, and a number of patients that were previously analyzed. In some implementation, the activity dashboard displays at least one of an artificial intelligence prediction of the medical diagnostic conditions versus a selected radiologist diagnosis of the medical diagnostic conditions, at least one other artificial intelligence prediction of the medical diagnostic conditions versus another selected radiologist diagnosis of the medical diagnostic conditions, and a confidence output showing false positive diagnostic rates versus true positive diagnostic rates.

The system can further comprise a workflow configuration tool to enable at least one of selection, configuration, and editing of the workflow instructions. In some embodiments, the workflow configuration tool further includes a simulator tool to enable testing of the workflow instructions based on a suite of test medical images and test metadata associated with the test medical images before downloading the workflow instructions to the algorithm orchestration component. The workflow configuration tool includes at least one template of initial workflow instructions to execute a given workflow, the at least one template including a start workflow instruction and an end workflow instruction that define the beginning and ending of the given workflow. The workflow instructions can include a fork instruction to define a parallel processing path of a given workflow and a join instruction to combine at least two parallel processing paths of the given workflow. The workflow instructions can also include at least one of a wait instruction to cause a given workflow to wait for an asynchronous task to be completed, a decision branch to cause a workflow decision based on a logical expression, and a Hyper Text Transfer (HTTP) task instruction to invoke an HTTP service to be initiated by a given workflow. The workflow instructions can also include a sub-workflow instruction that causes another workflow to be executed within a given set of workflow instructions.

The system can further comprise at least one security component that defines and executes security protocols to be employed by the algorithm orchestration component when exchanging files with other components. In various implementations, the algorithm orchestration component executes workflow instructions to process a plurality of medical images that are employed in a three-dimensional reconstruction of the patient from which the images were captured.

In another example embodiment, a system is provided that includes a memory that stores computer executable components. The system includes a processor that executes the computer executable components stored in the memory. The computer executable components include an algorithm orchestration component that receives a request to process a medical image using at least one medical image inferencing models, and an orchestration conductor component that identifies a workflow comprising a medical image inferencing model that is applicable to the medical image, wherein the medical image inferencing model is stored at a network accessible source. The computer executable components can further comprise a workflow execution engine that executes the workflow using the medical image, including accessing the medical image inferencing model at the network accessible source and applies the medical image inferencing model to the medical image, resulting in generation of a workflow outcome result. The algorithm orchestration component can further provide result information regarding the workflow outcome result to an entity associated with the request.

In another example embodiment, a system is provided that includes a memory that stores computer executable components. The system includes a processor that executes the computer executable components stored in the memory. The computer executable components include an algorithm catalog that comprises algorithm information identifying algorithms available for processing medical images, the algorithm information comprising algorithm execution instructions for executing the algorithms as web-services, and an onboarding component that adds the algorithm information to the algorithm catalog in response to reception of the algorithm information via an onboarding user interface of an algorithm management application, wherein based on inclusion of the algorithm information in the algorithm catalog, the algorithms are made available for incorporating into workflows for executing the algorithms on the medical images. In various implementations, the algorithms comprise medical image inferencing models. The algorithms can also comprise internal algorithms and third-party algorithms stored at different network accessible file locations.

The computer executable components can further comprise an algorithm orchestration component that receives image processing requests from medical imaging providers via a network, and a workflow execution component that executes the workflows on the medical images in association with reception of the image processing requests and returns workflow results to the medical imaging providers, the workflow results comprising outputs of one or more of the algorithms. The image processing are requests are received from devices associated with the medical imaging providers and the computer executable components can further comprise a security component that restricts acceptance of the imaging processing requests to registered devices included in device registry information.

The computer executable components can further comprise an algorithm execution engine that calls the algorithms at their network accessible file locations to receive the outputs in association with executing the workflows. The computer executable components can further comprise a translation component that translates an algorithm format from a first format that is not compatible with the algorithm execution engine to a second format that is compatible with the algorithm execution engine in association with the onboarding. For example, the second format can be compatible with an application program interface employed by the algorithm execution engine. In some implementations, the algorithm management application further provides for adjusting one or more parameters and thresholds of the algorithms in association with receiving the algorithm information.

The computer executable components can further comprise a workflow creation component that provides a workflow creation application for creating the workflows using the algorithms based on inclusion of the algorithm information in the algorithm catalog. A simulator component can also be provided that runs the workflows in a test mode on one or more test images and identifies execution errors.

The computer executable components can further comprise a workflow management component that provides, via the algorithm management application, access to workflow information defining the workflows and workflow management functions related to the workflows. In some implementation, the workflow management functions include an activation/deactivation function that provides for selectively activating and deactivating one or more of the workflows. The workflow management functions can also provide for editing workflows, deleting workflows, adding tags to workflows, and exporting and importing workflows In another example embodiment, a system is provided that includes a memory that stores computer executable components. The system includes a processor that executes the computer executable components stored in the memory. The computer executable components include an algorithm orchestration component that receives image processing requests from medical imaging providers via a network and identifies workflows applicable to medical images associated with the medical image processing requests, the workflows respectively comprising one or more medical image inferencing models, and a workflow execution component that executes the workflows on the medical images in association with reception of the image processing requests.

In various implementations, the computer executable components further comprise an activity logging component that tracks activity information regarding the image processing requests and the workflows executed for the image processing requests. For example, the activity information can include identify the specific workflows that were executed for each request and the workflow status (e.g., completed or failed), the one or more medical image inferencing models executed for the image processing requests, the devices from which the requests were received, attributes of the medical images (e.g., study type, study modality, etc.), errors detected in the workflows, and the like. A management component can further provide access to the activity information via a management application.

In some implementations, the computer executable components further an activity analysis component that processes the activity information and generates performance evaluation report information based on the activity information, and a dashboard component that presents the performance evaluation report information via a dashboard user interface of the management application. The workflow execution engine can also generate and returns workflow results to the medical imaging providers, the workflow results comprising outputs of the one or more medical image inferencing models, and computer executable components can further comprise a feedback component that receives feedback regarding accuracy of the outputs of the one or more inferencing models, wherein the activity analysis component further generates the performance evaluation report information based on the feedback.

The activity logging component can further generate activity logs for the image processing requests, the activity logs identifying the workflows executed for each image processing request and the execution status of the workflows. The computer executable components can further comprise an auditing component that provides access to the activity logs via a management application and provides an auditing function via the activity logs for performing root cause analysis regarding workflow execution errors encountered for one or more of the workflows.

In some examples, elements described in connection with the disclosed systems can be embodied in different forms such as a computer-implemented method, a computer program product, or another form.

DESCRIPTION OF THE DRAWINGS

FIG. 7 presents an example algorithm management user interface (UI) in accordance with one or more embodiments of the disclosed subject matter.

FIG. 8 presents an example algorithm management editor UI in accordance with one or more embodiments of the disclosed subject matter.

FIGS. 9A-9B present example an algorithm onboarding UI in accordance with one or more embodiments of the disclosed subject matter.

FIGS. 10A-10B present an example workflow management UI in accordance with one or more embodiments of the disclosed subject matter.

FIGS. 13A-13D presents example task registry UIs in accordance with one or more embodiments of the disclosed subject matter.

FIGS. 14A-14B present example device management UIs in accordance with one or more embodiments of the disclosed subject matter.

FIGS. 15A-15B present example activity log UIs in accordance with one or more embodiments of the disclosed subject matter.

DETAILED DESCRIPTION

Figure 1:
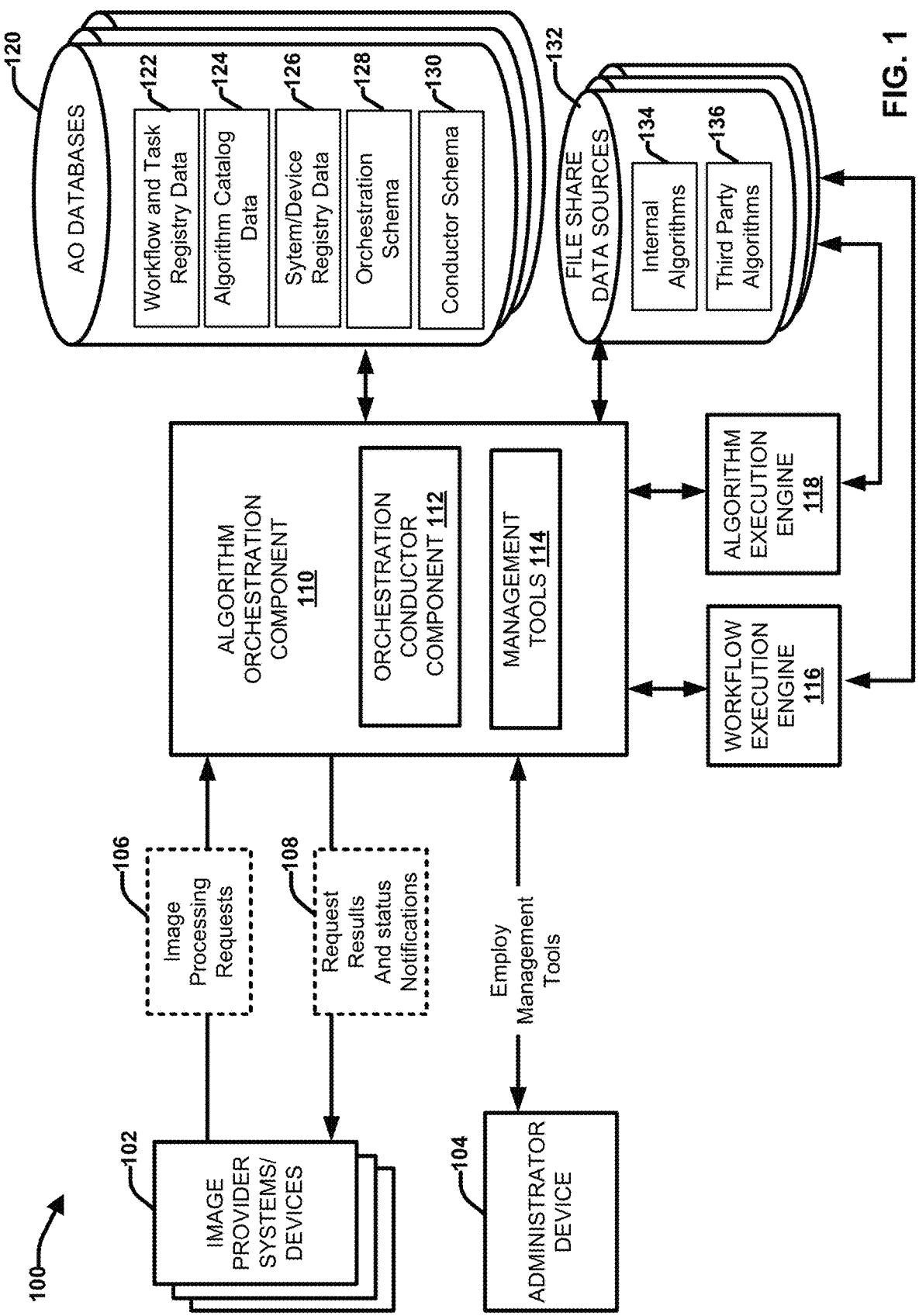
FIG. 1 illustrates a block diagram of an example algorithm orchestration system in accordance with one or more embodiments of the disclosed subject matter.

The following detailed description is merely illustrative and is not intended to limit examples illustrated and described herein and/or application or uses of such examples. Furthermore, there is no intention to be bound by any expressed or implied information presented in the preceding Summary section or in the Detailed Description section.

The disclosed subject matter relates to algorithm orchestration in the medical imaging domain, including techniques for orchestrating execution of algorithms on medical images according to pre-defined workflows and techniques for managing workflow and model execution. The disclosed algorithm orchestration techniques employ a centralized, network accessible algorithm orchestration component that serves as middle layer connecting medical image providers with AI model processing web services for executing AI models on their medical images and returning consumable outcomes/results. In this regard, the algorithm orchestration component can receive a medial image (or images) from a medical imaging provider in association with a request to process the medical image using one or more image processing algorithms. Given a medical image, the algorithm orchestration component can identify and perform one or more workflows on the medical image that involve processing the medical image using one or more medical image processing algorithms compatible with that image. The algorithm orchestration component further provides the requesting entity with the workflow results/outcomes.

In this context, a workflow refers to a set of workflow instructions that define what computer-executed processing steps to apply to the medical image (or images). A workflow consists of an orchestrated and repeatable pattern of service calls to process medical images, execute algorithms and produce outcomes to be consumed by other systems. In various embodiments, the algorithms can include, but are not limited to, image restoration algorithms (e.g., used to improve the quality of the image), image analysis algorithms (e.g., classification/diagnosis models, organ segmentation models, etc.), image synthesis algorithms (e.g., used construct a three-dimensional image based on multiple two-dimensional images images), image enhancement algorithms (e.g., used improve the image by using filters or adding information that will assist with visualization), and image compression algorithms (e.g., used to reduce the size of the image to enhance transmission times and storage required).

In various embodiments, the workflows can be configured to can apply algorithms in different clinical contexts and filter images/studies based on metadata associated therewith (e.g. modality, series, study description etc.). The workflows can also be configured to invoke representational state transfer (REST) services to retrieve information from other systems. The workflows can further be configured to execute algorithms, including executing algorithms and other tasks in parallel. The workflows can also be configured to execute asynchronous tasks and wait for the task to be completed. The workflows can also be configured to evaluate the output of a task and use it as input for another task.

In some implementations, the workflows can include at least one algorithm that that could be used to assist a radiologist to diagnose and treat a disease. For example, a workflow can call one or more algorithms including AI algorithms that can be applied to the medical image to determine probabilities related to a given medical condition of a patient from which the image was obtained. However, the concept of algorithms as used herein are not limited to machine learning (ML) or deep learning (DL) models. For example, in addition to medical image inferencing models, the workflows described herein can integrate various algorithms for filtering input images based on associated metadata (e.g., based on patient related demographics, based on image attributes, and other factors), heuristic algorithms, algorithms for controlling order and timing of service calls throughout the workflow, and other types of algorithms.

In various embodiments, the algorithm orchestration component can employ an algorithm catalog that identifies the algorithms that are included in the pre-defined workflows that are available to analyze a given medical. The catalog of algorithms can include various internal and third-party algorithms/models that can be integrated into workflows. In some embodiments, the algorithms/models can be integrated into workflows as HTTP tasks and invoked/called as web-service calls via one or more networks (e.g., the Internet or the like). In this regard, the algorithm orchestration component can connect healthcare provider systems with algorithms created by various AI model providers/developers, wherein the algorithm orchestration component orchestrates accessing and applying the algorithms to medical images as web-services using defined application program interfaces (APIs) for the algorithms. Additionally, or alternatively, the algorithms/models can be integrated into workflows as "jobs." Specifically, an algorithm/model and other tasks defined by computer executable instructions can be wrapped in a Kubernetes Job function and the algorithm orchestration component can execute it asynchronously inside the cluster on behalf of the user. This feature opens multiple possibilities specially related to legacy systems where the client service is not under HTTP and is only a simple command line and/or executable.

In some embodiments, image providers can identify or indicate the specific algorithms and/or workflows to apply to a medical image in association with provision of the image processing request. Additionally, or alternatively, the algorithm orchestration component can determine what workflows and associated algorithms to apply to a given image based on metadata associated with the image and the information included in the algorithm catalog. With these embodiments, the algorithm orchestration component can automatically select at least one workflow to execute on a medical image.

The algorithm orchestration component further directs a workflow execution engine to execute the workflow and apply the one or more algorithms included in the workflow to the image. In various embodiments, the workflow execution process involves employing an algorithm execution engine to execute the one or more AI algorithms included in the workflow by calling/invoking the algorithms at their network accessible file source (e.g., using their corresponding API calls as defined by the workflow code/logic). Based on various determinations generated in response to execution of the workflow, the algorithm orchestration component can generate and send notifications (e.g., texts, e-mails, reports) to the image provider, radiologist or another related healthcare system to assist them in their reporting of patient results and diagnosis.

In accordance with various example implementations, the algorithm orchestration component can be configured to interface with a medical image storage system employed by a medical image service provider, such as a Picture Archiving and Communication System (PACS) and/or a Vendor Neutral Archive (VNA). In accordance with these example implementations, when a new medical image/image study is received at the medical image storage system, the medical image provider/storage system can be configured to send a hypertext transfer protocol (HTTP) request to an API exposed by an API gateway for the algorithm orchestration component. For example, the request can be identified as a "study processes notification" and can contain the study metadata and the payload. The gateway can be configured to forward the request to the algorithm orchestration conductor that validates the request payload and respond with a request execution identifier (ID) and a status. The algorithm orchestration component can then direct the workflow execution engine to invoke all (or one or more) applicable workflows for the image/imaging study. In implementations in which two or more workflows are applicable to the image/image study, the workflow execution engine can execute each workflow as a separate thread.

Typical workflows will start by validating the medical image metadata to determine whether the image satisfies defined workflow requirements (e.g., regarding modality, view position, study description etc.). In accordance with these workflows, if the workflow execution engine determines the image/image study satisfies the workflow requirements, the algorithm orchestration component and/or the workflow execution engine transfers the image/study data from the image source (e.g., the PACS, VNA, or the like) to a local file storage employed by the algorithm orchestration component. When the transfer is complete, the workflow execution engine executes all algorithms defined in the workflow, employing the algorithm execution engine to execute any algorithms of the workflow defined in the algorithm catalog. In this regard, for each algorithm included in the workflow, the workflow execution engine invokes/calls the algorithm as defined in the algorithm catalog and waits for the algorithm execution engine to return a response. Once the response of all the algorithms included in the workflow have been received, the algorithm orchestration component transfers the output files produced by the algorithms back to the image/image study source system (e.g., the PACS, the VNA or the like), and sends a notification message to the imaging providing notifying the provider that the processing of the image/study is complete. This notification message can also include information identifying the specific algorithms executed and the results for each algorithm.

In this regard, the algorithm orchestration component can serve as a bridge between client input metadata and AI models applied to analyze the image to provide requested and/or customized messages in a requested format (e.g., e-mail, text message). The algorithm orchestration component can connect with AI models for diagnosis of disease conditions (e.g., PTX, Stroke, MR) and receives a confidence score from the AI models indicating probabilities which can be passed on to the end user solutions (e.g., via activity dashboard interface). The algorithm orchestration component can be integrated with substantially any user platform that desires an AI model solution to facilitate their worklist priority. For instance, in case of emergency medical situations, the algorithm orchestration component in response to workflow instructions facilitates efficient and review of magnetic resonance/computed tomography (MR/CT) images by an AI algorithm and generates a priority list to expedite the respective healthcare provider's report. The algorithm orchestration component can be integrated as a middle layer between the medical image provider and AI model provider in order to populate the radiologist/healthcare provider end system with summary messages, findings, and/or significance of the diagnosis in addition to secondary capture with annotated overlay support provided with the respective medical images. Thus, in one example, algorithm orchestration enables workflow instructions to be rapidly generated that when executed, allow healthcare users to customize diagnostic reporting, information flow, and notification for downstream reporting to other members of the healthcare team.

Various application services are supported by the systems and methods described herein. In one example application service example, workflow processing is provided by the algorithm orchestration component that executes a given workflow having workflow instructions that define the types of analytical/diagnostic processing to be applied to a given medical image and associated metadata. The algorithm orchestration component operates with an algorithm catalog that defines available algorithms for a given image and an algorithm execution engine to execute selected algorithms by the algorithm orchestration component in response to the workflow instructions.

In another application service example, algorithm management interface and tools can be provided. This includes the process of viewing existing algorithms, onboarding algorithms, editing an algorithm, searching an algorithm, and deleting an algorithm. These algorithms are implicated by the workflow and selectively associated with a given type of image (e.g., chest, brain, extremity, and so forth). An algorithm management interface can be provided that enables setting diagnostic thresholds that define whether or not a given medical condition (e.g., pneumothorax condition (PTX)) is implicated based on the probability determined by the selected model algorithms during workflow processing.

In another example application service example, a workflow configuration tool and user interface (UI) can be provided to facilitate workflow development and creation. This tool can be enabled with features that would be of interest to an administrator who is trying to quickly satisfy a radiologist's request for some type of analytical/diagnostic output from the system without having to redesign existing software or commission new software for the requested task. The tool allows for the creation of workflows composed of workflow instructions that define associations and relationships between what the administrator (the one setting up the workflow) wants to happen (various checks on the image data and metadata) from when the image is received to when/how a notification/report is generated to the radiologist.

In yet another application service example, an activity dashboard interface provides results from AI model analysis with respect to actual radiological analysis of the same or similar images. This includes showing the number of available studies that were employed to generate the AI model analysis along with false positive rate versus true positive rate analysis. The activity dashboard provides a measure of confidence to the radiologist for the underlying automated analysis of the AI models. Compliance to desired diagnostic standards can be monitored in the Activity Dashboard where a one or more radiologist's actual diagnoses is compared to AI model output.

In yet another application service example, simulation and testing tools can be provided for workflow instructions. A simulation tool can be provided that operates with the workflow configuration tool, where the workflow can be run in an offline setting using test images or newly acquired images before implementing in the live system operated by the algorithm orchestration component. In still yet another application service, security (e.g., network or file security) can be managed between components that interact with the algorithm orchestration component. This includes how components of the system communicate and what type of security credentials are passed for the respective communications to proceed.

The terms "algorithm" and "model" are used herein interchangeably unless context warrants particular distinction amongst the terms. The term "image inferencing algorithm" is used herein to refer to an AI/ML algorithm configured to perform an image processing or analysis task on images. The image processing or analysis task can vary. In various embodiments, the image processing task can include (but is not limited to): an image restoration task (e.g., used to improve the quality of the image), an image synthesis task (e.g., used construct a three-dimensional image based on multiple two-dimensional images images), an image enhancement task (e.g., used improve the image by using filters or adding information that will assist with visualization), and image compression task (e.g., used to reduce the size of the image to enhance transmission times and storage required). Some example image analysis task can include, but are not limited to, a classification task (e.g., diagnostic), a segmentation task (e.g., organ segmentation, region of interest segmentation, etc.), an object recognition task, a motion detection task, a video tracking task, an optical flow task, and the like. The image inferencing models described herein can include 2D image processing models as well as 3D image processing models. The image processing model can employ various types of AI/ML algorithms, including (but not limited to): deep learning models, neural network models, deep neural network models (DNNs), convolutional neural network models (CNNs), generative adversarial neural network models (GANs) and the like. However, the concept of algorithms or models as described herein here is not limited to machine learning or deep learning models. The terms "image inferencing algorithm," "image inferencing model," "image processing algorithm," "image processing model," "image analysis model," and the like are used herein interchangeably unless context warrants particular distinction amongst the terms.

The term "image-based inference output" is used herein to refer to the determination or prediction that an image processing model is configured to generate. For example, the image-based inference output can include a segmentation mask, a reconstructed image, an adapted image, an annotated image, a classification, a value, or the like. The image-based inference output will vary based on the type of the model and the particular task that the model is configured to perform. The image-based inference output can include a data object that can be rendered (e.g., a visual data object), stored, used as input for another processing task, or the like. The terms "image-based inference output", "inference output" "inference outcome," "inference result" "inference", "output", "outcome," "predication", and the like, are used herein interchangeably unless context warrants particular distinction amongst the terms.

As used herein, a "medical imaging inferencing model" refers to an image inferencing model that is tailored to perform an image processing/analysis task on one or more medical images. For example, the medical imaging processing/analysis task can include (but is not limited to): disease/condition classification, disease region segmentation, organ segmentation, disease quantification, disease/condition staging, risk prediction, temporal analysis, anomaly detection, anatomical feature characterization, medical image reconstruction, and the like. The terms "medical image inferencing algorithm," "medical image inferencing model," "medical image processing algorithm," "medical image processing model," "medical image analysis model," and the like are used herein interchangeably unless context warrants particular distinction amongst the terms. The outputs, outcomes, etc., of medical image inferencing models are the artifacts produced by an algorithm executed using one or more medical images as input. The outputs can be in different formats, such as for example: a Digital Imaging and Communications in Medicine (DICOM) structured report (SR), a DICOM secondary capture, a DICOM parametric map, an image, text, and/or JavaScript Object Notation (JSON).

The types of medical images processed/analyzed by the medical image inferencing models described herein can include images captured using various types of image capture modalities. For example, the medical images can include (but are not limited to): radiation therapy (RT) images, X-ray (XR) images, digital radiography (DX) X-ray images, X-ray angiography (XA) images, panoramic X-ray (PX) images, computerized tomography (CT) images, mammography (MG) images (including a tomosynthesis device), a magnetic resonance imaging (MRI) images, ultrasound (US) images, color flow doppler (CD) images, position emission tomography (PET) images, single-photon emissions computed tomography (SPECT) images, nuclear medicine (NM) images, and the like. The medical images can also include synthetic versions of native medical images such as synthetic X-ray (SXR) images, modified or enhanced versions of native medical images, augmented versions of native medical images, and the like generated using one or more image processing techniques. The medical imaging processing models disclosed herein can also be configured to process 3D images.

A "capture modality" as used herein refers to the specific technical mode in which an image or image data is captured using one or more machines or devices. In this regard, as applied to medical imaging, different capture modalities can include but are not limited to: a 2D capture modality, a 3D capture modality, an RT capture modality, a XR capture modality, a DX capture modality, a XA capture modality, a PX capture modality a CT, a MG capture modality, a MRI capture modality, a US capture modality, a CD capture modality, a PET capture modality, a SPECT capture modality, a NM capture modality, and the like.

The term "web platform" as used herein refers to any platform that enables delivery of content and services over a network (web (i.e., the web/Internet) using a network transfer protocol, such as HTTP, sFTP, or another network transfer protocol. For example, a web platform can include, but is not limited to, a web-application (i.e., an interactive website), a mobile website, a mobile application or the like. The terms "web platform," "web-based platform," "network platform," "platform," and the like are used herein. interchangeably unless context warrants particular distinction amongst the terms.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 illustrates a block diagram of an example algorithm orchestration system 100 in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

System 100 includes an algorithm orchestration component 110 that facilitates orchestrating various services for medical image providers and administrators related to processing medical images using various image processing algorithms accessed as web-services and/or wrapped jobs. The medical image providers can include essentially any entity that provides medical images for processing by the algorithm orchestration component 110. For example, a medical image provider can include a healthcare system, a hospital system, a medical imaging system, an individual clinical/radiologist (e.g., a sole practitioner) or the like. In system 100, the medial image providers are represented by the image provider systems/devices 102. In this regard, the medical image providers access and employ the services orchestrated by the algorithm orchestration component 110 via one or more systems or devices, represented in system as image provider systems/devices 102.

The image provider systems/devices 102 can include essentially any system or device that provides medical images to the algorithm orchestration component 110. For example, in various embodiments, the image provider systems/devices 102 can be, include, or be communicatively coupled one or more data sources that store medical images and/or information related to the medical images, such as metadata describing various attributes of the medical images, radiology reports associated with the medical images, relevant patient information, and the like. For example, the attributes can refer to patient data associated with the medical image such as name, age, previous medical history data, and/or other data relating to the patient and the medical image. Attributes can also describe exam series and image level metadata to identify and/or execute related workflows. For example, the metadata associated with the medical images can include information regarding (but not limited to), image acquisition protocols, image quality, signal noise, image index size, matrix size, resolution, orientation, capture modality, type and dimensions of anatomical features depicted in the image data, image rating, image quality, image storage location (or locations), image capture time, and other features. The metadata tags can also include (but are not limited to) information describing the image type, the anatomical part depicted in the image data, the medical condition/pathology reflected in the image data, patient demographics, and relevant patient medical history factors.

These image provider systems/device 102 can comprise different types of data sources that are provided by the same entity/organization that owns/operates the algorithm orchestration component 110 as well as provided by various different third party or external entities/organizations. For example, the image provider systems/devices 102 can include or be communicatively coupled to one or more internal medical image databases, one or more external medical image databases, one or more internal and external workstations, one or more internal and external PACS and consoles, and so forth. The image provider systems/devices 102 can be located on the same network as well as across multiple networks and regions around the world. The number of image provider systems/devices 102 is unlimited.

In this regard, the term "internal" as applied to an image provider system/device 102 is used herein to refer to a proprietary data source/system associated with a single enterprise that owns, provides, manages and/or controls the features and functionalities of the algorithm orchestration component 110. For example, in some implementations, the single enterprise can be a health information technology (HIT) company (such as General Electric (GE) Healthcare Corporation) that provides a range of products and services that include medical imaging and information technologies, electronic medical records, medical diagnostics, patient monitoring systems, drug discovery, biopharmaceutical manufacturing technologies and the like. According to this example, the HIT company can also provide, manage, and/or control the algorithm orchestration component 110 as well as employ the algorithm orchestration component 110 to process their own medical images using various image processing algorithms. In another implementation, the single enterprise can comprise a hospital organization that provides medical services to patients via one or more hospitals, outpatient medical facilities, and the like. Regardless of the nature, operations and/or services provided by the enterprise, the image provider systems/devices 102 can comprise internal data sources/systems that are owned and/or operated by the enterprise that owns/manages the algorithm orchestration component 110.

The term "external" as applied to a medical image provider is used herein to refer a system, device and/or medical image data source that is owned and/or operated by a third party entity that does not provide, manage, and/or control the algorithm orchestration component 110.

The medical images provided by the image provider systems/devices 102 can include images captured using essentially any medical imaging modality. For example, the medical images can include but are not limited to: conventional X-ray (XR) images, digital radiography (DX) X-ray images, X-ray angiography (XA) device, panoramic X-ray (PX) images, computerized tomography (CT) images, mammography (MG) images, (including a tomosynthesis device), magnetic resonance imaging (MRI) images, ultrasound (US) images, color flow doppler (CD) images, position emission tomography (PET) images, single-photon emissions computed tomography (SPECT) images, nuclear medicine (NM) images, and other types of medical images. The medical images can also include or be associated with (e.g., as metadata) raw pixel data, waveform data, three-dimensional or depth data, point cloud data and the like.

In various embodiments, the image provider systems/devices 102 can provide medical images and associated metadata formatted according to the DICOM standard.

DICOM is the worldwide standard for handling, storing, printing, and transmitting information in medical imaging. It includes a file format definition and a network communications protocol. DICOM is used worldwide to store, exchange, and transmit medical images. For example, DICOM incorporates standards for the various imaging modalities such as radiography, ultrasonography, computed tomography, magnetic resonance, mammograph, and the like. DICOM includes protocols for image exchange (e.g., via portable media such as DVDs), image compression, 3D visualization, image presentation, and results reporting. Working with imaging data sets of size and complexity scales needed to develop sophisticated AI imaging diagnostic models can be somewhat easier than with other types of datasets due to the wide adoption of DICOM, a standard that has been in place for medical imaging for more than twenty years. For imaging, DICOM fills the role of connecting all the modalities in the hospital. The printers, displays, MRI machines, and other acquisition devices all communicate using DICOM standards.

In some implementations, the image provider systems/devices 102 can be or include one or more PACS. A PACS provides economical storage and convenient access to images from multiple modalities (source machine types). Electronic images and reports can be transmitted digitally via a PACS, which eliminates the need to manually file, retrieve, or transport film jackets, the folders used to store and protect X-ray film. The universal format for PACS image storage and transfer is DICOM. Non-image data, such as scanned documents, may be incorporated using consumer industry standard formats like PDF (Portable Document Format), once encapsulated in DICOM.

Additionally, or alternatively, the image provider systems/devices 102 can be or include one or more a vendor neutral archive (VNA) systems. A VNA is a medical imaging technology in which images and documents (and potentially any file of clinical relevance) are stored (archived) in a standard format with a standard interface, such that they can be accessed in a vendor-neutral manner by other systems. In this regard, VNAs can collect and store images from multiple modalities and departments (e.g., radiology, cardiology, orthopedic, etc.) and pull everything into one big archive. In addition to DICOM images, VNAs can store data objects not directly related to images or DICOM data, such as human-generated requests and reports, health level 23 clinical document architecture (HL23-CDA) documents, and the like. The VNAs can also employ non-DICOM access protocols, such as Cross-Enterprise Document Sharing (XDS and XDS-I). VNAs can also provide cross-domain identity and code resolution (patient ID, accession number, procedure codes), dynamic DICOM tag morphing, and other adaptable features. The image provider systems/devices 102 can also be or include workstations (e.g., deployed at one or more computing devices) where medical images are viewed and/or processed for various purposes (e.g., AI model development workstations, radiologist viewer workstations, annotation workstations, etc.).

The algorithm orchestration component 110 can receive image processing requests 106 from medical image providers (e.g., via their respective image provider systems/devices 102) that correspond to requests to apply one or more image processing algorithms to a medical image or group of medical images, such as a group of medical images included in particular imaging study. These image processing algorithms can include various medical image inferencing algorithms or models (e.g., AI models). For example, the image processing algorithms can include, but are not limited to, image restoration algorithms (e.g., used to improve the quality of the image), image analysis algorithms (e.g., classification/diagnosis models, organ segmentation models, etc.), image synthesis algorithms (e.g., used construct a three-dimensional image based on multiple two-dimensional images images), image enhancement algorithms (e.g., used improve the image by using filters or adding information that will assist with visualization), and image compression algorithms (e.g., used to reduce the size of the image to enhance transmission times and storage required).

In the embodiment shown, the image processing algorithms are stored at one or more network accessible locations that are accessed and applied to the medical images (e.g., by the workflow execution component and/or the algorithm execution engine 116 and/or the algorithm execution engine 118) in accordance with pre-defined workflows. In various embodiments, the image processing algorithms can be integrated into the predefined workflows as HTTP tasks and accessed and applied to the medical images as web-services in accordance with the pre-defined workflows. Additionally, or alternatively, the algorithms/models can be integrated into workflows as "jobs." Specifically, an algorithm/model and other tasks defined by computer executable instructions can be wrapped in a Kubernetes Job function and the algorithm orchestration component can execute it asynchronously inside the cluster on behalf of the user. This feature opens multiple possibilities specially related to legacy systems where the client service is not under HTTP and is only a simple command line and/or executable.

In the embodiment shown, system 100 includes one or more file share data sources 132 that correspond to network accessible data sources where the image processing algorithms are stored. Additionally, or alternatively, one or more of the algorithms can be stored and accessed in the one or more AO databases 120. The image processing algorithms can include internal algorithms 134 as well as third party algorithms 136. In this context, the internal algorithms 134 can include various image/medical image processing algorithms/models provided by the same entity that owns/manages the algorithm orchestration component 110 and the third party algorithms 136 can include various image/medical image processing algorithms/models provided by various third party AI developers/providers. In this regard, the algorithm orchestration system 100 can enable various different medical image providers to access and employ the algorithm orchestration component 110 to process their medical images using various medical image inferencing algorithms or models provided by various AI model developers/providers.

The algorithm orchestration component 110 can include an orchestration conductor component 112 to orchestrate fulfilling the image processing requests 106 and returning request results and status notifications 108 to the medical image providers. In particular, the orchestration conductor component 112 can coordinate the interaction between the image provider systems/devices 102 and the various components of the algorithm orchestration system 100 (and other systems describe herein) used to retrieve and store the medical image data to be processed using the algorithms, execute the workflows and invoke the algorithms associated therewith, and return the request results and status notifications 108. As described in greater detail below, these components can include (but are not limited to), a workflow execution engine 116, an algorithm execution engine 118, one or more file share data sources 134, one or more algorithm orchestration databases 120, and various additional software and hardware components.

In this regard, the algorithm orchestration component 110 serves as a middle layer connecting medical image providers with medical image processing services for executing AI algorithms on their medical images and returning consumable outcomes/results. From the perspective of the imaging provider, interactions with the algorithm orchestration component 110 can involve sending imaging processing requests 106 when a new medical study is available for processing, including pushing the medical image study to the algorithm orchestration component 110 for processing. Imaging providers can also receive notifications from the algorithm orchestration component 110 regarding what workflows and/or algorithms that are applicable for processing the imaging study, notifications regarding completion of processing of the study and the results. In some implementations, the image provider systems/devices 102 can initiate the transfer of an imaging the study to the algorithm orchestration component 110 when there is a match with one or more workflows. Other interactions between an imaging provider and the algorithm orchestration component 110 can include (but are not limited to), initiating the transfer of the algorithm results (if available) once all algorithms are executed, canceling a previously submitted image processing request, and sending requests with different priorities levels.

In various embodiments, the algorithm orchestration component 110 provides the image provider systems/devices 102 access to the internal algorithms 134 and the third-party algorithms 136 as web-services and/or jobs that can be executed simultaneously for multiple providers and multiple images in accordance with pre-defined workflows. In this regard, the algorithm orchestration component 110 supports different workflows based on the same set of services arranged in different compositions.

In this context, a workflow refers to a set of computer executable workflow instructions that define what computer-executed processing steps to apply to the medical image (or images). A workflow consists of an orchestrated and repeatable pattern of service calls to process medical images, execute algorithms and produce outcomes to be consumed by other systems. In various embodiments, a workflow is composed of nodes corresponding to different computer-executable instructions. These nodes can include, but are not limited to, a Start node, and End node, a Decision, a Task node, Sub-Workflow node, a Wait node, a Fork node, a Join node and a Function node. Start and End nodes define where the workflow starts and ends. A Decision node corresponds to a decision-making task and is used to evaluate expressions that will define the next step to be executed (similar to a switch-case instruction in programming languages). For example, a Decision node can be used to filter input images based on one or more defined criteria to ensure the workflow proceeds on authorized images. For instance, many workflows can begin with a Decision node that stops execution of the workflow on an input image if the input image does not satisfy one or more defined criterion (e.g., based on various parameters).

A Task node represents a task to be executed by the workflow. These can include HTTP tasks, Lambda tasks, Kubernetes jobs (e.g., commonly referred to as k8s jobs), or the like. In various embodiments, Task nodes correspond to an algorithm/model to be called and executed, such as a call to an internal algorithm 134 and/or a third-party algorithm 136. Task nodes can also be used to invoke other HTTP services, Lambda tasks, and/or jobs, such as services including retrieving an image or other data for processing (e.g., from a PACS or the like), moving data from one source to another, deleting data, or the like. In various embodiments, the workflow instructions for a task node corresponding to an algorithm/model to be called/executed can include (e.g., as embedded therein) the algorithm execution instructions for calling and executing the corresponding algorithm, such as the network accessible algorithm file location, the API for accessing and running the algorithm and receiving the results, and the like. In this regard, a task node corresponding to an algorithm/model can essentially include a link to the actual algorithm/model, wherein execution of the task node involves using the link to access and run the model on an input image and receive the results.

A Sub-Workflow node corresponds to a sub-workflow that can involve any of the nodes used for a Workflow. A Wait node adds a delay in the workflow based on one or more defined conditions. For example, a Wait node can be used to restrict initiation of a task until completion of another task or sub-workflow. Wait nodes can thus be used to track the execution of asynchronous tasks as part of the orchestration and are usually used in operations that are time consuming like moving an imaging study from PACS to the algorithm orchestration component (or a local data storage used by the algorithm orchestration component 110), pushing algorithm results to PACS or executing a deep learning model. A Fork node can be used to fork the workflow execution into two or more parallel processes. A join node can be used to join two or more parallel processes initiated by a Fork node and can waits for completion of the two or more parallel processes. A function node can be used to evaluate an expression and provide a response. For example, a function node can be used to perform a data conversion, run a calculation, or another function that can be expressed as script that can be run by the workflow execution engine 116. Workflows can aggregate the outcomes of different algorithms executed and notify other systems about the status of the orchestration.

Figure 2A:
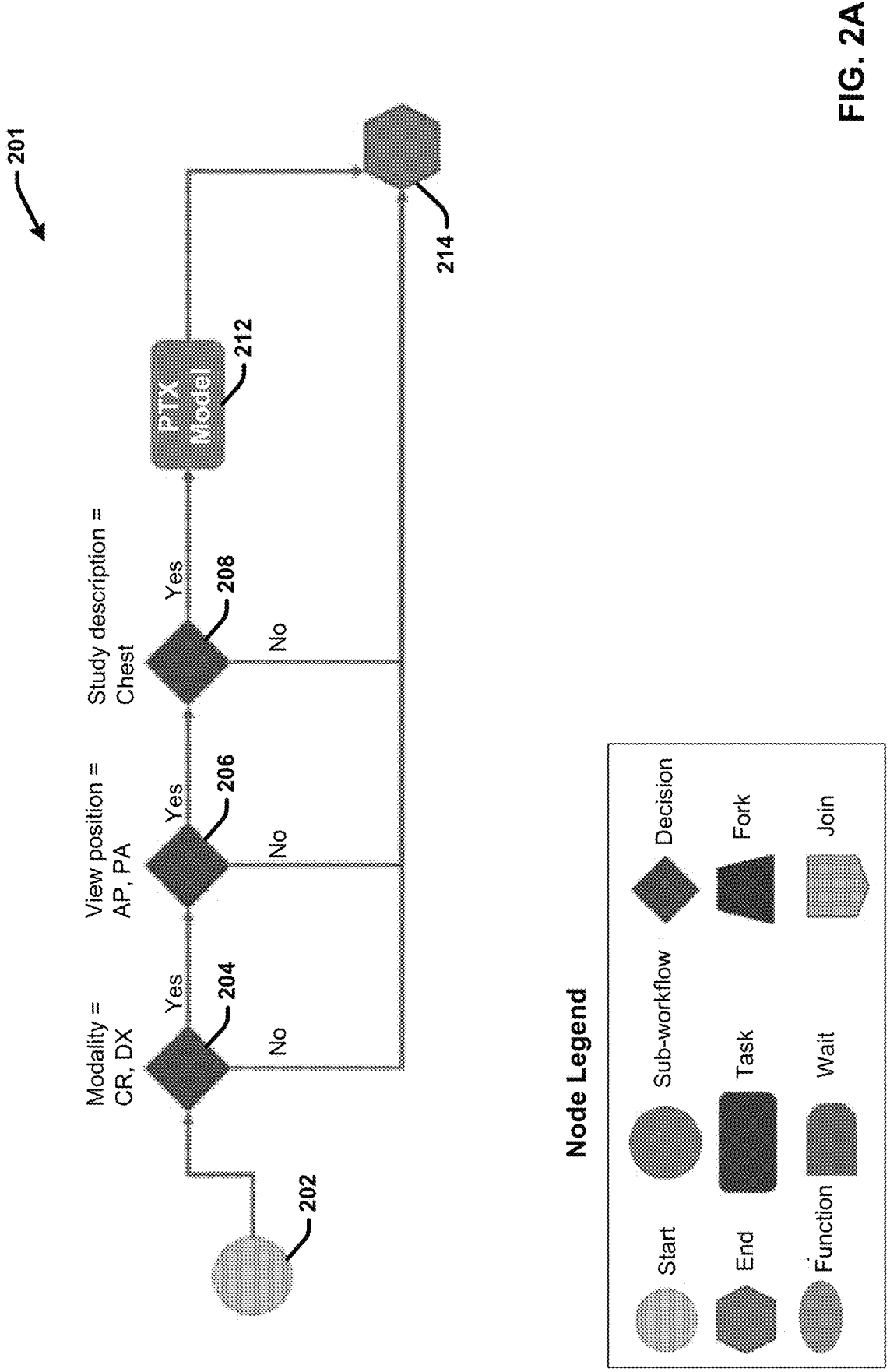
FIGS. 2A-2C present example workflow diagrams in accordance with one or more embodiments of the disclosed subject matter.
Figure 2B:
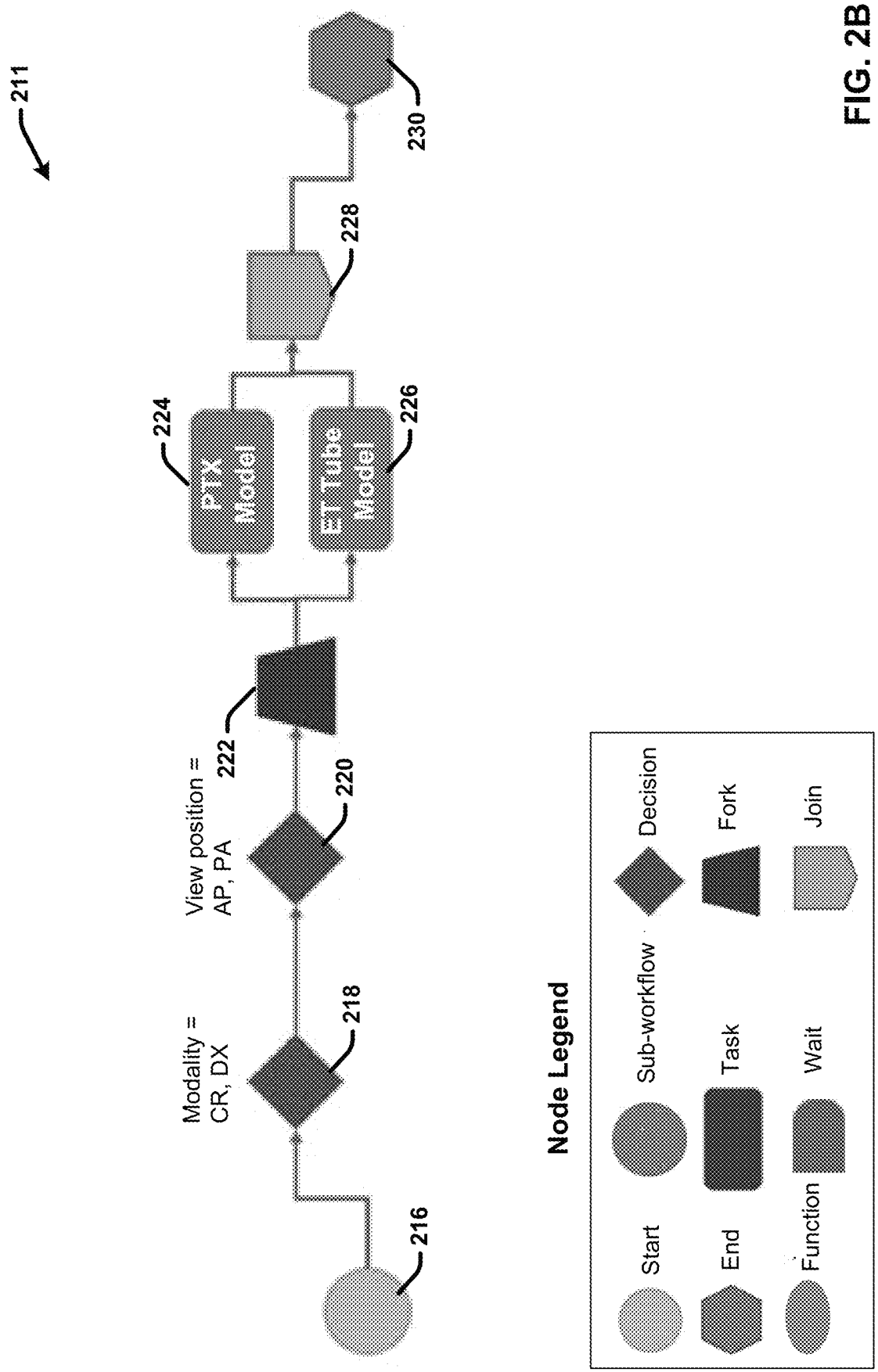
Figure 2C:
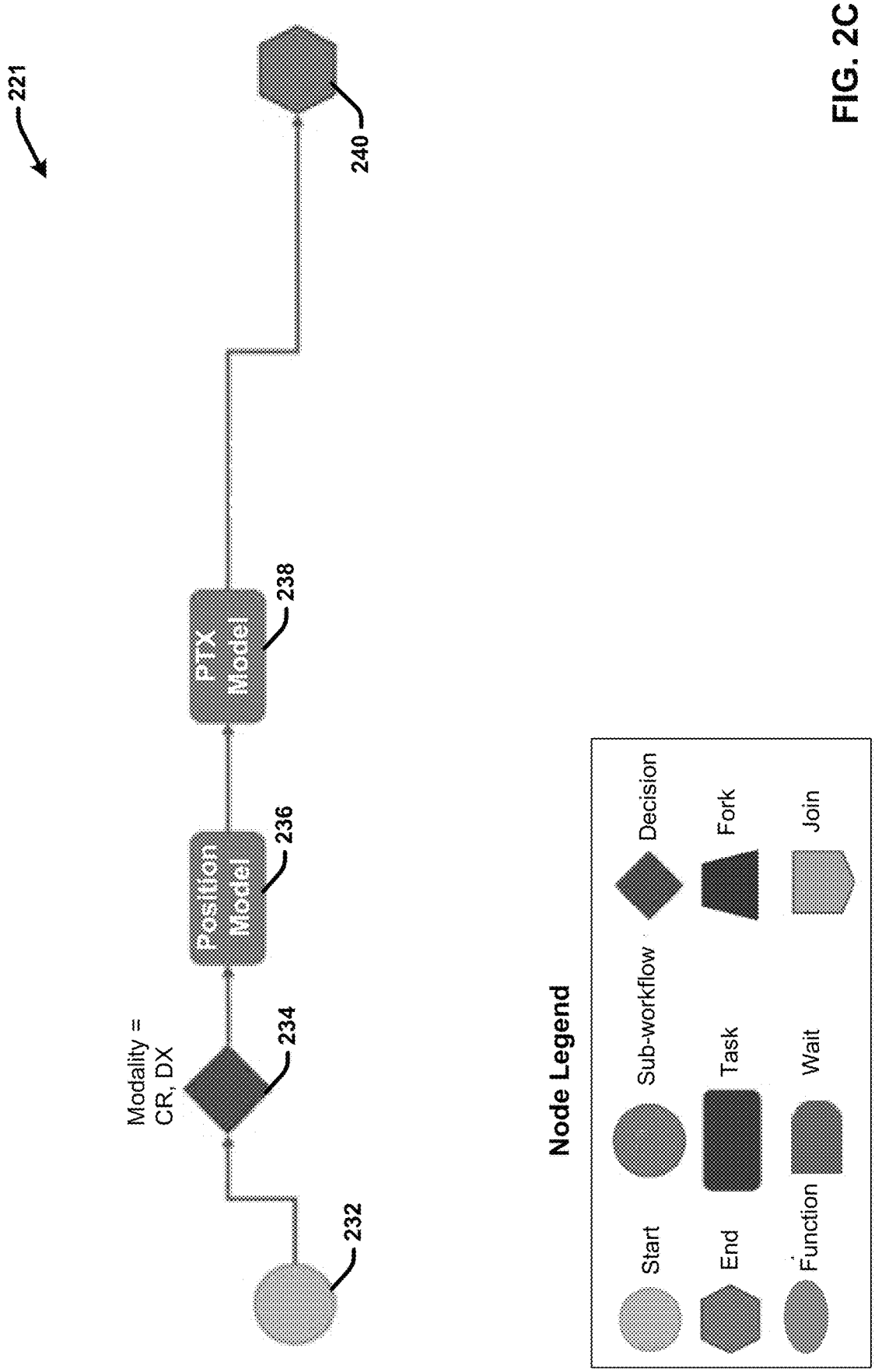

FIGS. 2A-2C present example workflow diagrams in accordance with one or more embodiments of the disclosed subject matter. The diagrams shown in FIGS. 2A-2C exemplify some of the different nodes described above as configured to perform defined workflow instructions. The workflow diagrams presented in FIGS. 2A-2C correspond to example workflows that can be included in the workflow and task registry data 124 and executed by the workflow execution engine 116. Each of the different nodes are represented by a different symbol shown in the node legend. FIG. 2A illustrates an example workflow diagram 201 for executing a single algorithm which in this example is a pneumothorax (PTX) classification model. The workflow starts at start node 202 and employs three decision nodes for evaluating the input image prior to proceeding with calling/applying the PTX model. In this regard, at 204 a first decision node is used to evaluate whether the modality of the input image is CR, DX. If the modality is not CR, DX, the workflow ends at 214. At 208, a second decision node is used to evaluate whether the view position is AP, PA. If the view position is not AP, PA, the workflow ends. A third decision node is then used to evaluate whether the study description is classified as chest study at 208. If yes, the workflow proceeds and the PTX model is called and applied to the input image at 212. If not, the workflow ends at 214.

FIG. 2B illustrates an example workflow diagram 211 that involves parallel algorithm execution. Workflow diagram 211 starts at 216 and proceed through two decision nodes, node 218 and node 220. If the input image satisfies both decision node criteria, the workflow proceeds. At 222, a fork node is used to split the workflow into two parallel processes. At 224, the PTX model is called and applied to the input image. At the same time, at 226, an endotracheal (ET) tube model is called and applied to the input image. At 228, a join node is used to wait for and combine the result of both models and then workflow ends at 230.

FIG. 2C illustrates an example workflow diagram 221 that involves sequential algorithm execution. In accordance with workflow diagram 221, the workflow begins at 232 followed by a modality evaluation decision node 234. If the input image satisfies the modality criteria, at 236, a position model is called and applied to the input image. Upon reception of the results, at 238 the PTX model is called and applied to the input image. The workflow then ends at 240. In this example, the PTX model is executed after the position model has executed, where the position model and the PTX model are series connected.

With reference again to FIG. 1, in various embodiments, the pre-defined workflows available for processing medical images can be provided in one or more AO databases accessible to the workflow execution engine 116. For example, in the embodiment, shown, the one or more AO databases can include workflow and registry task data 122. In some implementations, the workflow and task registry data 124 can include/store separate data files for each defined workflow, wherein the data files include the computer executable workflow instructions (e.g., code/logic) for executing the workflows. Additionally, or alternatively, the workflow files can be stored at one or more other accessible databases (e.g., one or more of the AO databases 120) and the workflow and task registry data 124 can be or correspond to an index that includes information identifying and/or describing the workflows and provides the file location for the respective workflows where they can be accessed by the workflow execution engine 116.

Regardless of the location where the workflow files are stored, each workflow can be identified by a unique title, name or workflow identifier (ID). The respective workflows identified and/or included in the workflow and task registry data 124 can also include or be associated with information that describes the workflow (e.g., a summary of the workflow) and provides relevant information that identifies or indicates the medical images that the workflow is applicable to. For example, in various embodiments, the workflows can be associated with metadata tags that identify attributes of medical images capable of being processed by the workflow. In some embodiments, each workflow identified or included in the workflow and task registry data 124 can also include or be associated with information that identifies the creator (or creators) of the workflow, the one or more tasks/algorithms included therein, the timing/date when the workflow was created and/or last updated, and various other relevant information regarding the workflow. As described in greater detail infra with reference to FIGS. 5A and 11A-11X, the algorithm orchestration component 110 can provide a workflow creation tool that provides for creating and editing workflows included in the workflow and task registry data 122.

The one or more AO databases 120 can also include algorithm catalog data 122 that identifies the various internal algorithms 134 and third-party algorithms 136 included in the defined workflows and/or that are otherwise available for application to medical images. In this regard, in some embodiments, the algorithm catalog data 124 include or correspond to an algorithm index that includes information identifying the algorithms stored at the one or more file share data sources 132 that have been onboarded to system 100 and included in the defined workflows and/or that are otherwise available for application to medical images. For example, in various embodiments, each of the algorithms can include a unique identifier, title, name or the like. The algorithm catalog data 124 can further include algorithm execution instructions that define how to access and execute the respective algorithms and receive the results/outputs. For example, in various embodiments, the algorithms can be executed as web-services/.HTTP tasks and the algorithm execution instructions can define the code/logic for calling and running the algorithms as web-services, such as the network accessible algorithm file location, the API for accessing and running the algorithm and receiving the results, and the like. Additionally, or alternatively, the algorithms/models can be integrated into workflows as Lambda tasks, Kubernetes jobs, or a similar type of HTTP alternative execution method. This feature opens multiple possibilities specially related to legacy systems where the client service is not under HTTP and is only a simple command line and/or executable. The algorithm catalog data 124 can also include additional detailed information for each algorithm, including but not limited to: the provider (e.g., internal or third-party), the version, a description or summary, the creator, the creation/publication date/time, attributes of input images to which the algorithm is applicable, the input data format and the output data format. In some embodiments, the respective algorithms included in the algorithm catalog data 124 can also be associated with information describing one or more parameters of the algorithms. For example, the parameters can include threshold parameters (e.g., criticality, diagnostic threshold, probability thresholds, etc.), clinical relevance parameters/settings, input image parameters priority settings, and the like. As described in greater detail infra with reference to FIG. 5A and FIGS. 8A-9, the algorithm orchestration component 110 can provide management tools that allow administrators to define or adjust one or more parameters of the algorithms onboarded to the system and available for processing medical images.

The one or more AO databases 120 can further include system/device registry data 126 that identifies the image provider systems/devices 102 from which the algorithm orchestration component 110 is authorized to communicate with 102 in association with receiving and responding to image processing requests 106. The one or more AO databases 120 can further include the orchestration schema 128 and the conductor schema 130.

In various embodiments, the orchestration conductor component 110 can respond to received image processing requests 106 by initially validating the request. In this context, validation refers to ensuring the request is received from an authorized device/system. In this regard, the algorithm orchestration comment 110 can be configured to only process image requests received from authorized image provider systems/devices 102. Information identifying authorized image provider systems/devices 102 from which requests can be received can be received can be provided in the one or more AO database 120 (e.g., a system/device registry data 126). In some implementations, after validating the request, the orchestration conductor component 112 can generate a request identifier for the request and add the request to request processing queue (not shown). Information regarding all receive request can further be stored in the one or more AO databases 120 and tracked by the system 100.

After a request has been validated, the orchestration conductor component 112 can then direct the workflow execution engine 116 to execute one or more workflows identified/included in the workflow and task registry data 122 to the medical image or images associated with the request. The workflow execution process involves executing the instructions defined by a workflow, including executing the steps/actions of the respective nodes as configured. In this regard, the workflow execution engine 116 executes a workflow by executing the code/logic defined by the workflow as provided in the workflow and task registry data 120. As described above, this can involve executing tasks (e.g., task nodes) corresponding to algorithms stored at the one or more file share data sources 132, including internal algorithms 134 and third-party algorithms 136.

In various embodiments, the workflow execution engine 116 access these algorithms as web-services by calling/invoking the algorithms at their network accessible file share data source location (e.g., using their corresponding API calls as defined by the workflow code/logic). For example, in association with processing an input image through a workflow and encountering a task node corresponding to an internal algorithm 134 and/or a third party algorithm 136, the workflow execution 116 engine can employ the algorithm execution instructions defined for the task node to access the algorithm, have the algorithm applied to the image, and to receive the results/outcomes. Additionally, or alternatively, the algorithms/models can be integrated into workflows as "jobs." Specifically, an algorithm/model and other tasks defined by computer executable instructions can be wrapped in a Kubernetes Job function and the algorithm orchestration component can execute it asynchronously inside the cluster on behalf of the user. In some embodiments in which the algorithm is an internal algorithm, the workflow execution engine 116 can access and run/apply the model to the image directly. With these embodiments, the workflow execution engine can be configured to apply the algorithm to the input image. In some embodiments in which the algorithm is a third-party algorithm, the workflow execution engine 116 can send the input image to the third-party system with a request to have the third-party system apply the algorithm to the input image and return the results. With these embodiments, the third-party system can apply/execute the algorithm and provide the results back to the workflow execution engine 116.

Additionally, or alternatively, the workflow execution engine 116 can employ an algorithm execution engine 118 to facilitate executing the algorithms included in a workflow. With these embodiments, the algorithm execution engine 118 can access and apply the algorithms to input images regardless of their source (e.g., internal or third-party) using their corresponding APIs and provide the results back to the workflow execution engine 116. For example, in some implementations, the workflow execution engine can direct the algorithm execution engine 118 to handle calling an algorithm/model defined by a task node at its network accessible location (e.g., at the one or more file share data sources 132), providing the medical image thereto for processing by the algorithm/model, running the algorithm/model and receiving the algorithm/model output/results. In this context, the algorithm execution engine 118 can be or correspond to an inferencing engine that executes the algorithms/models included in a workflow and provides the results to the workflow execution engine 116.

Once the workflow execution engine has completed executing a workflow and compiled the results/outputs of the algorithms run, the orchestration conductor component 122 can provide the results back to the requesting image provider system/device 102. For example, the results 108 can include information identifying the workflow applied, the algorithms applied and the algorithm results. In some embodiments, the algorithm orchestration component 110 can also provide status notifications to the requesting entity regarding the status of the image processing request. For example, the status notifications can indicate whether a workflow has been initiated and when a workflow has been completed. In this regard, based on various determinations generated in response to execution of the workflow, the algorithm orchestration component can generate and send notifications (e.g., texts, e-mails, reports) to the image provider, radiologist or another related healthcare system to assist them in their reporting of patient results and diagnosis.

As noted above, the image processing requests 106 correspond to requests to process a medical image or study (e.g., wherein a study comprises two or more medical images) using one or more image/medical image processing algorithms. In some embodiments, image providers can identify or indicate the specific algorithms and/or workflows to apply to a medical image or study in association with provision of the image processing request 106. With these embodiments, the image processing requests 106 can include information that identifies or indicates the specific algorithms and/to workflows to apply.

In other embodiments, the orchestration conductor component 112 can be configured to direct the workflow execution engine 116 to apply all available workflows included in the workflow and task registry data 124 to the medical image/study. With these embodiments, the Decision nodes included in the workflows are assumed to control application of the appropriate workflows to the medical images. In this regard, as exemplified in the workflow diagrams shown in FIGS. 2A-2C, if a medical image fails to satisfy one or more criteria controlled by a Decision node, the workflow will end and the status of the workflow can be considered "inapplicable." In some implementations of these embodiments, the algorithm orchestration component 110 can notify the requesting entity regarding what workflows were applicable and/or inapplicable, the number of applicable/inapplicable workflows, and the like.

Additionally, or alternatively, the orchestration conductor component 112 can be configured to evaluate a medical image/study associated with an image processing request 106 in view of the workflow and task registry data 122 and/or the algorithm catalog data 124 to determine what workflows to apply to the medical image/study. In this regard, the orchestration conductor component 112 can evaluate information associated with the respective workflows and/or the algorithms/models included therein that identifies or indicates the medical images to which the workflow is applicable to, and select only those workflows for applying to the medical image/study associated with a request. For example, the workflow and task registry data 124 can include information for each (or in some implementation one or more) workflow defined therein that identifies or indicates one or more defined criteria for the input images that can be processed by the workflow. For instance, the one or more defined criteria can be based on image/study type, capture modality, anatomical region/body part depicted, medical condition reflected, and various other factors. With these embodiments, the orchestration conductor component 112 can analyze an image/study and/or its associated metadata to determine and select any applicable workflows defined in the workflow and task registry data 122.

The manner in which the actual image data associated with an image processing request is received/retrieved by the algorithm orchestration component 110 can also vary. In some embodiments, the image processing requests 106 can include the actual image or study to be processed by the algorithm orchestration component 110. In other embodiments, the image processing requests 106 can include metadata that describes relevant attributes/parameters of the image or study and the algorithm orchestration component 110 can be configured to determine whether any workflows are applicable to the image or study initially in response to the request. With these embodiments, the orchestration conductor 112 can receive/retrieve the actual image or study from its source (e.g., PACS, VNA, or the like) if at least one applicable workflow is found. For example, in some implementations, the orchestration conductor component 112 can direct the image provider from which the request was received to provide the image or study in response to a determine that at least one workflow is applicable. Still in other embodiments, the image processing request 106 can include an identifier for an image or study associated with the request that can be used by orchestration conductor component 112 to access the image or study at its stored location. For instance, an image processing request 106 can identify a new study that has been added to a particular provider's PACS and include a request to process the new study. With these embodiments, the orchestration conductor component 112 and/or the workflow execution engine 116 can be configured to access and retrieve the study from the PACS in association with execution of the one or more workflows thereon.

The manner in which an image processing request 106 is received by the algorithm orchestration component 110 can also vary. In some embodiments, an image processing request 106 can be sent from an image provider system/device 102 in response to user input with an application that interfaces with the algorithm orchestration component 110. For example, in some implementations, the application can include a medical image viewer application that provides for accessing and viewing medical images. The viewer application can further be configured to interface with the algorithm orchestration component 110 and provide for submitting an image processing request 106 in association selection of a particular image or imaging study. In some implementations of these embodiments, the image processing request can also include user defined instructions that indicates or identifies what workflow or workflows to be applied to the medical image or imaging study. For example, the request can include information that identifies one or more medical image processing algorithms desired for application to the medical image/imaging study.

In other embodiments, the image provider systems/devices 102 can be configured to push image processing requests 106 to the algorithm orchestration component 110 based on occurrence of one or more events and/or conditions. For example, in some embodiments, the image provider systems/devices 102 can include or be operatively coupled to one or more medical image databases (e.g., PACS) and configured to notify the algorithm orchestration component 110 in response to reception of new images/studies in the one or more medical image databases. In some implementations of these embodiments, the orchestration conductor component 112 can be configured to respond to the notification by processing the newly added image/study using applicable workflows. In this regard, the orchestration conductor component 112 can automatically initiate processing of new images/studies as they are added to the one or more medical image databases of an image provider. The orchestration conductor component 112 can further automatically provide the results and status notifications 108 back to image provider system/device 102.

Figure 3:
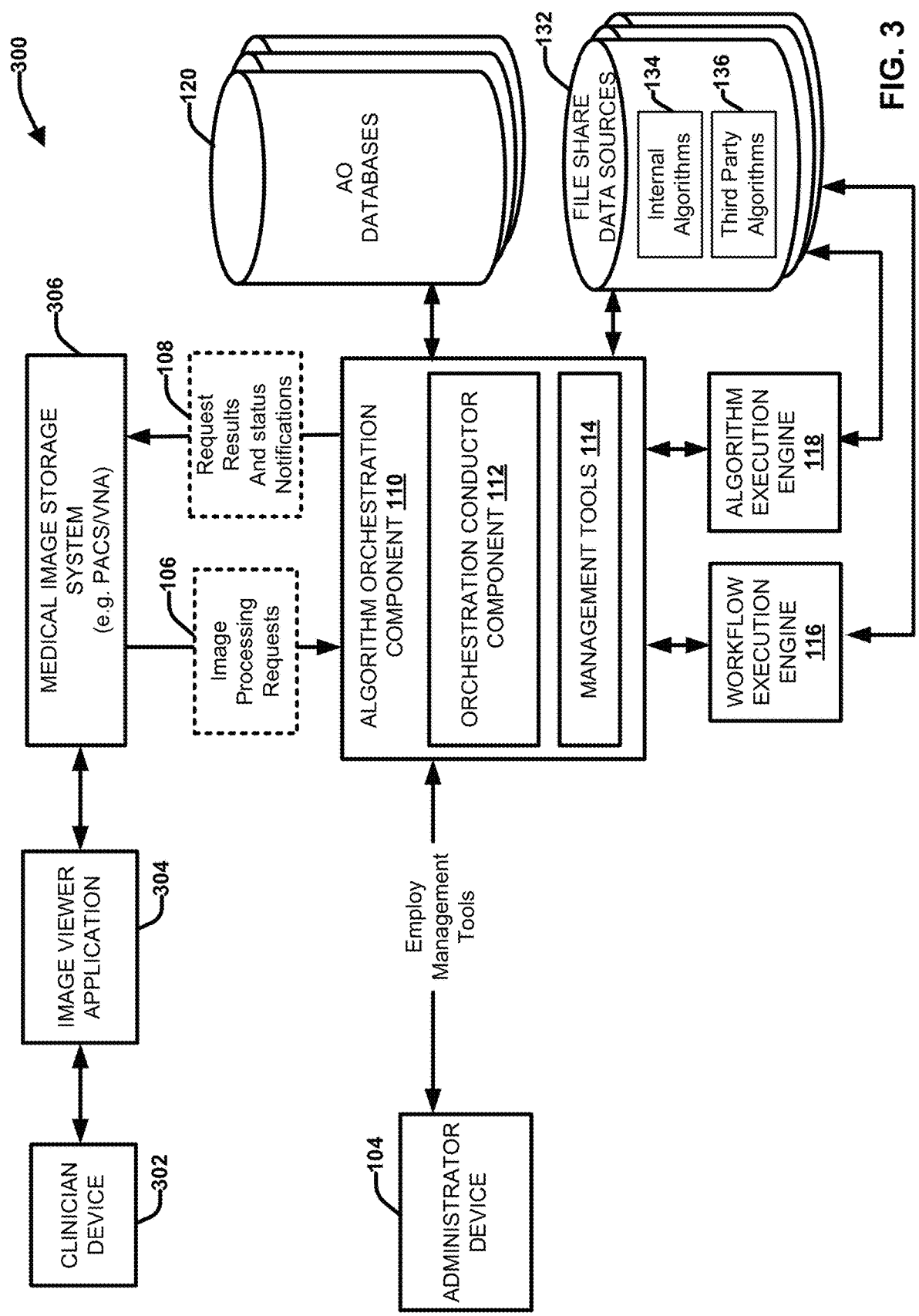
FIG. 3 illustrates a block diagram of another example algorithm orchestration system in accordance with one or more embodiments of the disclosed subject matter.

FIG. 3 illustrates a block diagram of another example algorithm orchestration system 300 in accordance with one or more embodiments of the disclosed subject matter. Repetitive description of like elements employed in respective embodiments is omitted for sake of brevity.

System 300 demonstrates an example embodiment integrating a medical image viewer application 304 and a medical image storage system 306 that can be or correspond to a PACS, a VNA or the like. In accordance with system 300, a clinician can employ a clinician device 302 to access/execute an image viewer application 304 to view medical images stored in the medical image storage system 306. In this regard, the clinician device 302 can include any suitable computing device capable of accessing the viewer application 304 and viewing medical images stored in the medical image storage system 306.

In various embodiment, the image viewer application 304 can provide the image tools needed for viewing and interacting with medical image data stored at the medical image storage system 306. For example, in various embodiments, the image viewer application 304 can be or correspond to medical image view applications/programs that can be accessed using a web-based platform (e.g., a web-application, a client application, or the like). The image viewer application 304 can include software and/or hardware components that facilitate viewing the medical images stored at the medical image storage system 306 and can optionally provide various interactive features for interacting with the images (e.g., changing perspectives, editing the images, applying annotations, etc.). For example, in some implementations, the image viewer application can provide annotation tools for annotating medical images, tools for applying and/or editing DICOM tags, and tools for reviewing/rating the medical images. The image viewer application 304 can also be configured to present the clinician with the request results and status notification 108. In some embodiments, the image viewer application 304 can also provide for receiving user input (e.g., from the clinician such as a radiologist or the like) for initiating/submitting an image processing request 106.

In accordance with system 300, the algorithm orchestration component 110 can interface with the medical image storage system 306 to receive image processing requests 106, retrieve medical image data for the requests, and provide requests results and status notifications 108. Image processing requests 106 can be initiated from the image viewer application 304 and/or the medical image storage system 306. Request results and status notifications 108 can likewise be provided back to the medical image storage system 306 and/or the image viewer application 304.

For example, in one or more embodiments, when a new medical image/image study is received at the medical image storage system 306, the medical image storage system 306 can be configured to send the image processing request 106 as an HTTP request to an API exposed by an API gateway (not shown) for the algorithm orchestration component 110. For example, the image processing request 106 can be identified as a "study processes notification" and can contain the study metadata and the payload. The gateway can be configured to forward the request to the algorithm orchestration conductor component 112 that validates the request payload and assigns the request a unique request ID. In some implementations, the orchestration conductor component 112 can also notify the medical image storage system (and/or the image viewer application 304) that the request has been received and validated. The notification can include the request ID and indicate the current status of the request (e.g., status="request received and validated"). The algorithm orchestration component can then direct the workflow execution engine 116 to invoke all (or one or more) applicable workflows for the image/imaging study. In implementations in which two or more workflows are applicable to the image/image study, the workflow execution engine can execute each workflow as a separate thread.

As exemplified with reference to FIGS. 2A-2C, typical workflows will start by validating the medical image metadata using one or more Decision nodes to determine whether the image satisfies defined workflow requirements (e.g., regarding modality, view position, study description etc.). In accordance with these workflows, if the workflow execution engine 118 determines the image/image study satisfies the workflow requirements, the algorithm orchestration component 110 and/or the workflow execution engine 116 transfers the image/study data from the medical image storage system 306 to a local file storage employed by the algorithm orchestration component 110 (e.g., stored in the one or more AO databases 120). When the transfer is complete, the workflow execution engine 116 executes all algorithms defined in the workflow. In this regard, for each algorithm included in the workflow, the workflow execution engine 116 invokes/calls the algorithm as defined and waits for a response. Once the responses of all the algorithms included in the workflow have been received, the algorithm orchestration component transfers request results 108 the back to the medical image storage system 306 and sends a notification message to the image viewer application 304 notifying the clinician that the processing of the image/study is complete. This notification message can also include information identifying the specific algorithms executed and the results for each algorithm. The requests results 108 can include output files produced by the algorithms which can be viewed/reviewed by the clinician using the image viewer application 304.

With reference to FIGS. 1 and 3, in addition to orchestrating application of AI algorithms to medical images for image providers, the algorithm orchestration component 110 further provides various management tools 114 for administrators. These management tools can include, but are not limited to: tools for onboarding algorithms to be included in the workflows, tools for creating and configuring the workflows, tools for configuring parameters of the algorithms used in the workflows, tools for defining what workflows to apply to incoming image processing requests, and tools for tracking, monitoring and auditing received and processed requests. In the embodiments shown in system 100 and 300, an administrator can access and employ these management tools using an administrator device 104. The administrator device 104 can be or correspond to any suitable computing device capable of accessing the algorithm orchestration component 110 and employing the management tools 114 provided thereby. The features and functionalities of the management tools 114 are described in greater detail infra with reference to FIGS. 5A-16B.

The deployment architecture algorithm orchestration system 100, algorithm orchestration system 300, and other system described herein can vary. In some embodiments, the one or more components, devices, engines, databases, system, or other elements of system 100, system 300 and other system described herein can be deployed in a cloud architecture, a virtualized enterprise architecture, or an enterprise architecture wherein one or more features and functionalities of the algorithm orchestration component 110 are accessed by the client devices/systems (e.g., the image provider systems/devices 102, the administrator device 104, and/or the clinician device 202) via one or more networks using a server/client relationship. Various example deployment architectures for algorithm orchestration system 100 and algorithm orchestration system 300 are described in greater detail infra with reference to FIG. 17, FIGS. 18A-18B and FIGS. 29-32.

Figure 4:
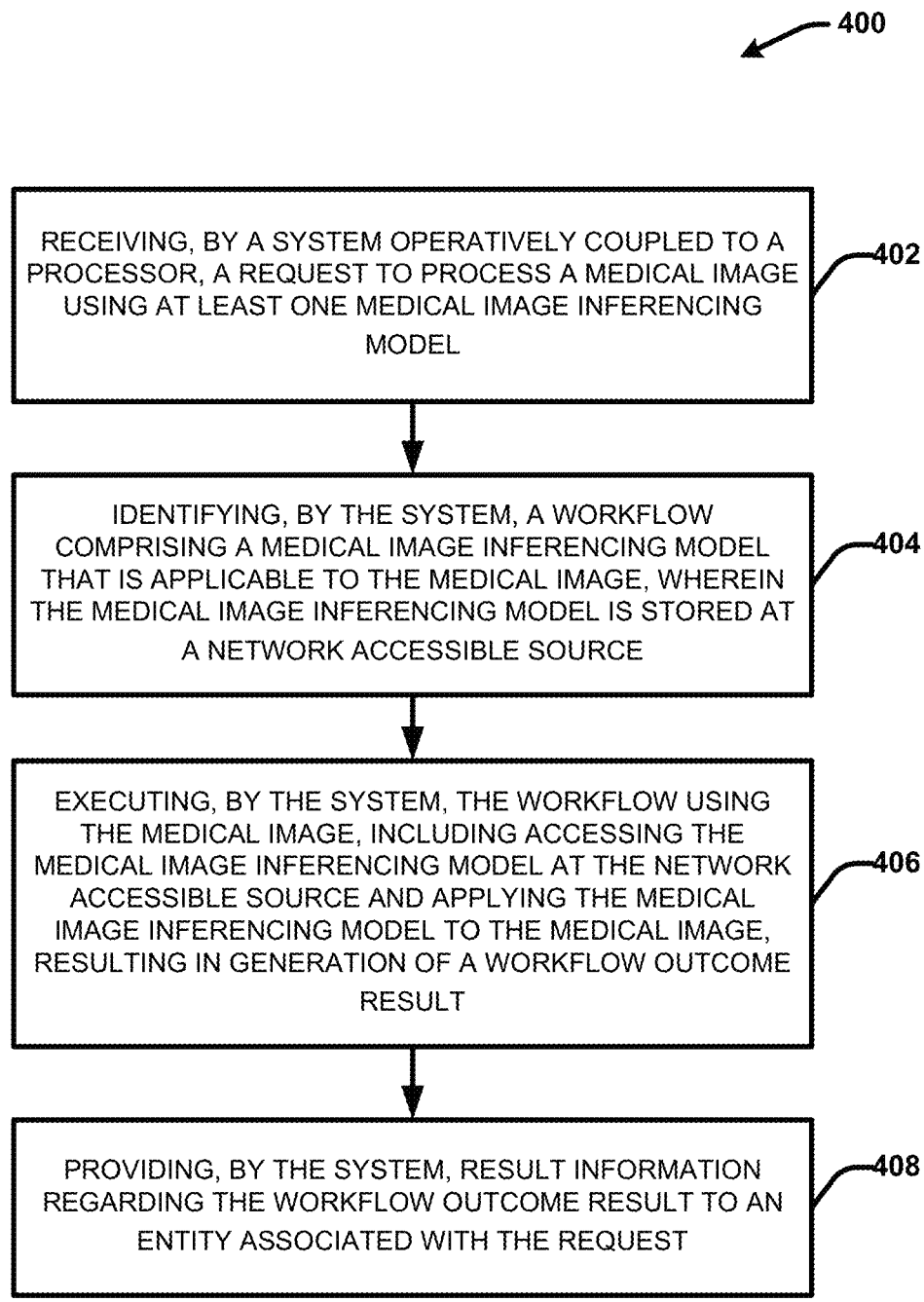
FIG. 4 presents a high-level flow diagram of an example computer implemented method for executing workflow instructions to analyze a medical image and associated metadata in accordance with one or more embodiments of the disclosed subject matter.

FIG. 4 presents a high-level flow diagram of an example computer implemented method 400 for executing workflow instructions to analyze a medical image and associated metadata in accordance with one or more embodiments of the disclosed subject matter. In accordance with method 400, at 402, a system operatively coupled to a processor (e.g., system 100, system 300 and other system described herein), can receive a request (e.g., an image processing request 106) to process a medical image using at least one medical image inferencing models (e.g., one or more of the internal algorithms 134 and/or the external algorithms 136). At 402, the system identifies a workflow comprising a medical image inferencing model that is applicable to the medical image (e.g., using the orchestration conductor component 112), wherein the medical image inferencing model is stored at a network accessible source (e.g., one or more file share data sources 132). For example, the orchestration conductor component 112 can select a workflow included in the workflow and task registry data 124 that is applicable to the medical image based on the image type, modality, body part depicted, etc., and one or more requirements for input images of the workflows). At 406, the system can execute the workflow using the medical image (e.g., using the workflow execution engine 116), including accessing the medical image inferencing model at the network accessible source (e.g., as a web-service and/or a job) and applying the medical image inferencing model to the medical image, resulting in generation of a workflow outcome result (e.g., including results of the inferencing model). At 408, the system can provide result information regarding the workflow outcome result to an entity associated with the request (e.g., the image provider, a radiologist authorized to access and view the image, or the like).

Figure 5A:
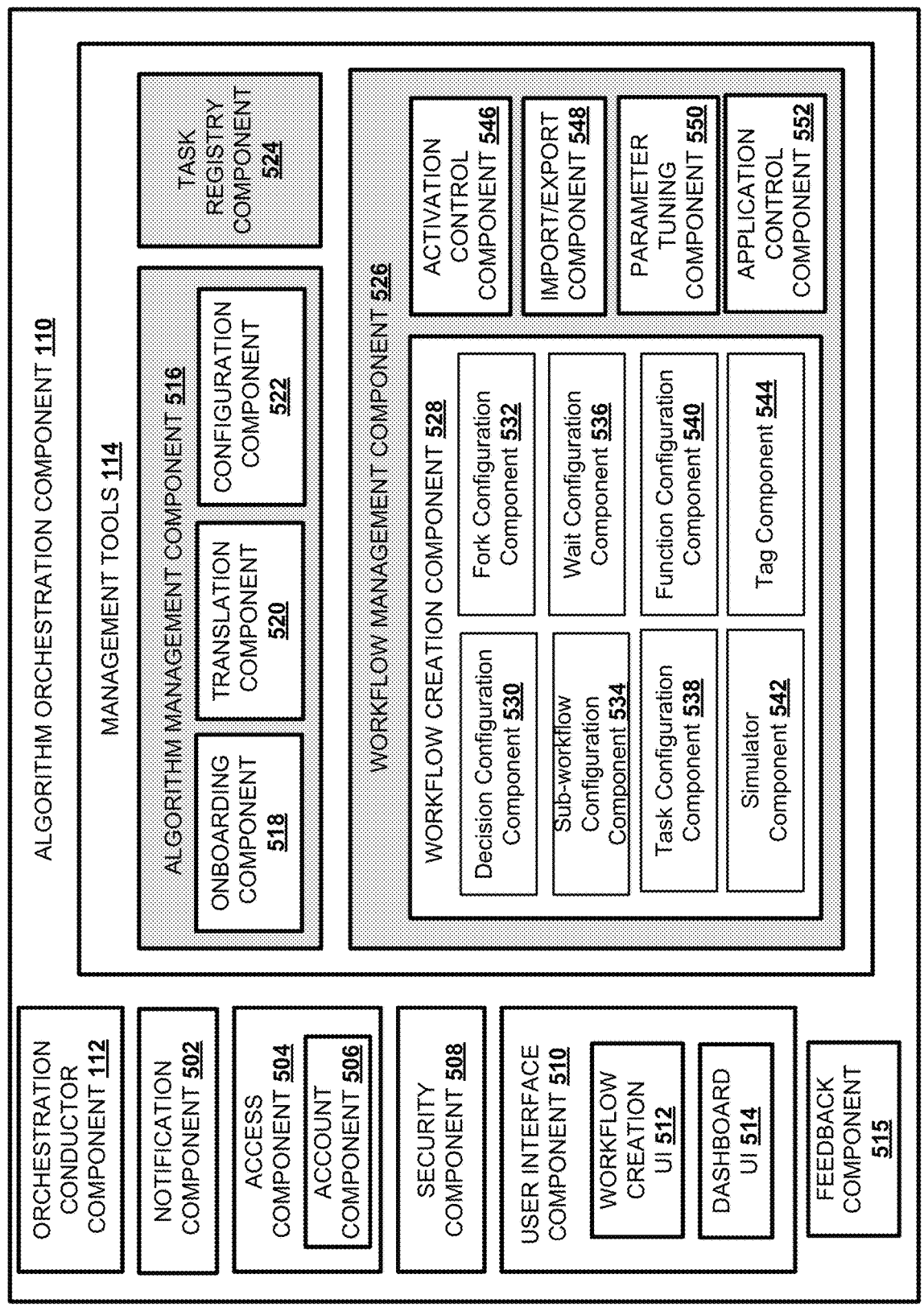
FIGS. 5A-5B provide block diagrams of an example algorithm orchestration component in accordance with one or more embodiments of the disclosed subject matter.
Figure 5B:
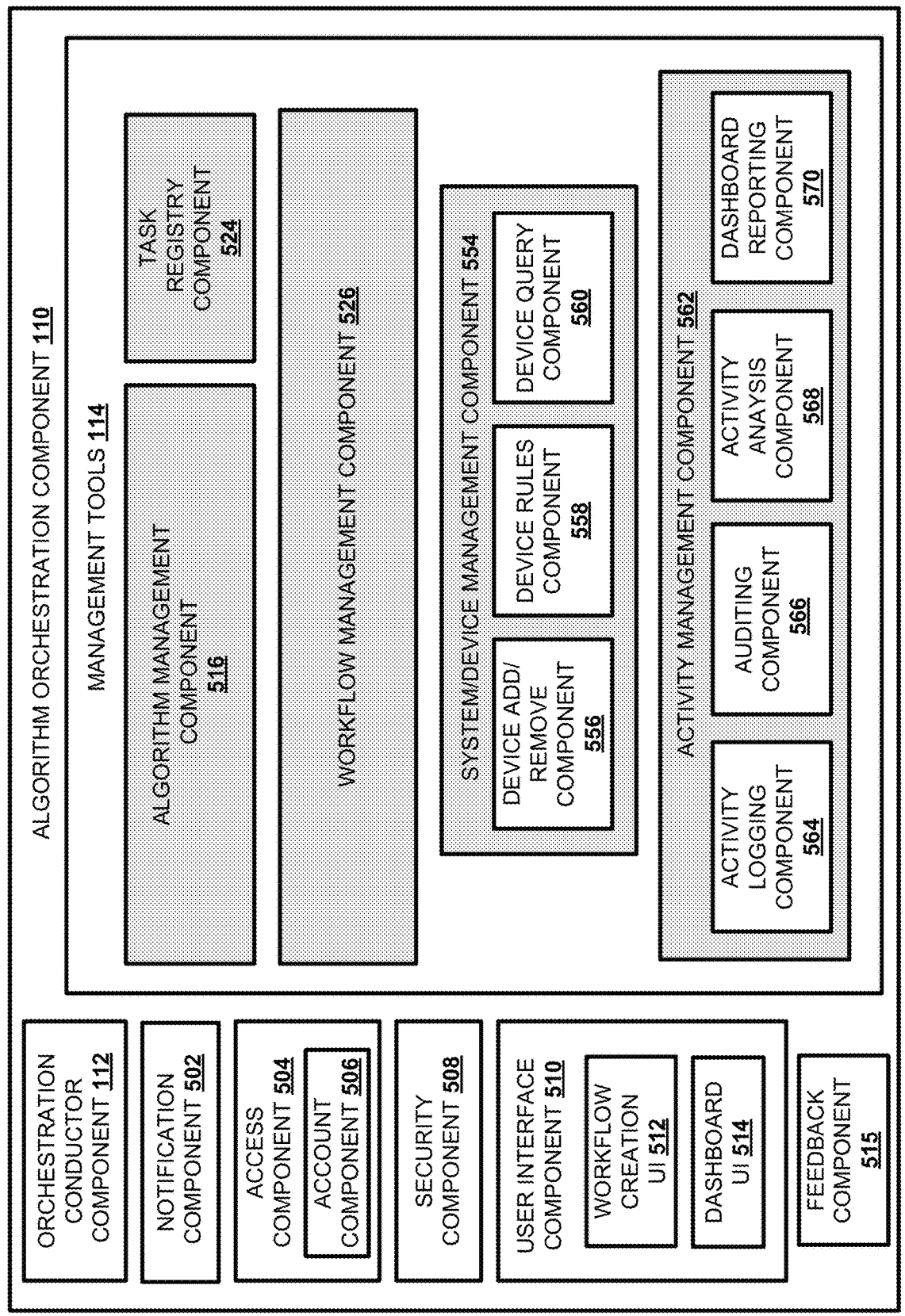

FIGS. 5A-5B provide block diagrams of an example algorithm orchestration component 110 in accordance with one or more embodiments of the disclosed subject matter. Repetitive description of like elements employed in respective embodiments is omitted for sake of brevity.

With reference to FIG. 5A, the algorithm orchestration component 110 can include several computer executable components that respectively provide various computer executable functions described therefor. In the embodiment shown in FIG. 5A, these computer executable components include orchestration conductor component 112, notification component 502, access component 504, security component 508, user interface component 510, feedback component 515, algorithm management comment 516, task registry component 524, and workflow management component 526. The algorithm management comment 516 and the workflow management component 526 further include several sub-components that can respectively be or correspond to computer executable components. In the embodiment shown in FIG. 5B, the management tools 114 can further include a system/device management component 554 and an activity management component 562. It should be appreciated that sub-components of the algorithm management component 516 and the workflow management component 526 are removed in FIG. 5B merely for lack of display space.

The algorithm orchestration component 110 can further include or be operatively coupled to at least one memory (not shown) that stores the computer executable components, and at least one processor (not shown) that executes the computer executable components stored in the memory. Examples of said and memory and processor can be found with reference to FIG. 27, as well as other suitable computer or computing-based elements that can be used in connection with implementing one or more of the systems or components shown and described in connection with FIG. 6 or other figures disclosed herein.

It should be appreciated that various embodiments of the algorithm orchestration component 110 can include subsets of these components shown in FIGS. 5A and 5B. In addition, one or more components of the algorithm orchestration component 110 can be deployed/executed by different devices/machines in a distributed and/or parallel computing environment.

With reference to FIGS. 1, 3, 5A and 5B, in various embodiments the notification component 502 can provide for generating and sending/providing notifications to the image provider system/devices 102 and/or other systems device regarding the activity of the algorithm orchestration component 110. For example, in some embodiments, the notification component 502 can be configured to provide status notification regarding the status of an image processing request 106. For instance, the notification component 502 can provide status notifications indicating if and when an image processing request is received and validated, status notifications regarding whether any workflows and/or algorithms/models are being executed (e.g., workflow/model execution in progress), and status notifications regarding completion of workflows.

The notification component 502 can also be configured to provide notifications regarding whether applicable workflows identified for an image/study associated with an image processing request. For example, in some embodiments, in response to reception of an image processing request 106 to process a medical image, the orchestration conductor component 112 can use metadata describing attributes of the medical image to identify any matching workflows that are applicable to the medical image based on the information included in the workflow and task registry data 122. The notification component 502 can further notify the entity associated with the request regarding the identified applicable workflows. In some implementations, information describing the applicable workflows can also be included in the notification, such as information describing the types of algorithms/models included in the workflows.

The access component 504 and the security component 506 can control access to the algorithm orchestration component 110 by systems, devices and users. For example, as noted above, in some embodiments, the algorithm orchestration component 110 can restrict acceptance of image processing requests 106 to only those systems/devices identified in the system/device task registry data 126. With these embodiments, the security component 508 can control validating image processing request 106 using the system/device task registry data 126 to ensure request from only authorized system/devices are validated. The security component 508 can further define and execute security protocols to be employed by the algorithm orchestration component 110 when exchanging files with other components. This includes how components of the system (e.g., system 100, system 300 or the like) communicate and what type of security credentials are passed for the respective communications to proceed.

The access component 504 and/or the security component 508 can also control access and usage of the management tools 114 by authorized users. Users that employ the management tools are generally referred to herein as "administrators." In this regard, the management tools 114 are designed to be used by administrators of the system (e.g., system 100, system 300 and the like) to manage, control and track usage of the algorithms and workflows by imaging providers. The management tools can also be used by workflow developers to create and edit workflows and algorithms.

The feedback component 515 can facilitate receiving feedback from imaging providers, clinicians (e.g., radiologists, experts, etc.) regarding the workflow results. For example, in various embodiments, the workflow orchestration component 110 can present the workflow results to clinicians via an image viewer application (e.g., image viewer application 304 or the like) that can also include a mechanism for providing feedback from one or more entities (reviewers) regarding the inferencing model results. For example, in some implementation, the viewer application can provide a review prompt with one or more defined review questions regarding the model outputs that can be answered with predefined selectable response options and/or open text. The review questions can vary depending for the respective inferencing models. In one or more embodiments, the review questions can include at least one question regarding the accuracy of the model outputs. For example, the review questions can ask the user to provide binary feedback stating whether the inference results are correct or incorrect. In another example, the review questions can ask the user to rate the accuracy of the model results using a defined rating/scoring scale. In some embodiments, the viewer application can also provide a mechanism for reviews to provide feedback regarding identified errors in the inference results and/or corrections to the errors. Any feedback collected from the reviewers can be provided back to the feedback component 515 and used to evaluate and monitor model performance (e.g., via the activity management component 562).

In various embodiments, the algorithm orchestration component 110 can provide the management tools 114 via network accessible platform, such as a web-application, a mobile application, or the like. In other implementations, the algorithm orchestration component 110 can provide the management tools 114 as a management native application. Regardless of the deployment platform used for the management tools 114, the access component 504 can control access to some or all of the management tools 114 to authorized users. With these embodiments, the access component 504 can include an account component 506 that can store information identifying authorized users and their account access information required for the respective authorized users to access the management tools (e.g., username and password or the like).

Figure 6:
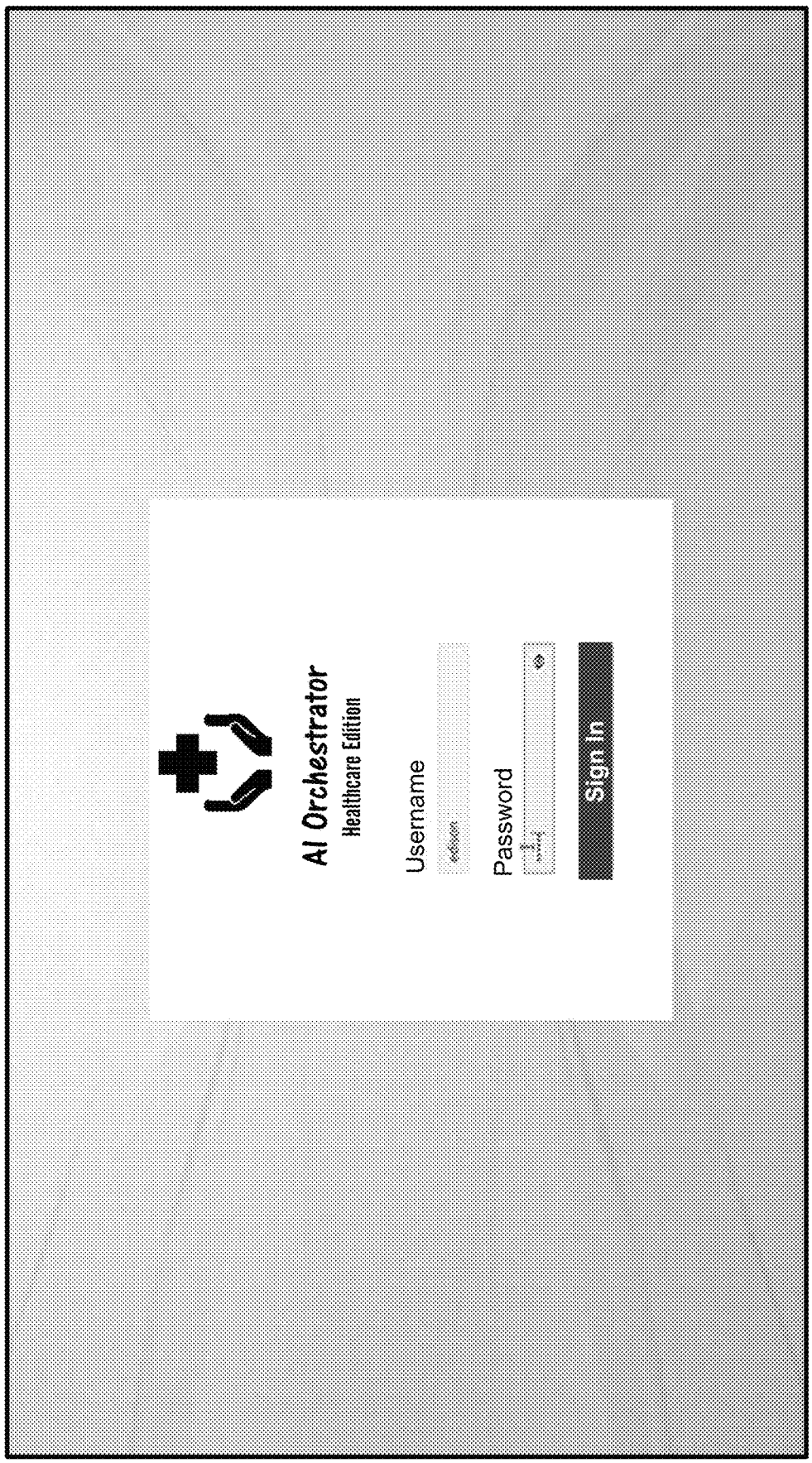
FIG. 6 presents an example administration login page for accessing an algorithm orchestration management application in accordance with one or more embodiments of the disclosed subject matter.

For example, FIG. 6 presents an example administration login page for accessing an algorithm orchestration management application in accordance with one or more embodiments of the disclosed subject matter. The algorithm orchestration management application is referred to herein as "AI orchestrator". In the embodiment shown, in order to access the AI orchestrator, a user must sign in with their correct account information (e.g. username and password).

In some embodiments, the access component 504 can apply usage restrictions regarding usage of certain features and functionalities of the system based on individual permissions granted to certain user accounts based on their identity, role, account status, authority, and the like. For example, in some embodiments, the access component 504 can manage and/or control usage of certain management tools and features, such algorithm parameter adjusting capabilities, workflow creation capabilities and the like, based on authorizations/restrictions associated with respective user accounts.

The algorithm orchestration component 110 can include user interface component 110 to facilitate generating and providing various UIs of the algorithm management application, whether it be a web-based platform (e.g., a web application, a mobile application, or the like), or a native application. Several example UIs that can be generated and provided by the user interface component 510 are presented in FIGS. 7-16B. The UIs presented in FIGS. 7A-16B demonstrate various feature and functionalities of the management tools 114, including features and functionalities of the algorithm management component 516, the task registry component 524, the system/device management component 554, and the activity management component 562. Details regarding these UIs are described with reference to their corresponding components.

In this regard, the algorithm management component 516 can provide various management functions related to the algorithms that are used in the workflows, including of viewing existing algorithms, onboarding algorithms, editing an algorithm, searching an algorithm, and deleting an algorithm. In various embodiments, the algorithm management component 516 can provide an authorized administrator (e.g., after successful login), with access to the algorithm catalog data 124. The algorithm management component 516 can also provide tools for searching and filtering algorithms included in the algorithm catalog data 122 by various criteria associated therewith as included in the catalog data. For example, in various embodiments, the respective algorithms included in the algorithm catalog data can include information identifying or describing the type of the algorithm, the function of the algorithm, the input image criteria (e.g., patient parameters, modality, image attributes regarding quality, orientation, etc.), the provider, the version, the most recent update time, the creator, and the like. Any of these factors can be used to search and filer the algorithms included in the catalog. The algorithm management component 516 can further provide tools for adding algorithms, as well as removing, transferring (e.g., from one file location to another), configuring, and editing the algorithms. To facilitate this end algorithm management component 516 can include onboarding component 518, translation component 520 and configuration component 522.

In one or more embodiments, the onboarding component 518 provides an onboarding function for onboarding algorithms to the system for inclusion in the algorithm catalog data 124. In this context, onboarding refers to loading or adding the information execution information needed to access and execute an algorithm (e.g., an AI model) into the algorithm catalog. In various implementations, only algorithms that have been onboarded and added to the algorithm catalog data 124 can be integrated into workflows and applied to medical images by the algorithm orchestration component (e.g., using the workflow execution engine 116 and/or the algorithm execution engine 118). The onboarding component 518 provides for onboarding both internal algorithms 134 and third-party algorithms 136.

The translation component 520 provides a translation function for translating algorithm formats in association with algorithm onboarding so that they are compatible with the format used by the algorithm orchestration component 510. This is typically used for third-party algorithms. In particular, if an algorithm to be onboarded is written (e.g., coded), stored, or accessed/run in a different format than that used by the algorithm orchestration component 510, the workflow execution engine 116 and/or the algorithm execution engine 118 will not be able to access and run the algorithm properly. The translation component 520 can perform a mapping between the format used by the algorithm orchestration component 510 and the format used by the third-party algorithm (or any algorithm to be onboarded that is written in a different format) and stores this mapping with the algorithm information in the algorithm catalog data 122. For example, the translation component 520 can create a mapping between the API used by the algorithm execution engine 118 and the API used by the third-party provider. In some embodiments, the translation component 520 can automatically create the mapping for an algorithm from its third-party format to the format employed by the algorithm orchestration component 110 when the algorithm is onboarded based on a determination that its native format is not the format employed by the algorithm orchestration component 510. The translation component 520 can further automatically store the translation/mapping information with the onboarded algorithm in the algorithm catalog data 122 for use by the algorithm execution engine 118.

The configuration component 522 provides for configuring one or more parameters and/or parameter values of the algorithms that are included in the algorithm catalog data. For example, the configuration component 522 can be used to set/adjust threshold parameters, including threshold for criticality or priority, clinical relevance, diagnostic thresholds, probability thresholds, confidence score thresholds, and the like. For instance, with respect to diagnostic models, the configuration comment 522 can allow an administrator to set/adjust the confidence score threshold of the model for classifying a positive or negative diagnosis. The configuration component 522 can also provide for setting/adjusting model input image parameters that control requirements of the input images that the model can be applied to.

In some embodiments, the configuration component 522 can also provide for setting/adjusting rules/instructions regarding the criticality or priority of a model. In this regard, the algorithm/models can provide different AI solutions for different cases. Some models may be used for trauma cases (e.g., detecting a brain lead) which have higher level of urgency relative to a routing follow-up or a longer-term analysis (e.g., evaluating a knee injury using a knee segmentation model). With these embodiments, the criticality or priority level of a model can control the order of application of the model to received images in the image processing requests, wherein the workflow execution engine 116 and/or the algorithm execution engine 118 can be configured to execute higher priority models (and/or workflows including higher priority models) before lower priority models (and/or workflows including lower priority models). For example, in some implementations, when a new image processing request 106 is received (e.g., as pushed from a PACS, at the request of a clinician, or the like), the orchestration conductor component 112 can identify all applicable workflows for the medical image/study associated with the request. The orchestration conductor component 112 can further direct the workflow execution engine 116 to execute the workflows in order based on the priority/criticality of the algorithms included in the workflows. In this regard, the orchestration conductor component 112 can direct the workflow execution engine to perform workflows including a high priority algorithm (e.g., relative to a defined threshold) before a workflow that does not include a high priority algorithm.

In various embodiments, the configuration component 522 can store any changes to an algorithm's parameters with the algorithm information in the workflow and task registry data 122 with information identifying the date/time in which the update to the model was made and the administrator that applied the update. In some implementations, the configuration component 522 can generate a new version of a model or algorithm in response to a change/adjustment to the models' parameters. With these implementations, any updates/changes to a model's parameters can results in creation of a new version of the model with the new parameters and the previous version can be maintained in the algorithm catalog data 124.

FIG. 7 presents an example algorithm management user interface UI 701 in accordance with one or more embodiments of the disclosed subject matter. In some embodiments, the algorithm management UI 701 can be presented in response to selection of the algorithms tab from the upper toolbar. In this example implementation, algorithm management user interface UI 700 can provide searchable/filterable list of algorithms included in the algorithm catalog data 124. The algorithm list can provide some high-level information for each algorithm, including the display name (i.e., the name/identifier used for the algorithm), the date when it was last updated, the provider, and the version. In this example and other examples presented herein, the provider is either "internal" or "third-party." It should be appreciated that the third-party providers can be further specified to identify the specific third party being referred to. In addition, the internal provider can be more specifically identified (e.g., by name, location, etc.). In various embodiments, algorithms included in the list can be selected to view more detailed information for the algorithm and to configure/edit parameters for the algorithm. The algorithm management user interface UI 701 also provides access to an algorithm onboarding function (e.g., via clicking/selecting the onboard algorithm icon 702) and access to an algorithm editing function (e.g., via clicking/selecting the algorithm editor icon 704).

Figure 8:
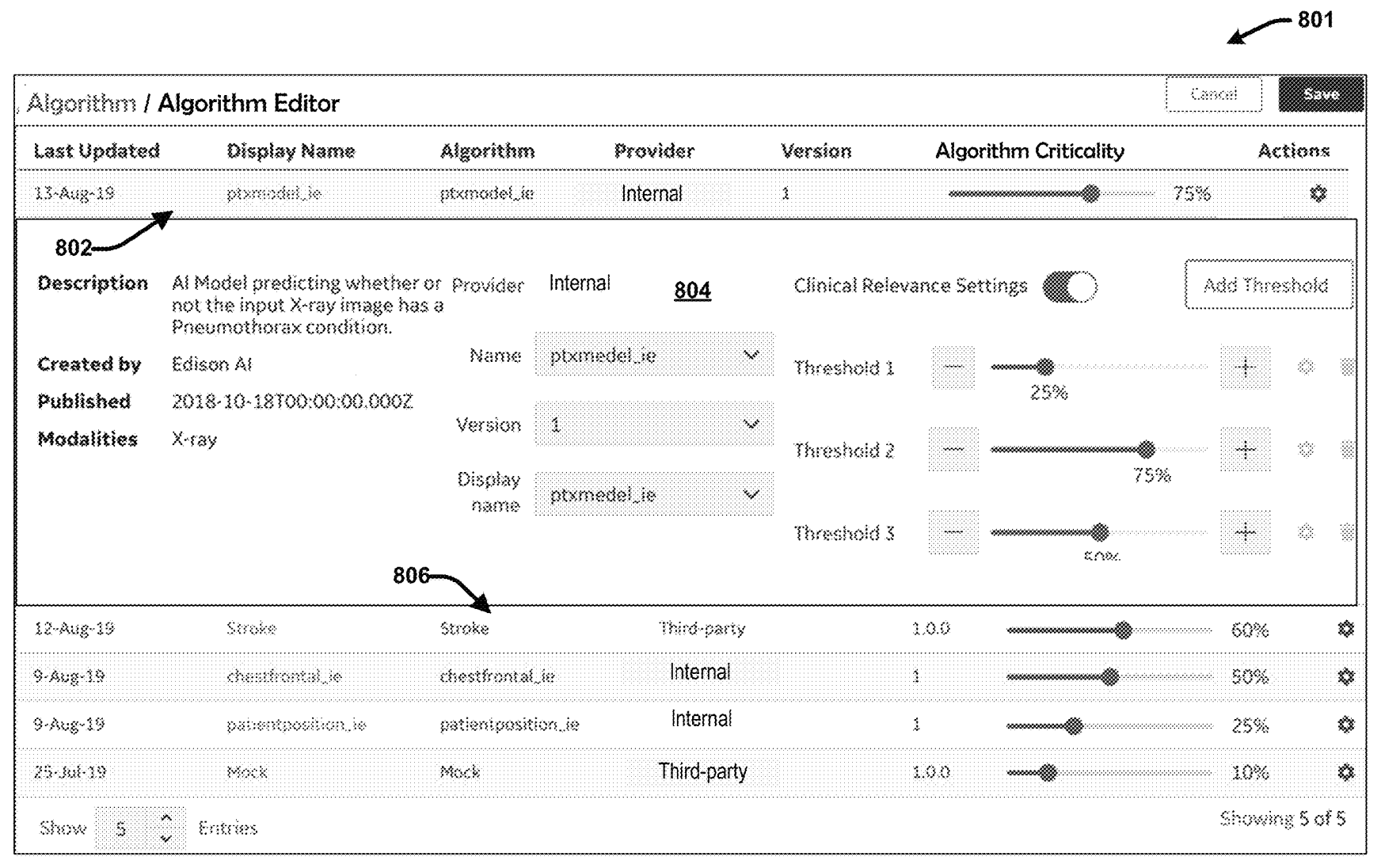

FIG. 8 presents an example algorithm management editor UI 801 in accordance with one or more embodiments of the disclosed subject matter. In some implementations, the algorithm editor UI 801 can be displayed in response to selection of a specific algorithm from the list view of the algorithm management UI 701 in association with a request to edit the algorithm (e.g., via selecting the algorithm editor icon 704).

The algorithm management editor UI 801 provides an example interface to operate the configuration component 522 to configure or adjust one or more parameters of an algorithm. In the embodiment shown, five algorithms are displayed and an editor window 804 is opened for a selected algorithm from the list, which this example is the first algorithm 802 in the list. The remaining four algorithms are listed below the editor window, as indicated by reference arrow 806. Each of the five algorithms presented including information identifying the latest update date, the display name, the algorithm type (e.g., PTX, stroke, chest frontal, patient position, and mock), the provider, the version, and the algorithm criticality (or priority). An algorithm criticality slider is provided for the respective algorithms in the list to adjust the criticality given to the selected algorithm. Actions can be initiated directly from the algorithm editor UI 801 for each algorithm including, including deleting the algorithm and removing it from the algorithm catalog data 122.

The editor window 804 provides some additional detailed information for the selected algorithm, including a description of the model, the creator, the publication date, and the modalities supported. Threshold settings applicable to a given model are further presented that can be adjusted via the UI. For example, the thresholds can include a probability threshold for detecting a given condition (e.g., stroke, patient position) related to the model analysis of a given image and/or image metadata. The editor window also provides for setting a clinical relevance threshold related to the model analysis of a given image and/or image metadata. It should be appreciated that parameters and threshold available for editing shown in the algorithm management editor UI 801 are merely exemplary and that various other parameters and thresholds can be adjusted which can vary from model to model.

Figure 9A:
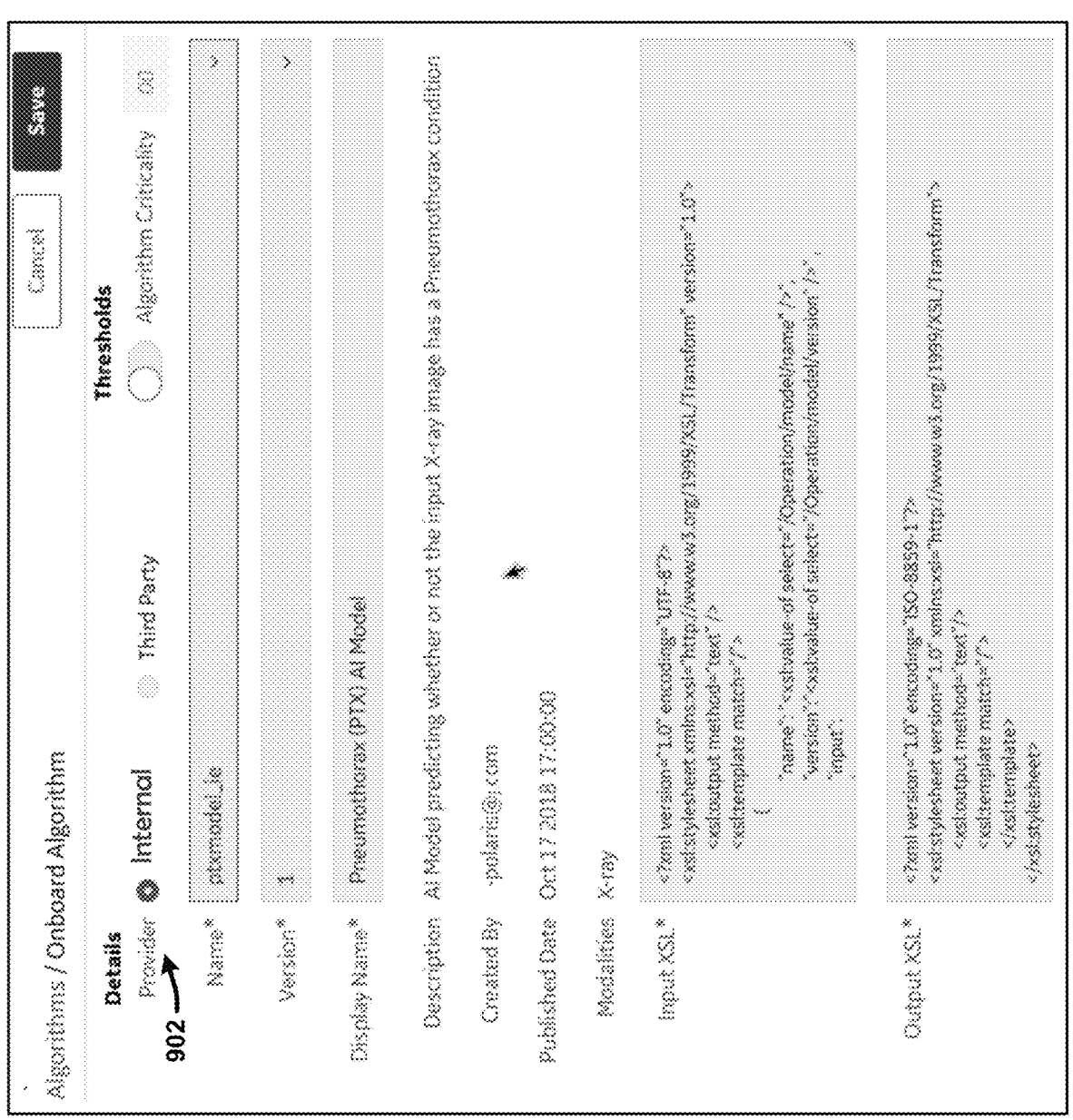

FIGS. 9A-9B presents an example algorithm onboarding UI 901 in accordance with one or more embodiments of the disclosed subject matter. In various embodiment, the algorithm onboarding UI 901 can be presented in response to selection of the algorithm onboarding icon 702 from the algorithm management UI 701. The algorithm onboarding UI 901 provides an example interface to operate the algorithm onboarding component 518 and the translation component 520. In accordance with this example implementation, the onboarding component 901 can provide for onboarding an internal algorithm and a third-party algorithm via selectin the corresponding provider via the provider button 902. FIG. 9A demonstrates onboarding an internal algorithm (e.g., that is an algorithm provided by the same entity that owns/manages the algorithm orchestration component 110) and FIG. 9B demonstrates onboarding a third-party algorithm.

With reference to FIG. 9A, the algorithm onboarding UI 901 provides several data fields for receiving administrator input in association with onboarding an internal algorithm, including receiving input identifying the algorithm name, the version, the display name, the input format and the output format. In one or more embodiments, in response to selecting "internal" as the provider, the onboarding component 520 interfaces with an internal index of algorithms that are accessible to the algorithm orchestration component 110. For example, this index of algorithms can be different from the algorithm catalog data 122 and include a larger set of algorithms developed internally from which internal algorithms can be selected for onboarding into the algorithm catalog data 122. With these embodiments, the algorithm name and version can be selected from a drop-down list that provides all (or a filter subset) of the algorithms included in the index. On selecting the required algorithm name, the algorithm onboarding component 518 can fetch and import (e.g., from the algorithm index) the algorithms details into the remaining data fields. For example, the onboarding component 518 can fetch and import the details regarding the description, the creator, the creation date, the last update date, the input XSL field, and the output XSL field. The algorithm onboarding UI 901 also provides an option to add a unique name for the algorithm display name as preferred by the administrator.

The algorithm onboarding UI 901 can also provide some configuration functions for configuring one or more parameters and thresholds for the algorithm. For example, in the embodiment shown, the algorithm onboarding UI 901 provides for receiving input setting the criticality of the algorithm to be onboarded. Other algorithm parameters and/or thresholds could also be added to the UI for configuring at the time of onboarding. After the algorithm information is entered into the corresponding data fields, selection of the "save" icon can result in onboarding the algorithm into the algorithm catalog data 122 (e.g., via the onboarding component 518).

With reference to FIG. 5B, the third-party algorithm onboarding process can vary from the internal algorithm process slightly. In particular, the third-party algorithm onboarding process requires receiving input identifying the model route, which corresponds to the accessible location/route for accessing the third-party model. In some embodiments, third-party providers from which models can be onboarded can be predefined and the routes to their models/algorithms can be selected from a drop-down menu in the route field. With these implementations, one or more of the algorithm information data fields can be auto populated in response to selection of an algorithm route and/or name from the drop-down menu.

The algorithm onboarding UI 901 further provides for editing the input and output format for the algorithm. For example, in various embodiments, the administrator can provide input changing the input and/or output data formats desired for the third-party algorithm in the input XSL and the output XSL data fields. In response to input changing the format here, the translation component 520 can create a mapping from the API that the third-party to the API supported by the algorithm orchestration component 110 in association with saving and onboarding the algorithm. In this regard, via the algorithm onboarding UI 901, an administrator can edit the input format (e.g., via the input XSL field) to define an input transformation to convert the available metadata in the expected input format for an algorithm (e.g., via the translation component 520). An administrator can also edit the output format (e.g., via the output XSL field) to define an output transformation to convert (e.g., via the translation component 520) the response from the algorithm to a standard format used by algorithm orchestration component 110. In this regard, based on the defined input and output formats provided for an algorithm, the translation component 520 can translate the algorithm format from a first format that is not compatible with the algorithm execution engine to a second format that is compatible with the algorithm execution engine (e.g., wherein the second format is compatible with an API employed by the algorithm execution engine).

With reference again to FIG. 5A, the workflow management component 526 provides various functions related to managing, creating and editing workflows. To facilitate this end, the workflow management component 526 can include workflow creation component 528, activation control component 546, import/export component 548, parameter tuning component 550, and application control component 522.

In various embodiments, the workflow management component 526 can provide an authorized administrator (e.g., after successful login), with access to workflow and task registry data 122. For example, the workflow management component 526 can provide for viewing existing workflows, including detailed information about each workflow, such as information regarding the algorithms included therein, criteria of the medical images to which it is applicable, the creator, the creation date/time, and the like. The activation control component 546 can provide a workflow activation and deactivation function in association with accessing and viewing existing workflows. In particular, the activation control component can allow a user to provide input activating and deactivating workflows. The activation control component 546 can further activate or deactivate a workflow accordingly. In this regard, when a workflow has been deactivated (in response to reception of user input deactivating the workflow), the activation control component 546 can change its status to being deactivated in the workflow and task registry data 122. When a workflow has been deactivated, the workflow will become unavailable for execution by the workflow execution engine 116. Likewise, when a workflow has been activated (in response to reception of user input activating the workflow), the activation control component 546 can change its status to being activated in the workflow and task registry data 122. Only activated workflows will be available for execution by the workflow execution engine 116.

The import/export component 548 can provide for importing and exporting workflows. In this regard, the import/export component 548 can receive workflow files stored at another location and add them to the workflow and task registry data 122. Likewise, the import/export component 548 can export or transfer a workflow file to a selected destination location for execution by another system.

The parameter running component 550 can provide same or similar features and functionalities as the configuration comment 522. In this regard, the parameter tuning component 550 can provide for adjusting parameters and/or threshold of algorithms included in a workflow. Additionally, or alternatively, the parameter tuning component 550 can provide for editing and/or adjusting parameters of other nodes included in the workflow. For example, the parameter tuning component 550 can provide for editing/adjusting parameters of decision nodes, and function nodes.

The application control component 552 can provide for receiving user input defining one or more conditions that control execution/application of a workflow by the workflow execution component 116. Information defining workflow execution conditions can further be associated with the workflow in the workflow and task registry data 122 and employed by the orchestration conductor component 112 and/or the workflow execution engine 116 to control execution/application of the workflow accordingly. For example, in some implementations, the application control component 552 can allow a user to define input image criterion regarding the input images for which the workflow is applicable. The workflow execution conditions can relate to the imaging provider from which an image or study is received (e.g., only apply this workflow for imaging provider 1 and imaging provider 3), timing (e.g., don't apply this workflow during peak hours), system load (e.g., don't apply this workflow when the system load exceeds X %), other workflows being run, workflow priority, and the like.

The workflow creation component 528 can provide a workflow creation application or program via which developers can create and edit workflows. The user interface component 510 can further provide a workflow creation UI 512 via which a user can access and employ the features and functionalities of the workflow creation component 528. The workflow creation component 528 includes several component that respectively provide different features and functionalities for creating and configuring workflow, including a decision configuration component 530, a fork configuration component 532, a sub-workflow configuration component 534, a wait configuration component 536, a task configuration component 538, a function configuration component 540, a simulator component 542 and a tag component 544. The workflow creation component 528 and its sub-components are discussed in greater detail with reference to FIGS. 11A-12D.

Figure 10B:
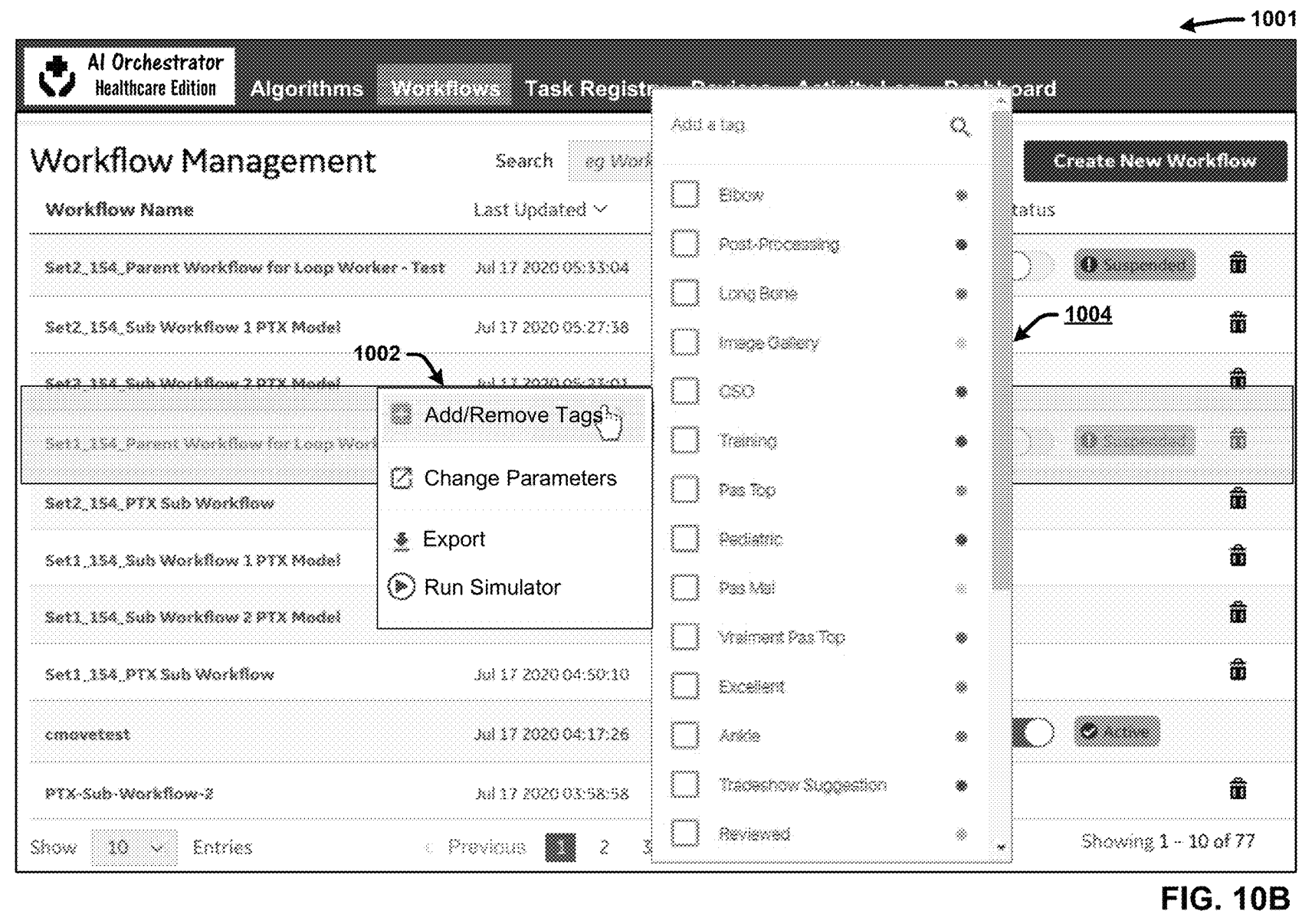

FIGS. 10A-10B present an example workflow management UI 1001 in accordance with one or more embodiments of the disclosed subject matter. In various embodiments, the workflow management UI 1001 can be generated and presented in response to selection of the "Workflows" tab from the upper toolbar. As shown in FIG. 10A, the workflow management UI can provide a searchable and filterable list of available workflows and sub-workflows (e.g., wherein sub-workflows are only run when their parent workflows are run). The list view can identify the workflow/sub-workflow by name, the time when the workflow/sub-workflow was last updated, the type (e.g., workflow or sub-workflow), the creator, and the status (e.g., activated/active or deactivated/suspended). In the embodiment shown, three workflows are displayed, two being disabled and one being active. The workflow management UI 1001 provides a status adjustment button for workflows that can be used to activate and reactive (or suspend) workflows directly from the UI.

In various embodiments, workflows and sub-workflows can be selected from the list to view additional details about the workflow/sub-workflow, to edit the workflow, delete the workflow and/or perform other actions related to the workflow. For example, as shown in FIG. 10B, in some implementations, right clicking on a workflow or sub-workflow from the list can result in generation of a pop-up window 1002 with various actions/functions that can be selected and performed relevant to the workflow, including adding or removing tags, changing parameters, exporting the workflow or running the workflow simulator (as described below). In this example, selection of the add or remove tags function can result in generation of a tag pop-up window 1004 with a selectable list of tags that can be added or removed from the workflow. The workflow management UI 1001 further provides a workflow creation button ("Create New Workflow") that can be selected to open the workflow creation application/feature provided by the workflow creation component 528.

Figure 11A:
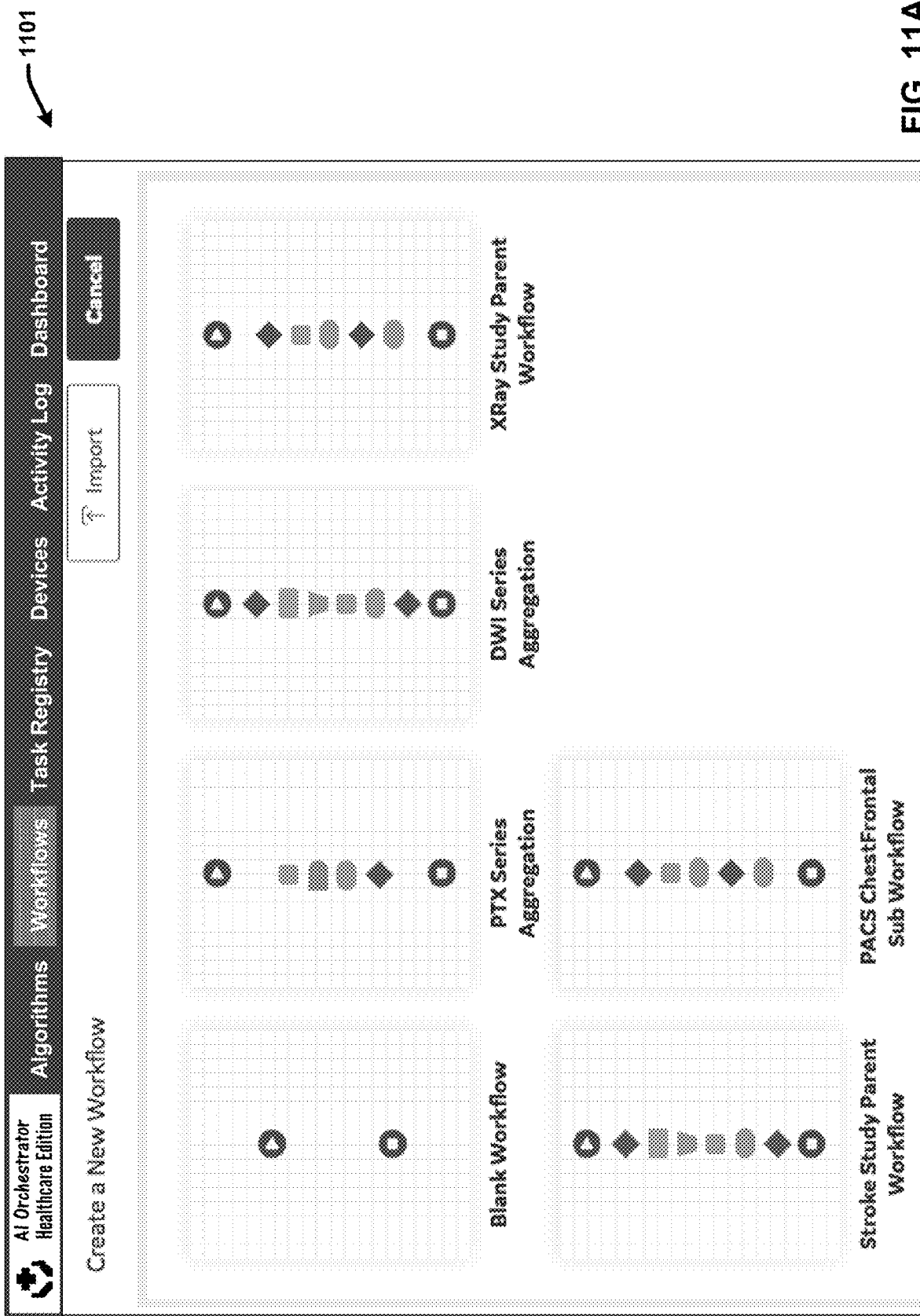
FIGS. 11A-11X present example UIs of a workflow creation application in association with usage of the workflow creation application to create a workflow in with one or more embodiments of the disclosed subject matter.
Figure 11B:
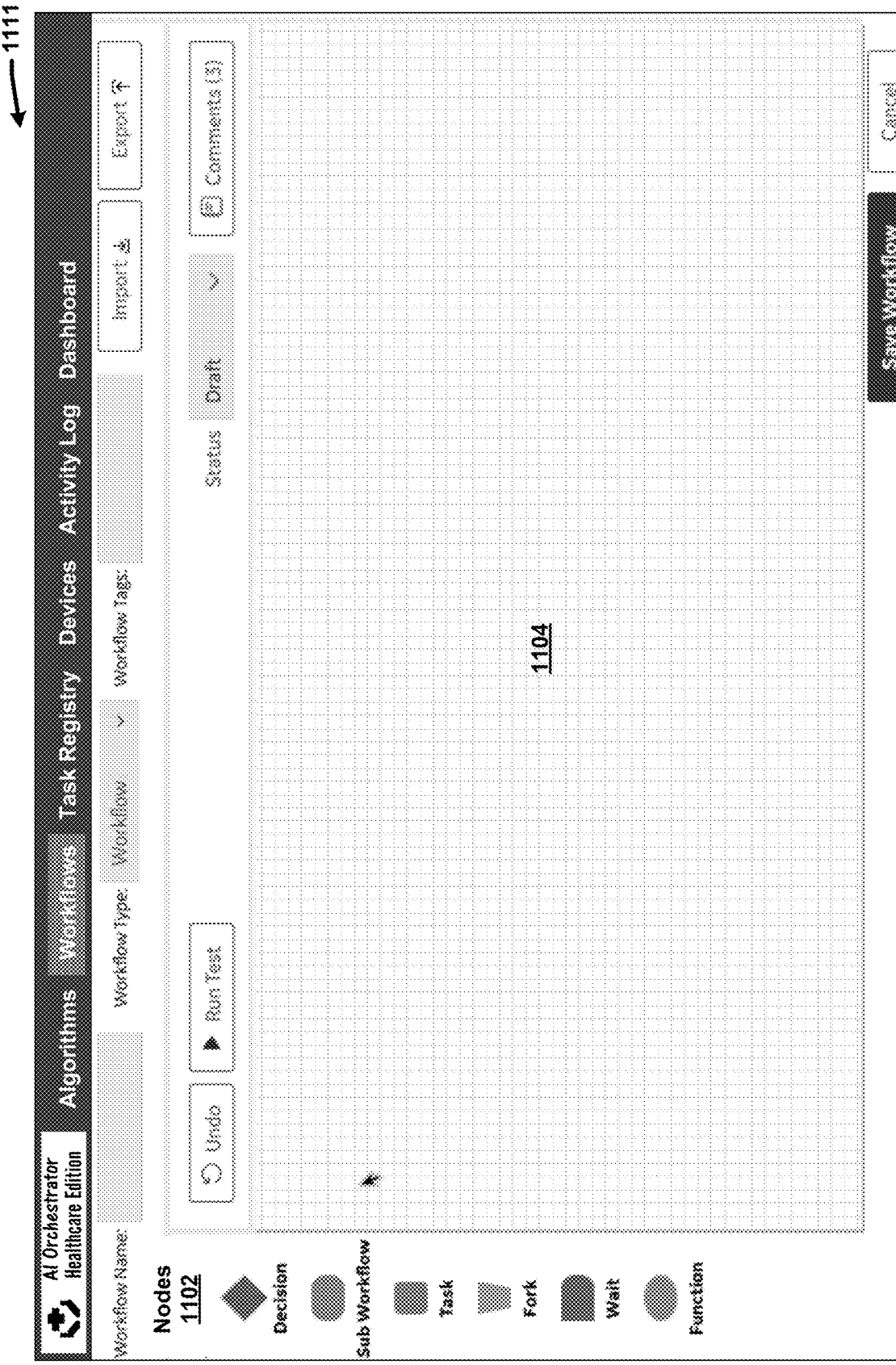
Figure 11C:
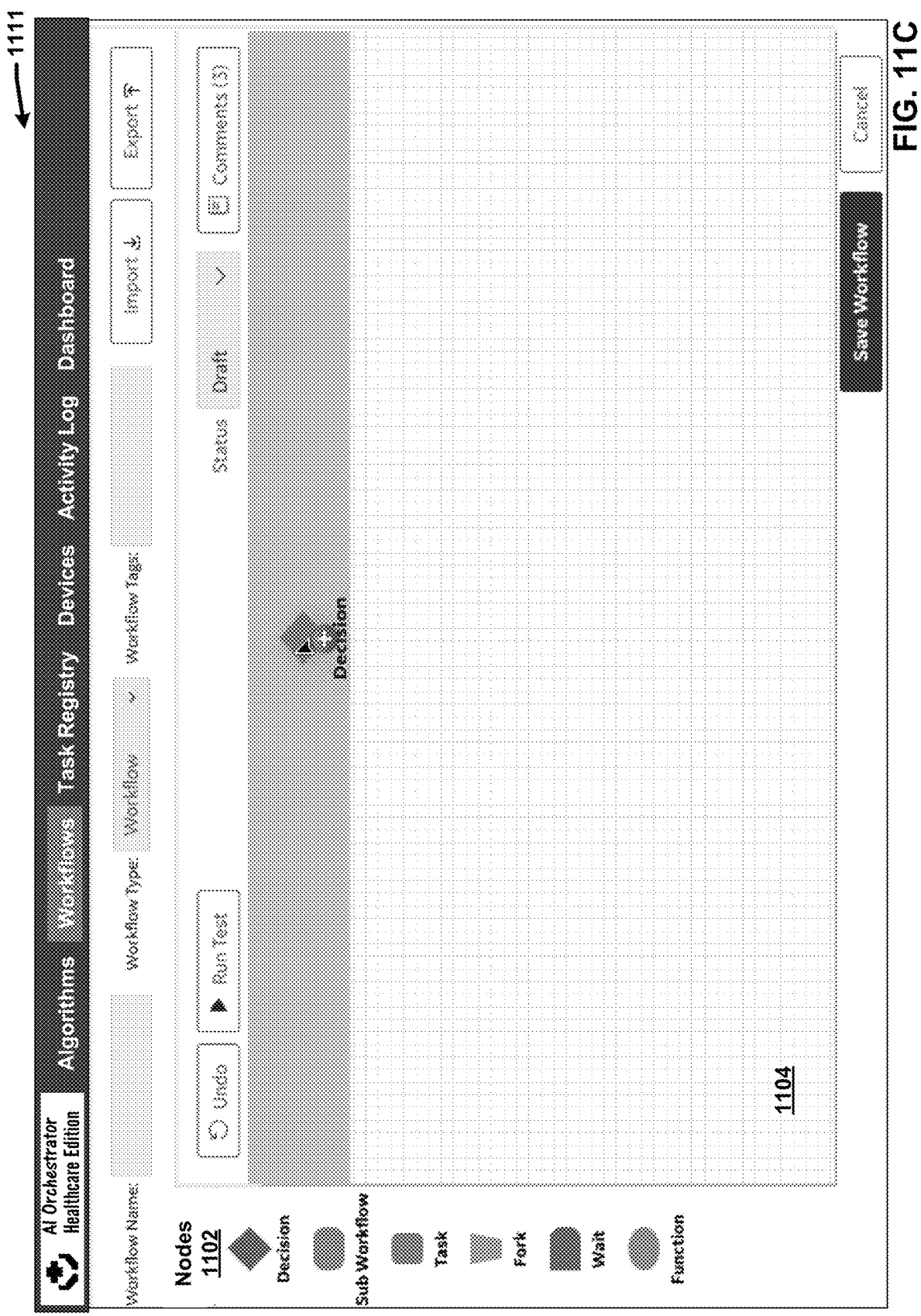
Figure 11D:
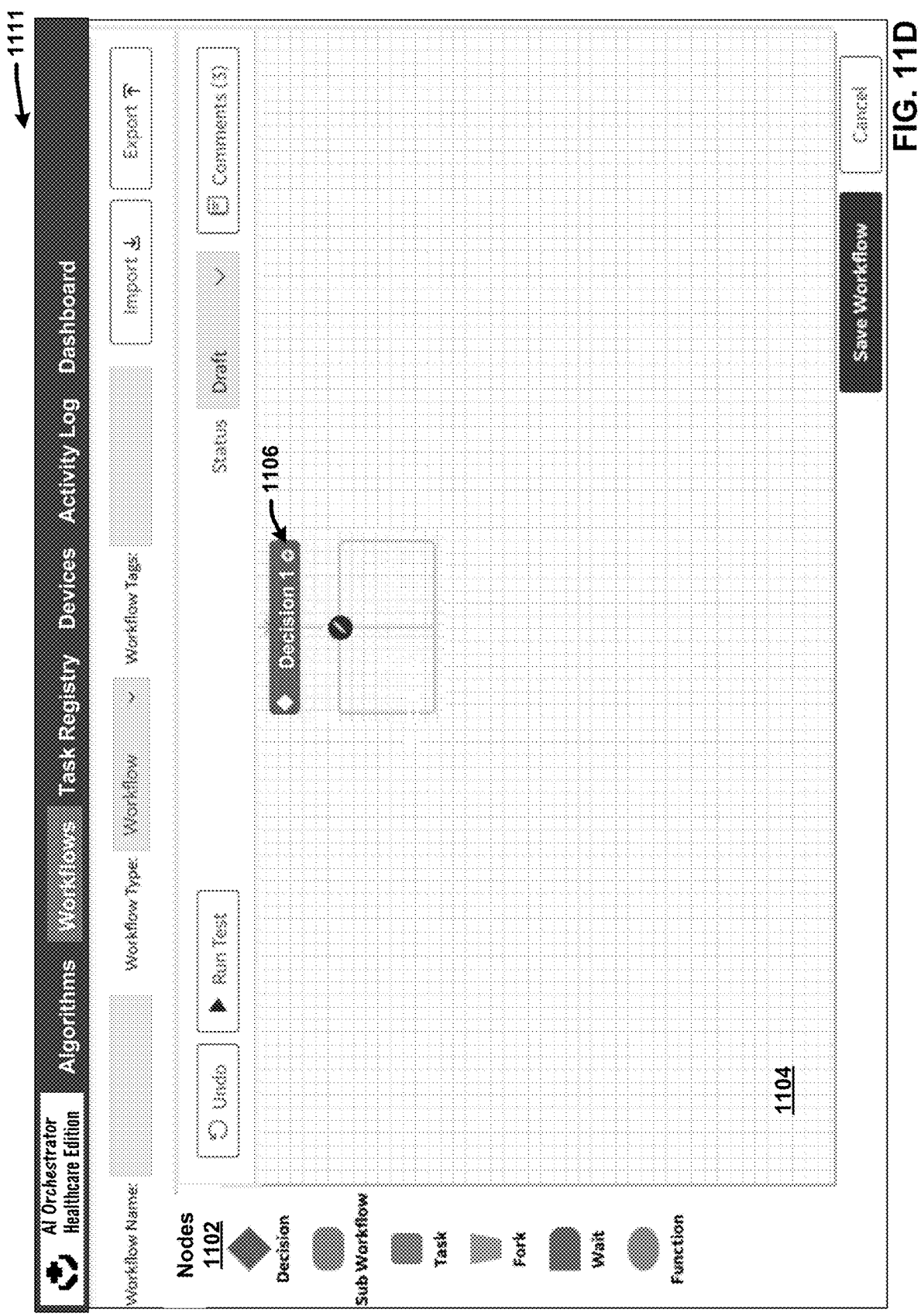
Figure 11E:
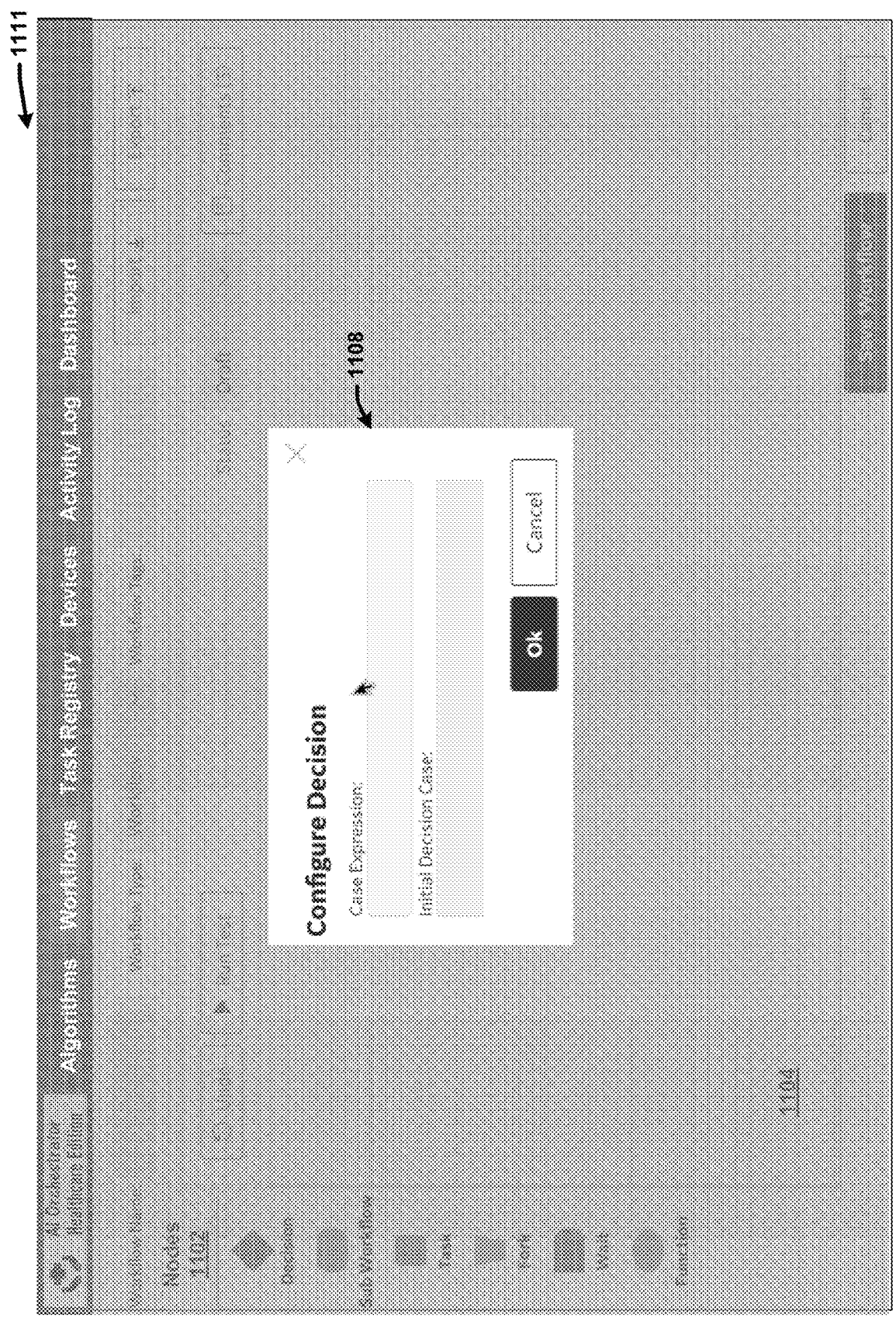
Figure 11F:
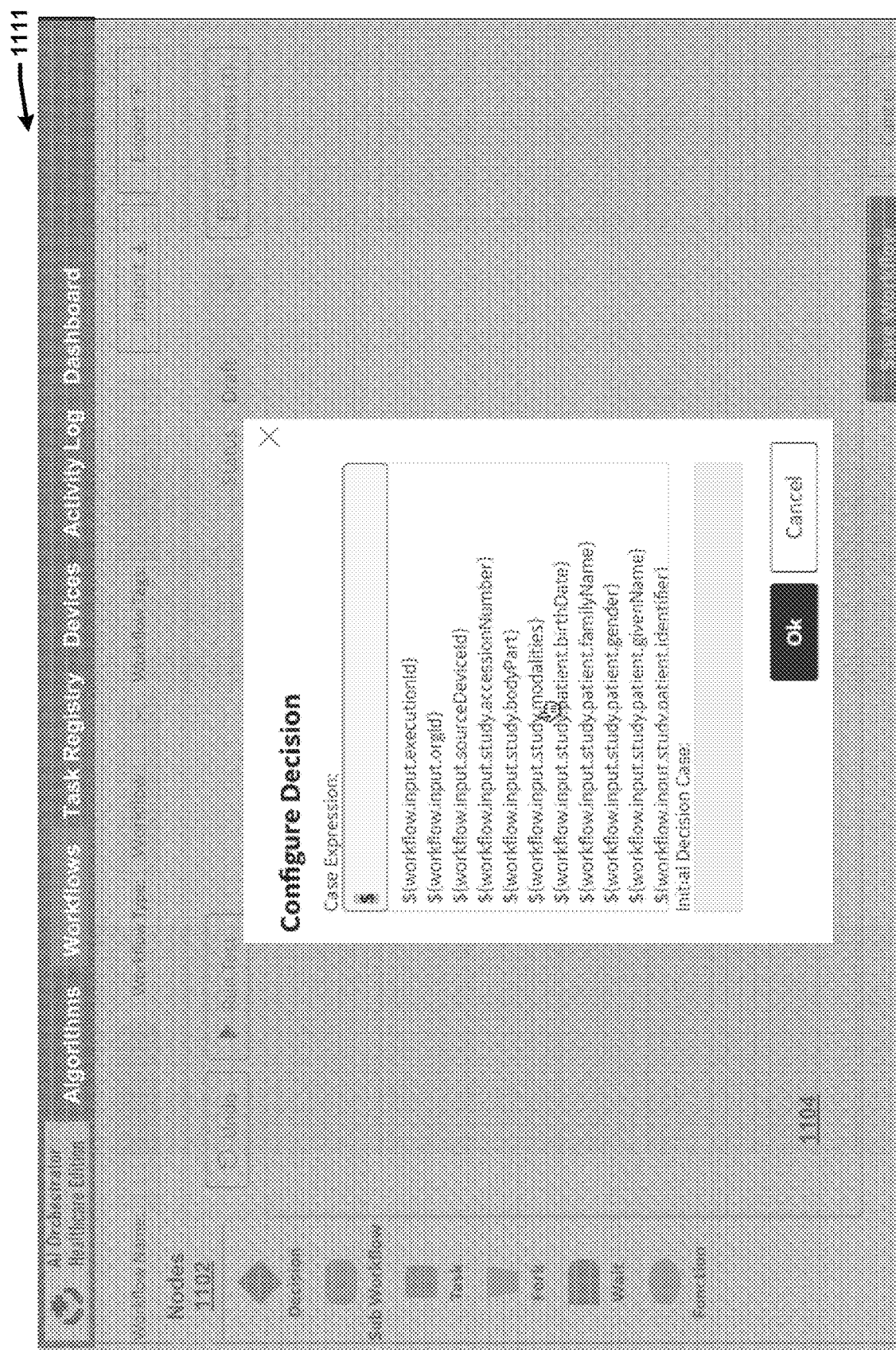
Figure 11G:
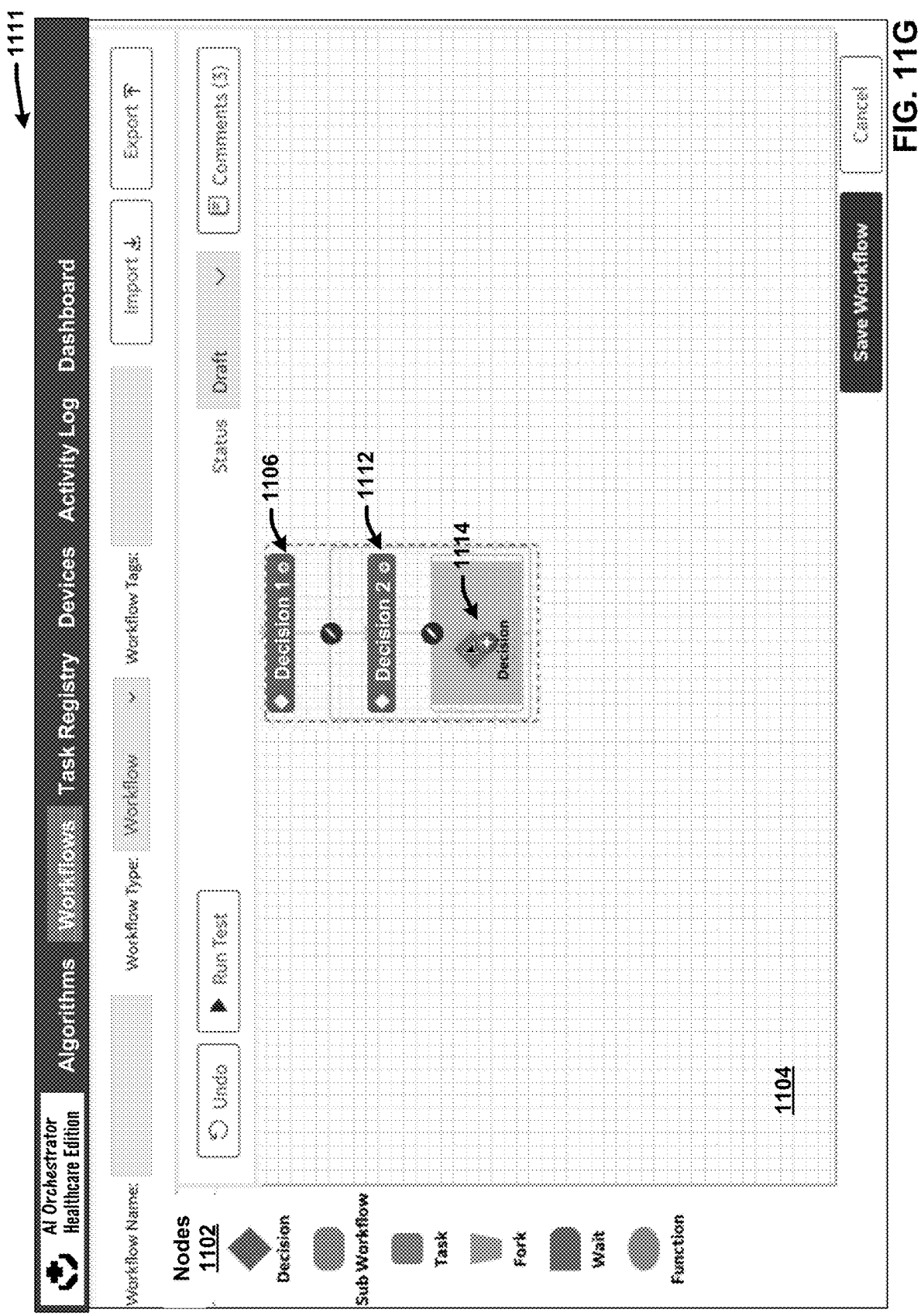
Figure 11H:
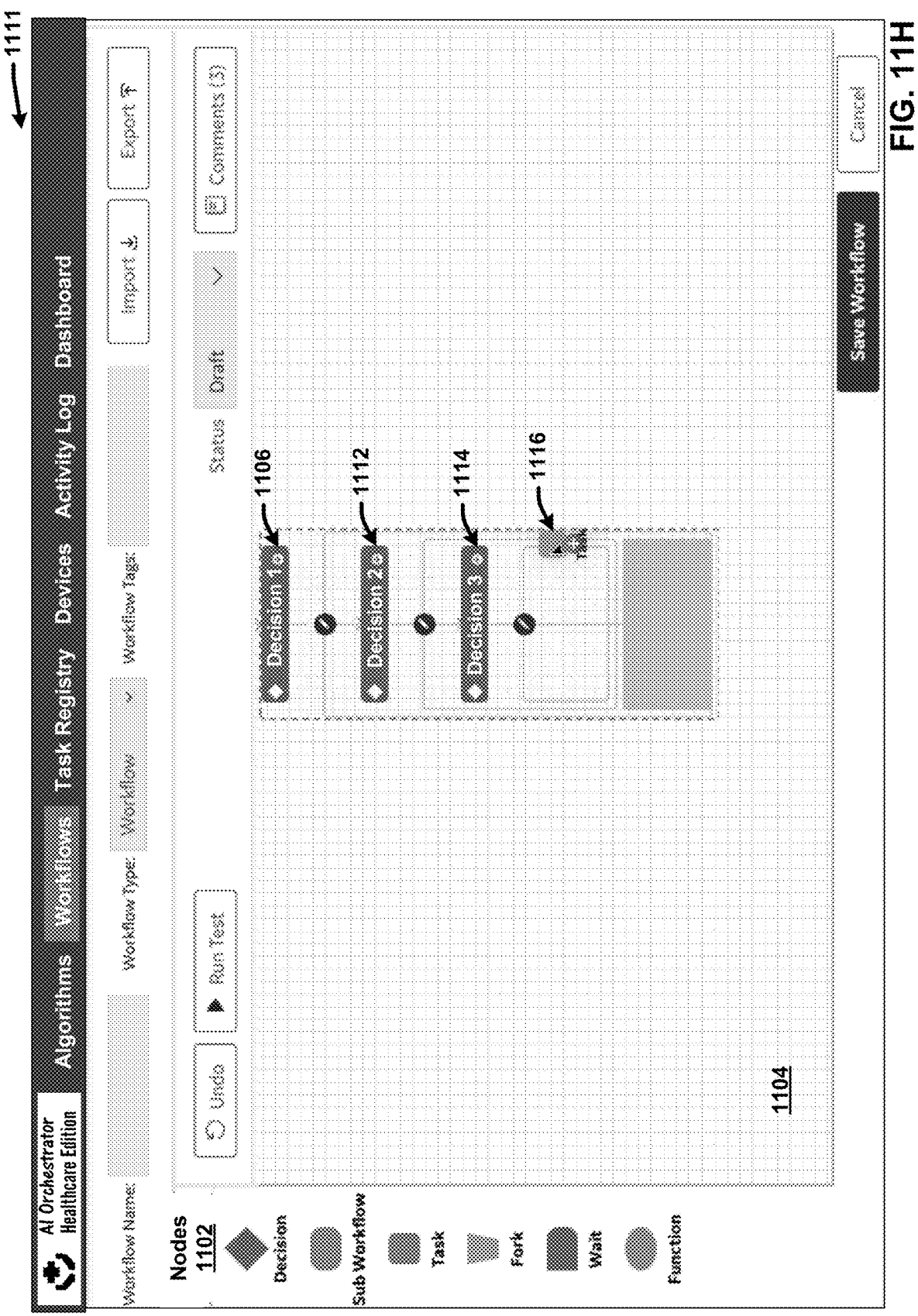
Figure 11I:
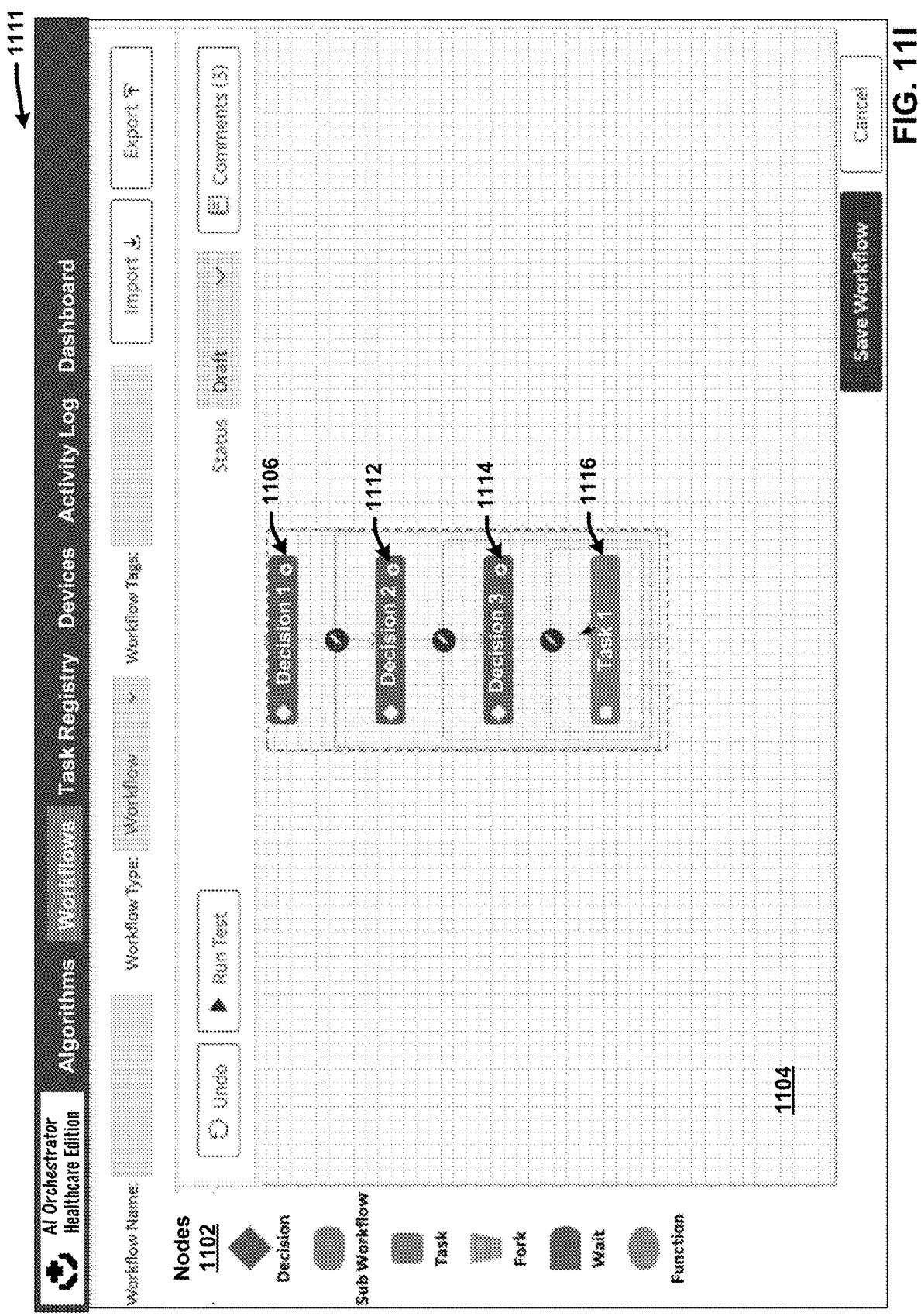
Figure 11J:
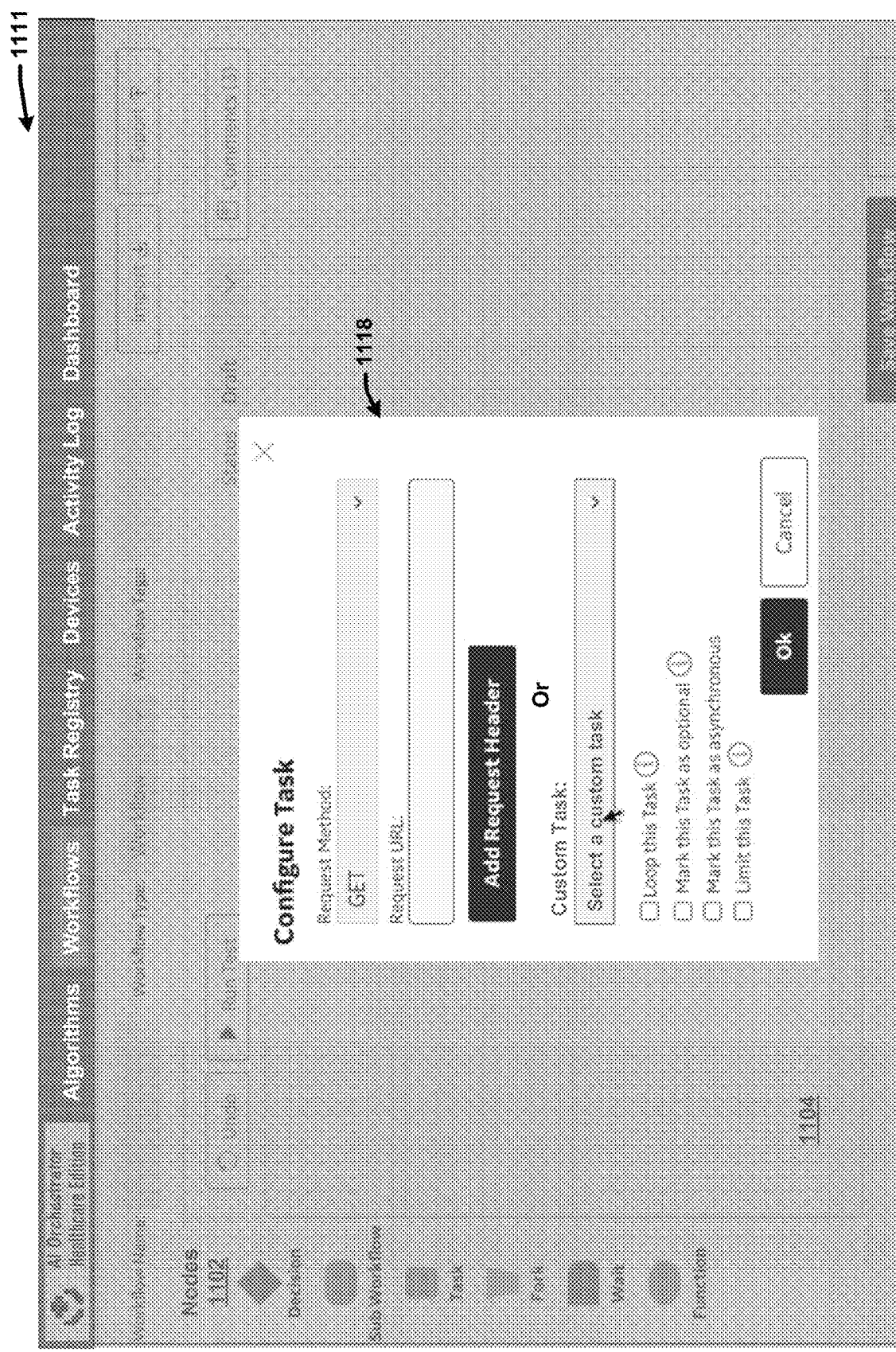
Figure 11K:
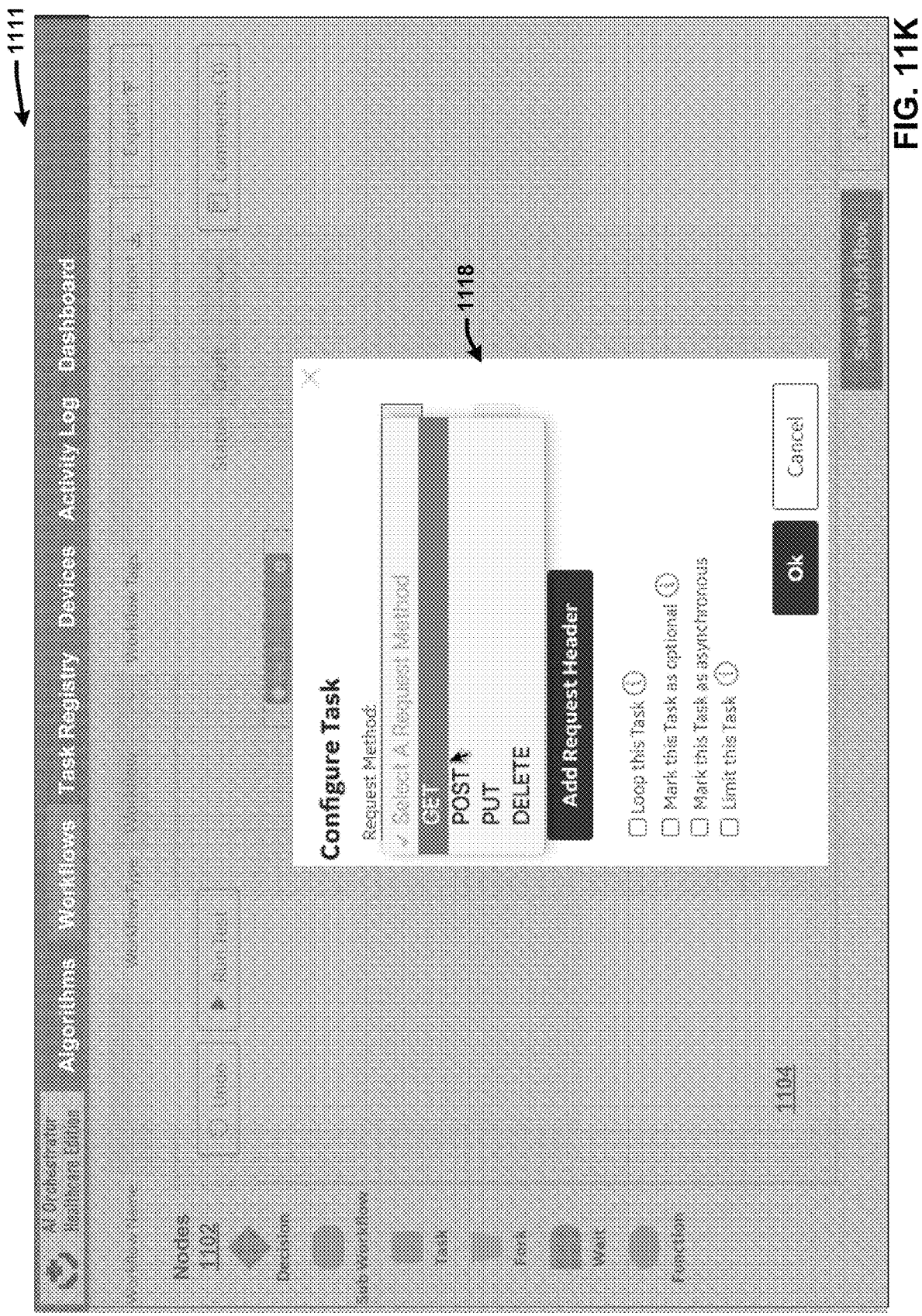
Figure 11M:
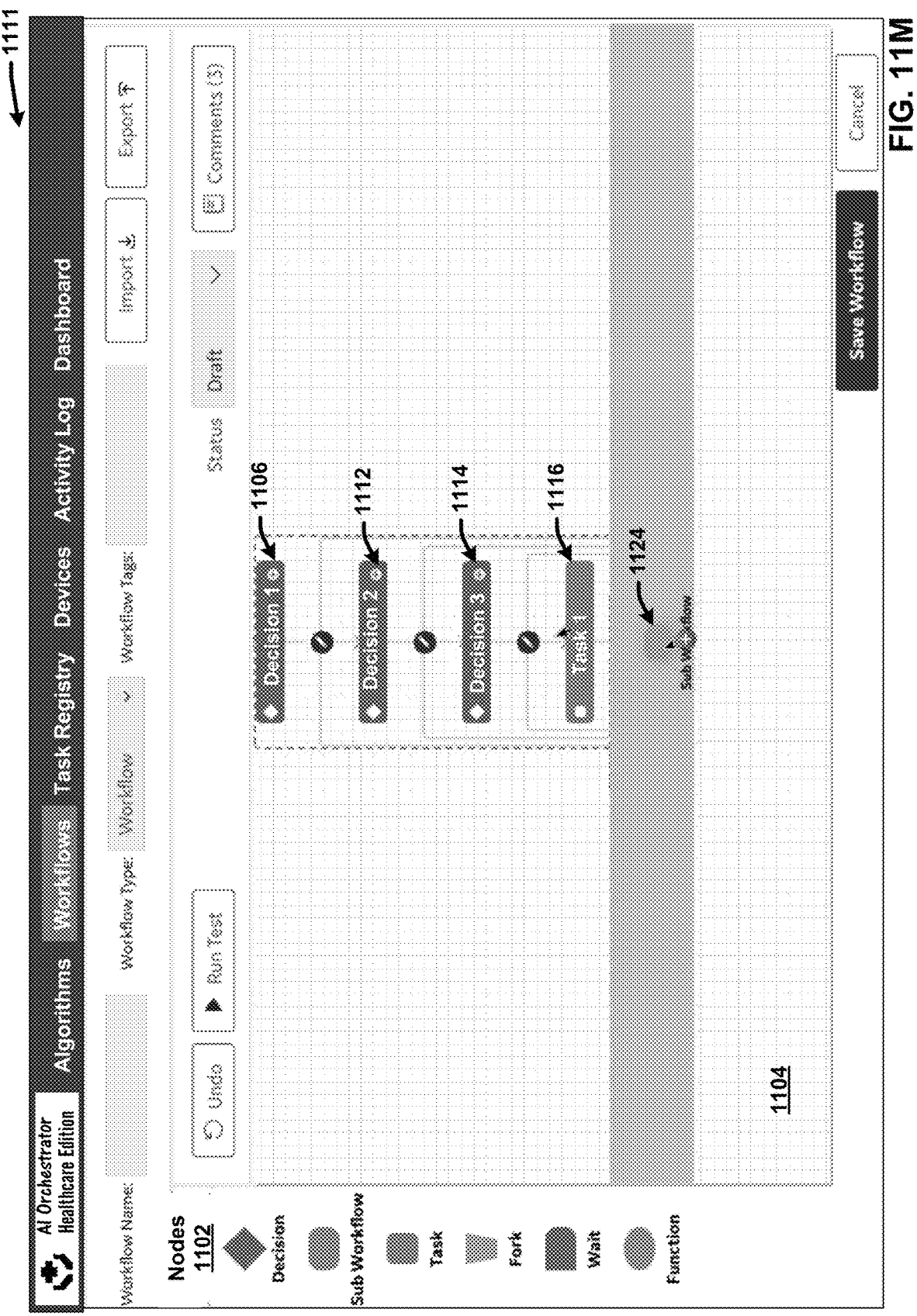
Figure 11N:
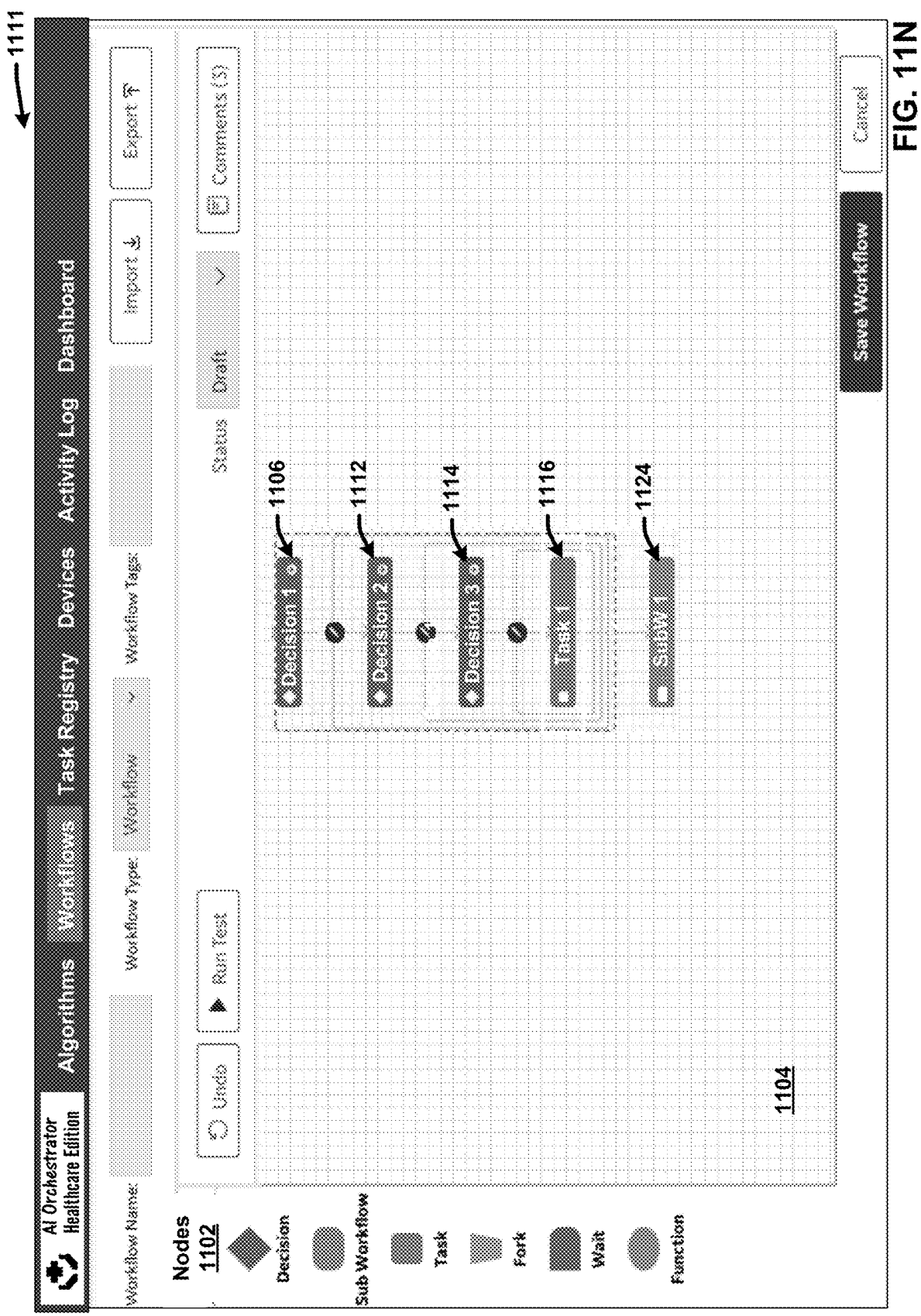
Figure 11O:
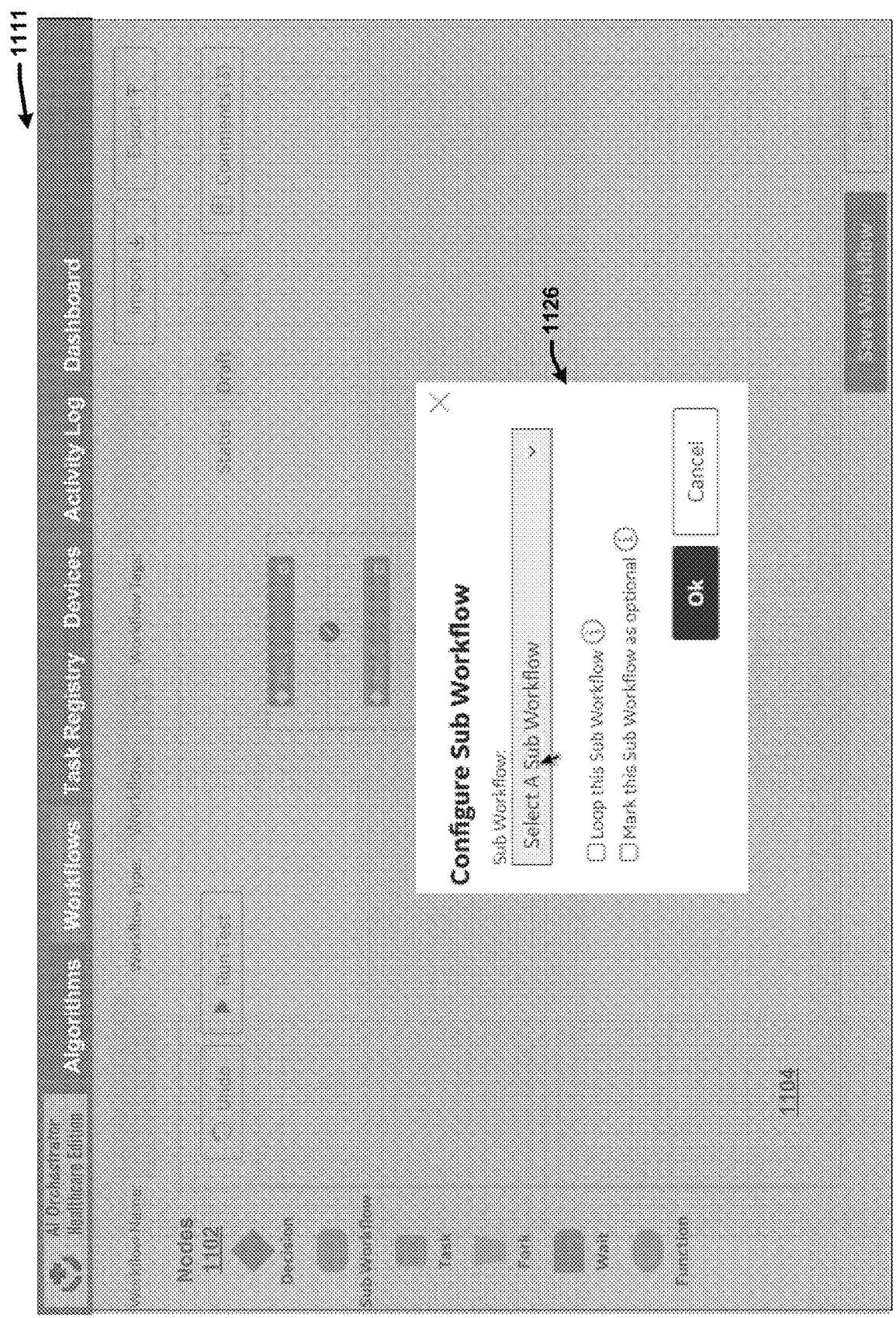
Figure 11P:
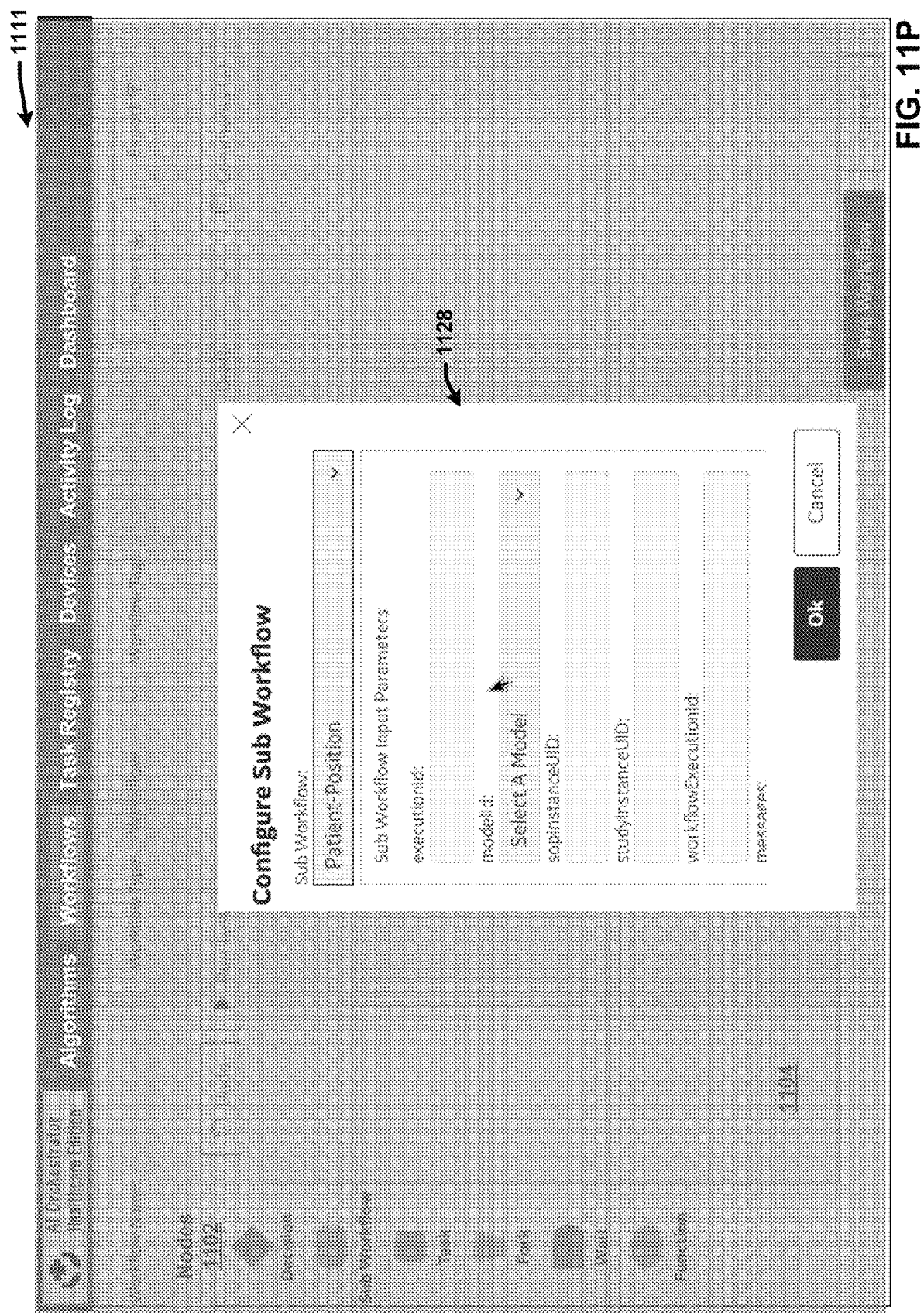
Figure 11Q:
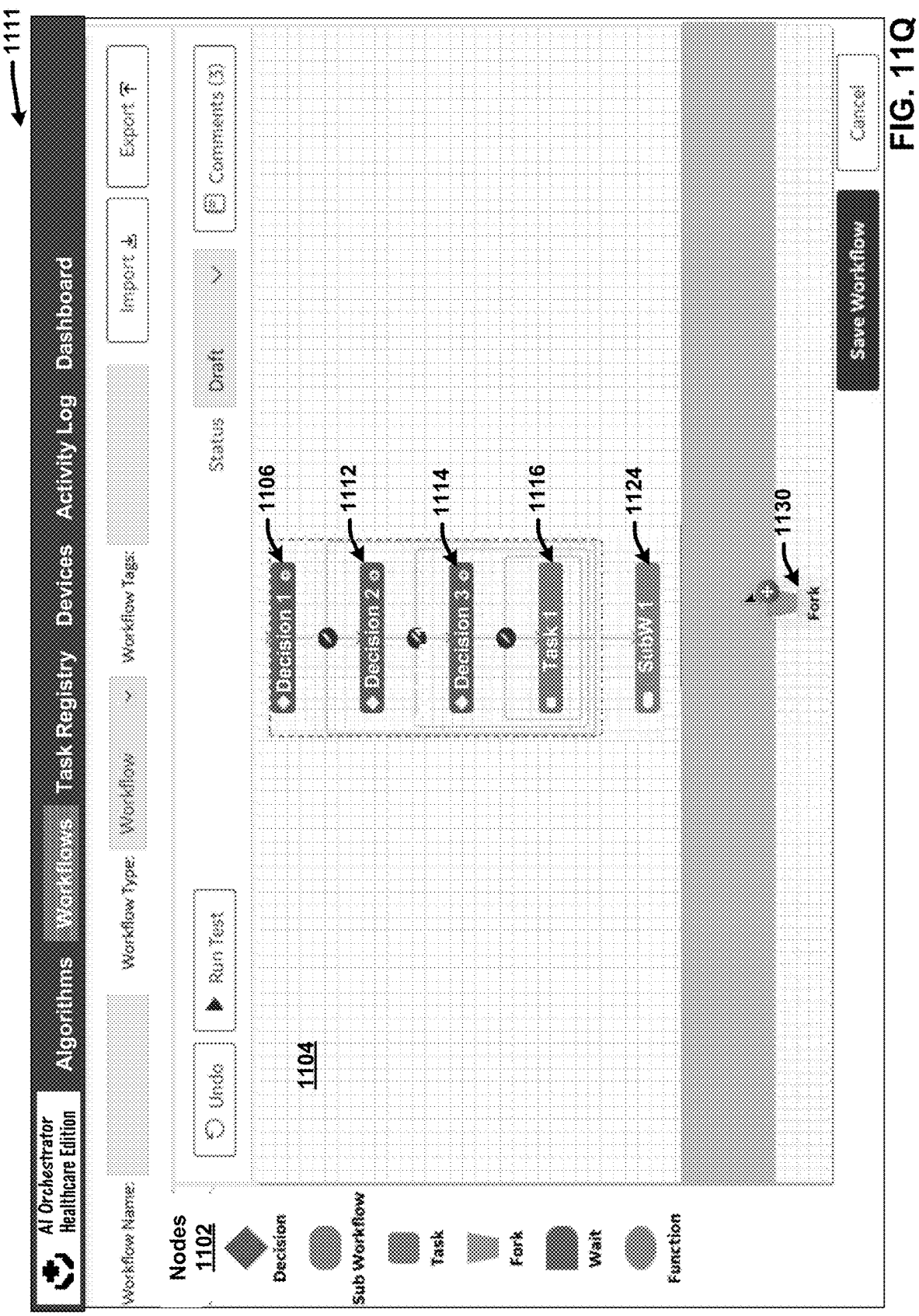
Figure 11R:
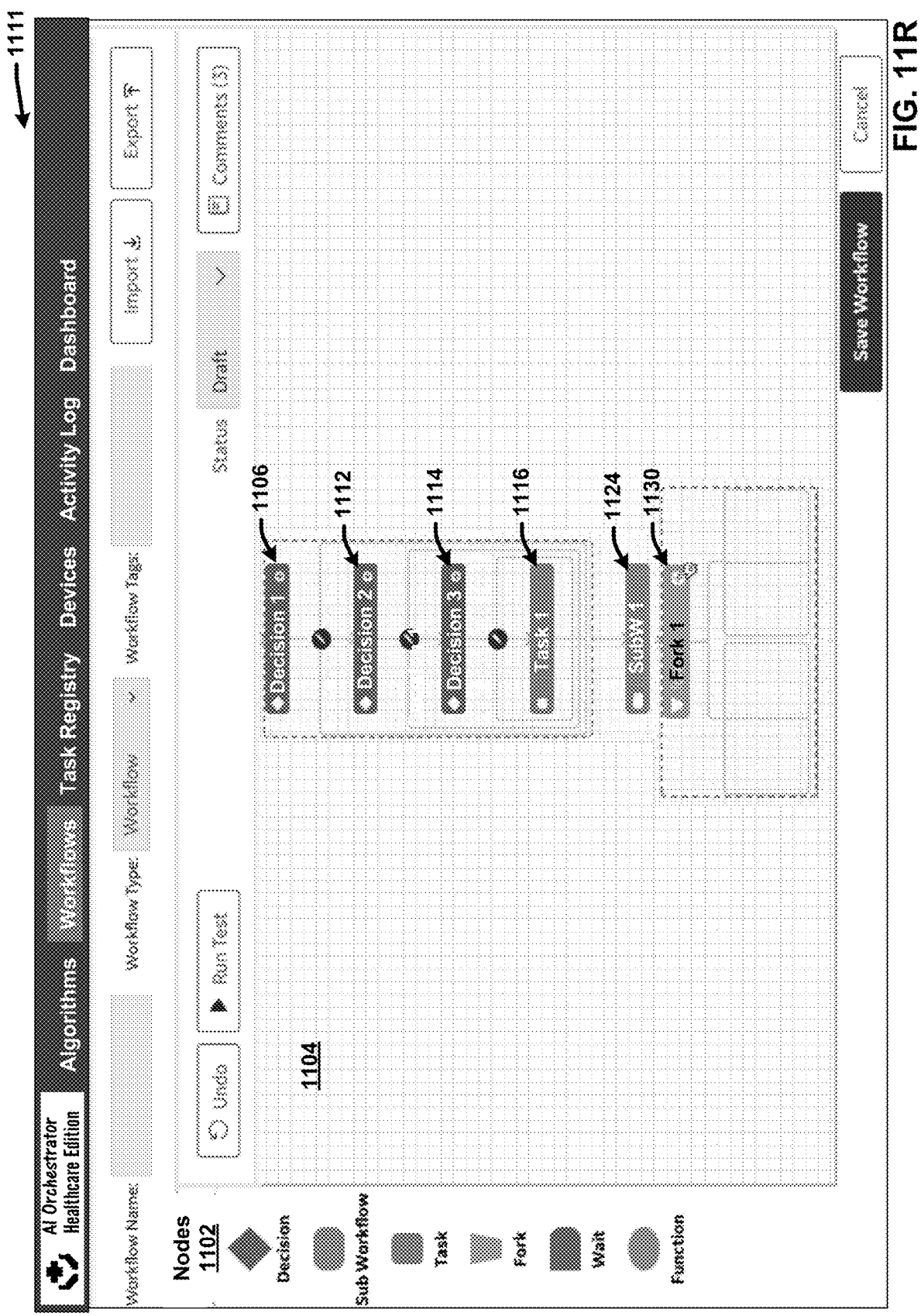
Figure 11S:
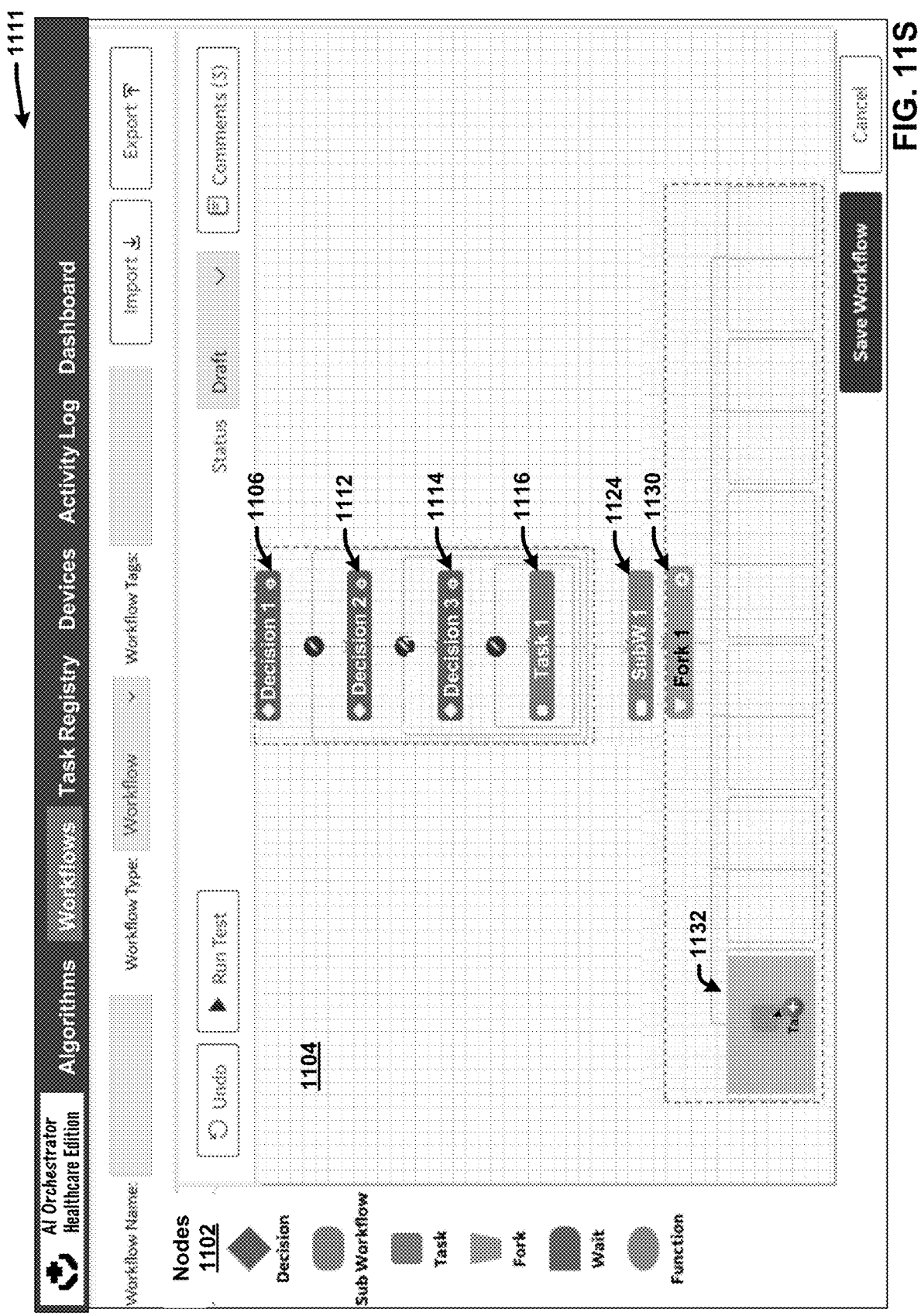
Figure 11T:
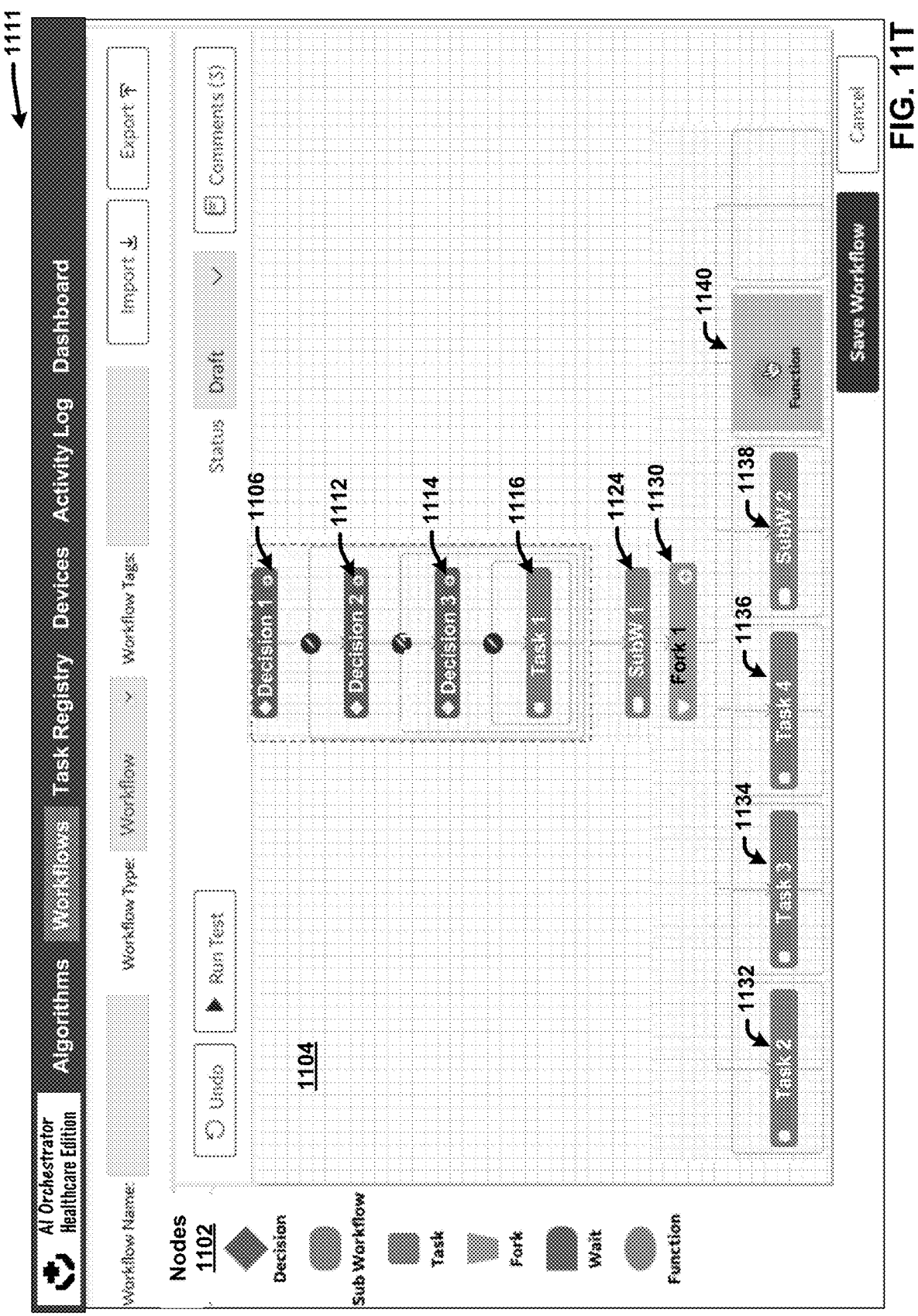
Figure 11U:
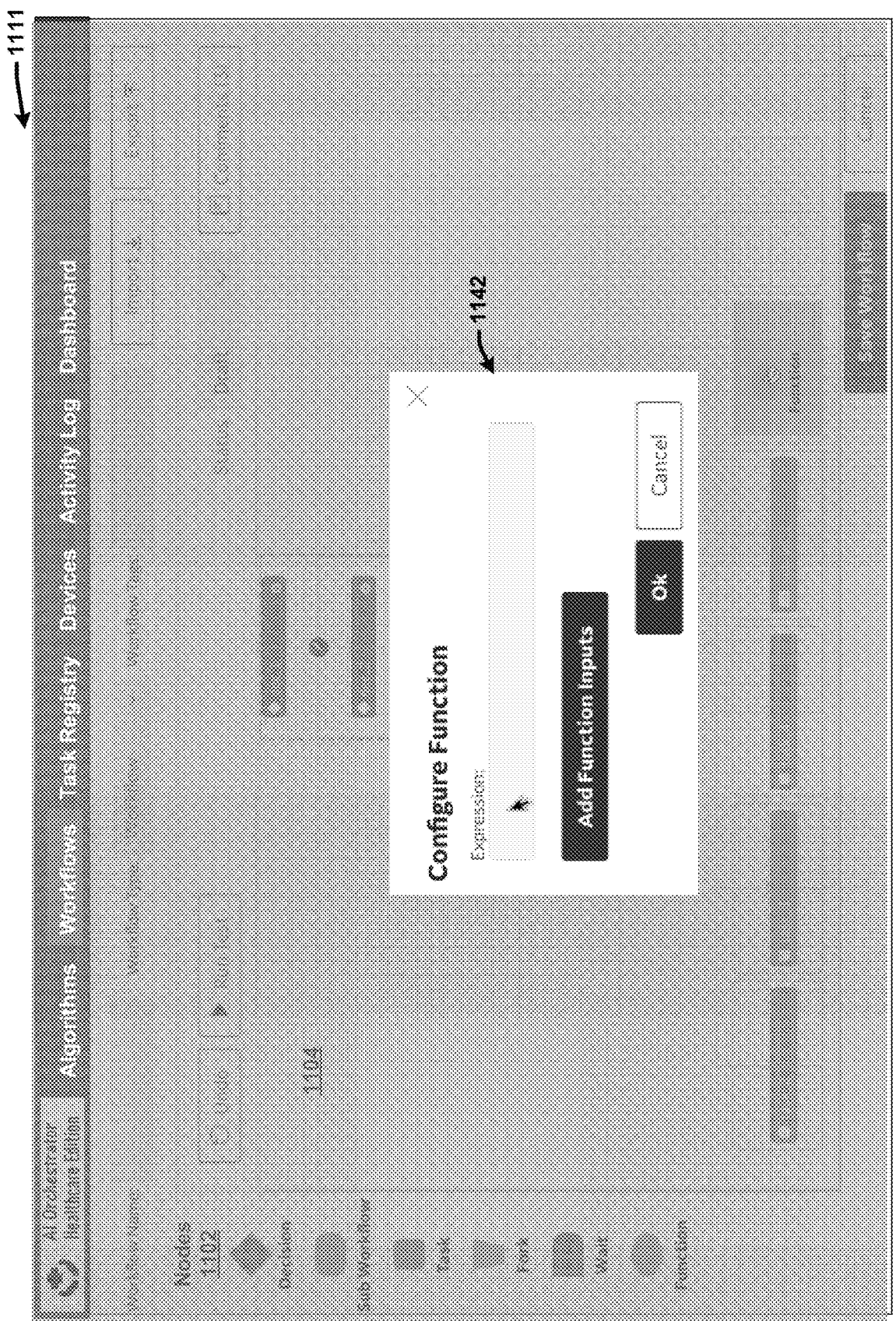
Figure 11V:
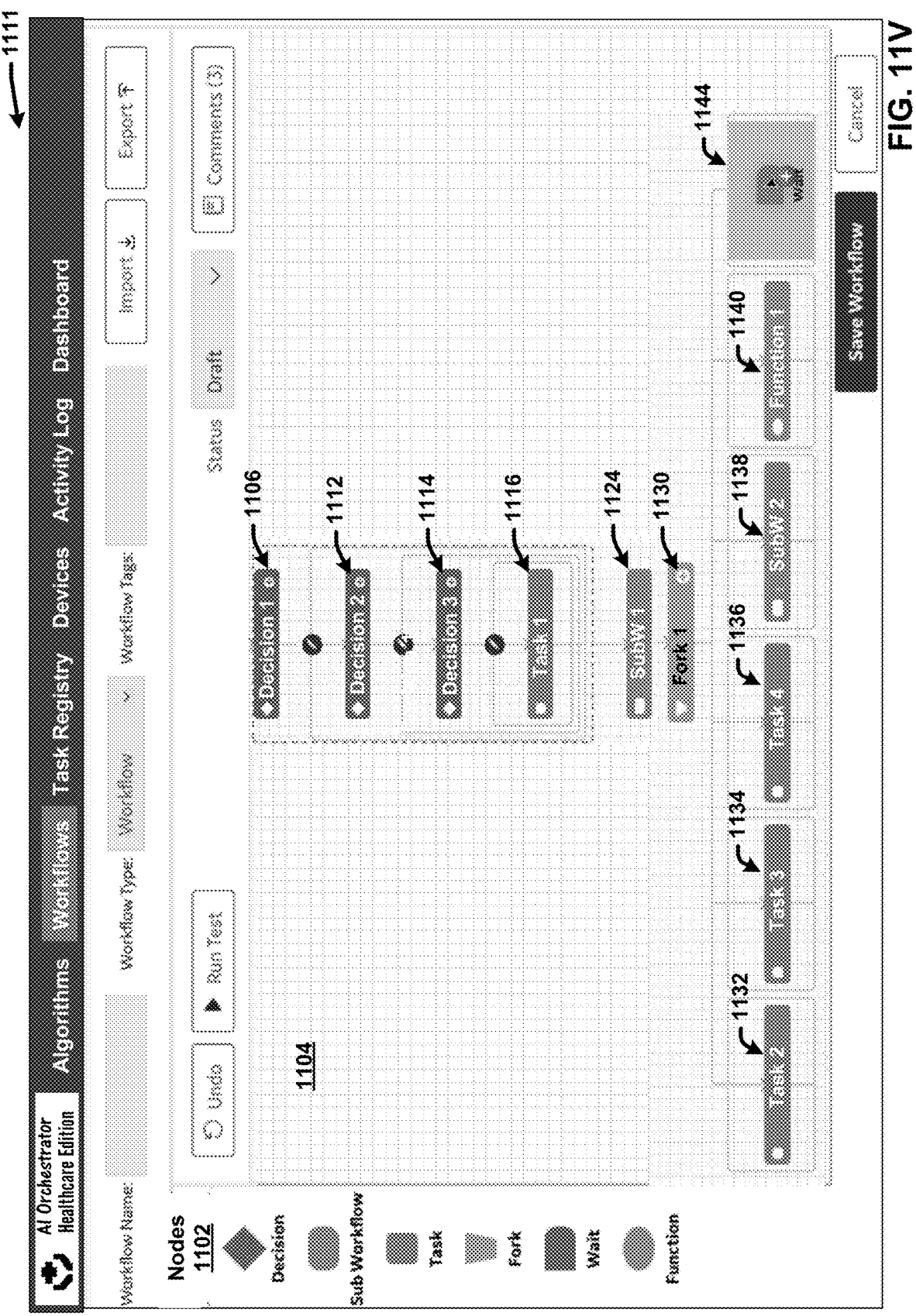
Figure 11W:
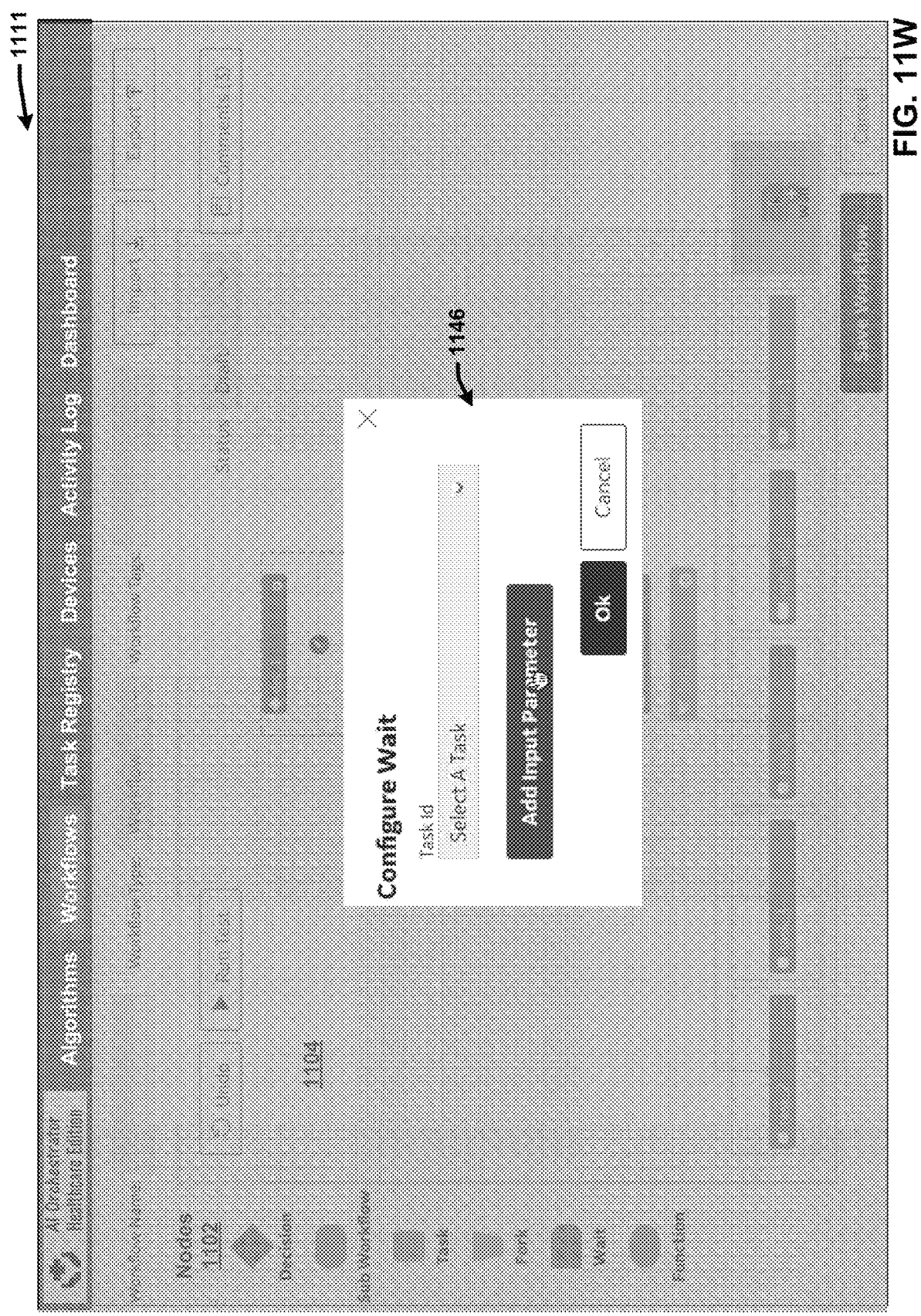
Figure 11X:
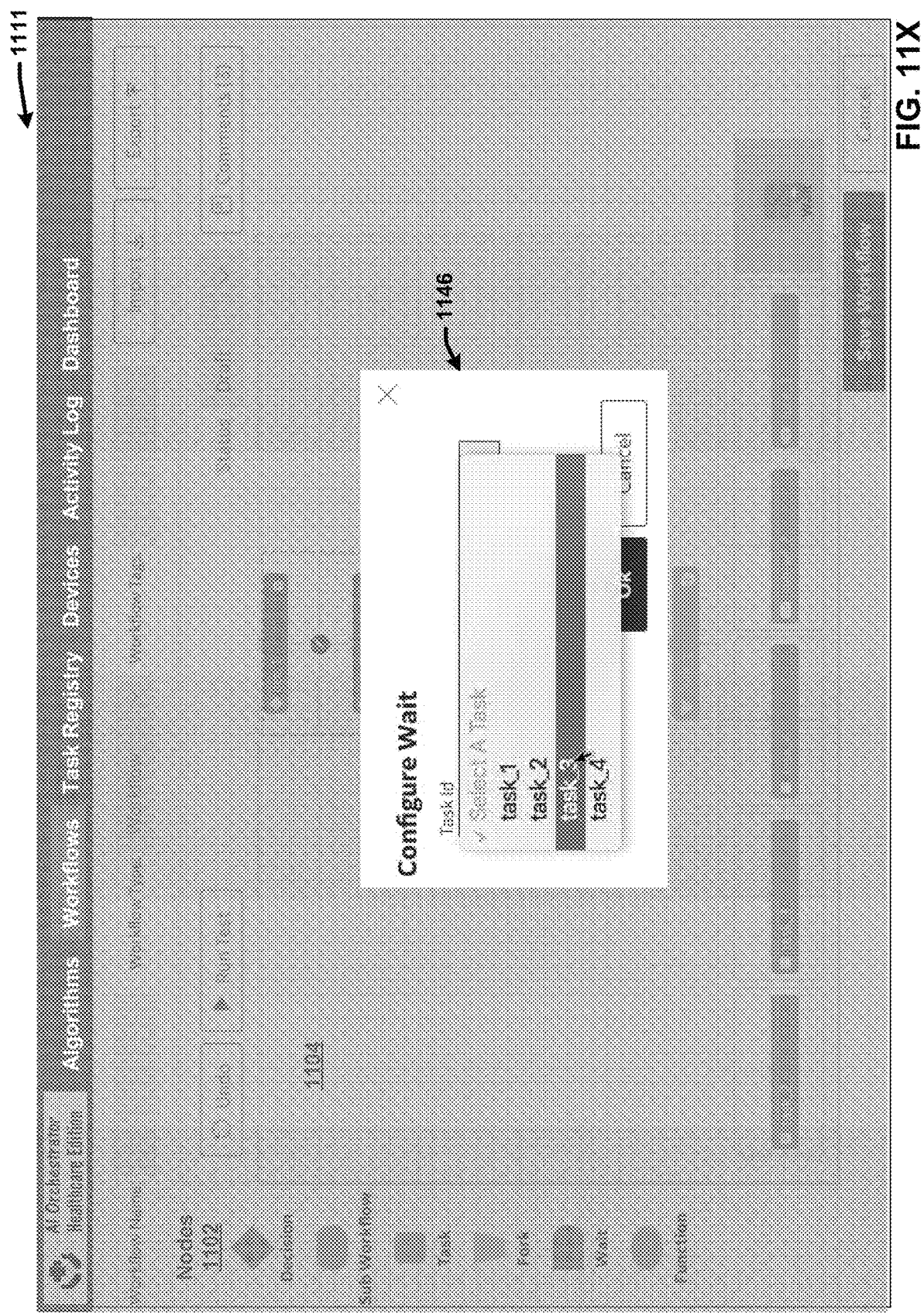

FIGS. 11A-11X present example UIs of a workflow creation application provided by the workflow creation component 528 in association with usage of the workflow creation application to create a workflow in with one or more embodiments of the disclosed subject matter.

FIG. 11A presents an example workflow creation UI 1101 providing workflow templates for developing workflows in accordance with one or more examples of the disclosed subject matter. In some embodiments, the workflow creation UI 1101 can be generated and presented in response to selection of the workflow creation button from workflow management UI 1001. The workflow templates include a blank workflow template as well as various pre-formatted templates that can be used to create new workflows. In this example, the pre-formatted templates include a PTX series aggregation template, a diffusion weighted imaging (DWI) series aggregation template, an Xray study parent workflow template, a study stroke parent workflow template, and a PACS chest frontal sub-workflow template.

FIG. 11B presents an example workflow creation UI 1111 that provides interactive tools for creating a workflow in accordance with various embodiments of the disclosed subject matter. In the embodiment shown, the workflow creation UI 1111 is blank. The workflow creation UI 1111 provides selectable and configurable nodes 1102 that can be dragged and dropped onto the creation area 1104 to build a workflow. In the embodiment shown, these nodes include a decision node, a sub-workflow node, a task node, a fork node, a wait node and a function node. These nodes can provide the same functions for the corresponding nodes previously described with reference to FIGS. 2A-2C. Repetitive description of like elements is omitted for sake of brevity.

FIG. 11C demonstrates dragging and dropping a decision node onto the creation area 1104 in association with building a new workflow. A workflow decision node can be used at the beginning of a workflow to filter input images to ensure the input images satisfy one or more criteria of the workflow. As shown in FIG. 11D, after a node has been dropped onto the creation area, the node becomes selectable and configurable and the workflow creation component 528 automatically adds connectors and endpoints.

FIGS. 11E-11F demonstrates configuring the decision node 1106. As shown in FIG. 11D, selection of the decision node 1106 can result in generation of pop-up window 1108 that provides fields for configurating the decision input and output. In this example, the fields include a case expression and an initial decision. FIG. 11F demonstrates selecting/inputting a case expression. The case expression provides for adding an input filter parameter (e.g., by patient, source, modality, etc.). In this example, a drop-down list of predefined case expressions can be provided to select the decision case expression. Additionally, or alternatively, the administrator can type a new case expression. After the input has been received providing the decision input and output fields, the decision configuration component 530 generates the corresponding decision code/logic for the decision function and saves the configured decision.

FIG. 11G demonstrates addition additional decision nodes to the workflow. In the embodiment shown, a second decision node 1112 has already been added and configured and a third decision node 1114 is being added.

FIGS. 11H-11I demonstrates adding a task node to the workflow. As can be seen in FIG. 11H-11I, each time a new node is added to the workflow, the workflow creation component 528 automatically adds connectors and endpoints between nodes.

FIG. 11J-11L demonstrate configuring the task node 1116. As shown in FIG. 11J, selection of the task node can result in generation of pop-up window 1118 that provides fields for configurating the task. As previously described, the task node can be used to integrate an HTTP service call into the workflow. The Task node can also be used to integrate models/algorithms and other functions into the workflow for execution as Lambda tasks, Kubernetes jobs or the like. This feature opens multiple possibilities specially related to legacy systems where the client service is not under HTTP and is only a simple command line and/or executable. For example, a task node can be used to integrate an algorithm (e.g., an AI model) included in the algorithm catalog data 124 into the workflow as an HTTP request, a Lambda task or a Kubernetes job.

In the embodiment shown, a task can be configured by inputting the request method, the request uniform resource method (URL) for the task, and the task header, or by selecting a predefined custom task from a drop-down menu. In various embodiments, the task registry component 524 can provide for generating and storing custom tasks (e.g., in the workflow and task registry data 122) that can be exposed and selected in the custom task drop-down menu. FIG. 11K demonstrates selecting a request method for the task. In this embodiment, the task configuration provides for configuring four different types of HTTP tasks, including a "GET, a "POST," a "PUT," and a "DELETE." As shown in FIG. 11L, in this example, the GET request method is selected and the URL for a desired AI model to be run (e.g., "xyzmodel") is entered. After data fields have been completed and input has been received providing the request method, the request URL and the request header, or custom task has been selected, the task configuration component 532 generates the corresponding task code/logic for the task and saves the configured task.

FIGS. 11M-11N demonstrate adding a sub-workflow node 1124 to the workflow. As shown in FIG. 11M, the sub-workflow node can be dragged and dropped onto the creation area 1104. Thereafter, as shown in FIG. 11N, the sub-workflow node is automatically connected to the previous node and it becomes selectable and configurable.

FIGS. 11O-11P demonstrate configuring the sub-workflow node 1124. As shown in FIG. 11O, selection of the sub-workflow node 1124 can result in generation of a configuration up-up window 1126 that provides fields for configurating the sub-workflow. In accordance with this embodiments, sub-workflows are previously created workflows that are saved as sub-workflow types. In this regard, saving a created workflow as a "sub-workflow" results in the sub-workflow being selectable in the drop-down menu. FIG. 11P presents an updated sub-workflow configuration window 1128 with additional data fields for entering the sub-workflow parameters that can be generated in response to selection of a particular sub-workflow, which in this example is identified as a patient-position sub-workflow. These additional data fields can vary based on the selected sub-workflow. In this regard, after a sub-workflow has been selected and added and the input parameters provided, the sub-workflow configuration component 534 generates the corresponding task code/logic for the sub-workflow and saves the configured sub-workflow.

FIGS. 11Q-11R demonstrate adding a fork node 11130 to the workflow. In FIG. 11Q, the fork node 1130 is being dragged and dropped, and in FIG. 11R, the fork node has been successfully attached after the sub-workflow 1124. As previously described, a fork node can be used to split the workflow into two or more parallel processes or strings. As shown in FIG. 11R, in response to addition of the fork node 1130, the fork configuration component 532 automatically creates two branches. The number of branches can be increased as desired by selecting the fork node repeatedly. For example, FIG. 11S demonstrate addition of six separate branches that can be generated in response to continued selection of the fork node 1130. In this example, a second task node 1132 is being added to the first branch.

FIG. 11T demonstrates progression of the workflow after addition of a third task node 1134 to the second branch, a fourth task node 1136 to the third branch, a second sub-workflow node 1138 to the fifth branch, and a function node 1140 to the fifth branch. It should be appreciated the additional task nodes and sub-workflow nodes can be configured as described previously. Repetitive description is omitted for sake of brevity.

FIG. 11U demonstrates configuring the function node 1140. Similar to the other nodes, after the function node has been added to the workflow it can become selectable and configurable, wherein selection of the function node results in generation of the configured function pop-up window 1142. The configure function pop-up window 1142 can be used to enter an expression (e.g., a Javascript code expression or the like), such as a data conversion function, a calculation function or the like that can be executed by the workflow execution engine 116. After the expression code has been entered, the function configuration component 540 generates the corresponding function code/logic for the function and saves the configured function.

FIG. 11V demonstrates adding a wait node 1144 to the sixth branch. A wait node can be used to bind or synchronize two or more tasks. FIGS. 11W-11X demonstrate configuring the wait node in association with selection of the dropped node. As shown in FIG. 11W, a wait node can be configured via the configure wait pop-up window 1146 by selecting a task and optionally adding an input parameter. FIG. 11X demonstrates selecting a task for the wait. In this example, four tasks are included in the workflow, resulting in four task options to select for the wait node. In this regard, selection of task 3 for example would result in the workflow execution engine 116 waiting to execute any nodes following the wait node until task 3 has been completed and the results received.

Figure 12A:
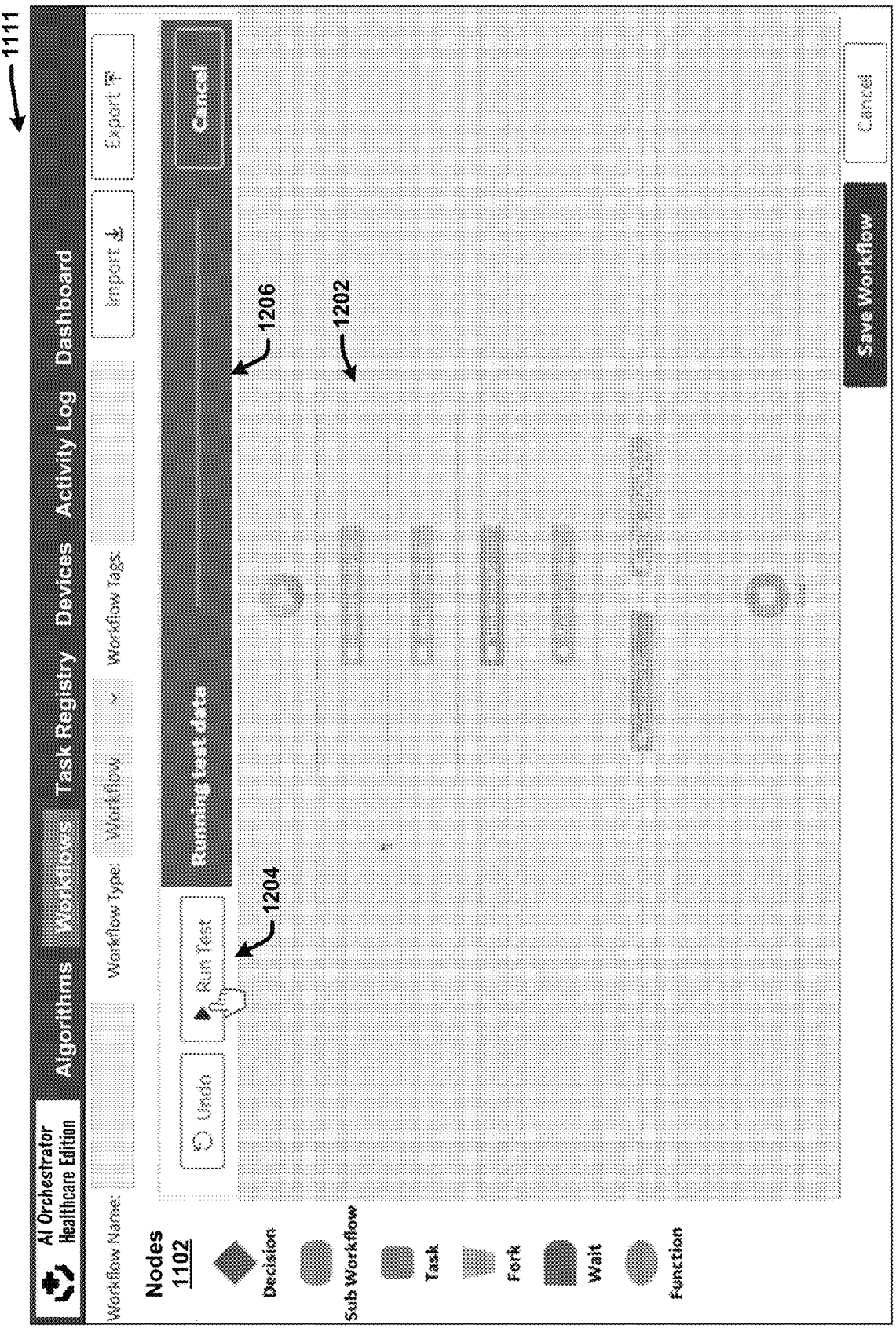
FIGS. 12A-12B illustrate a workflow simulation function of the algorithm orchestration management application accordance with one or more embodiments of the disclosed subject matter.
Figure 12B:
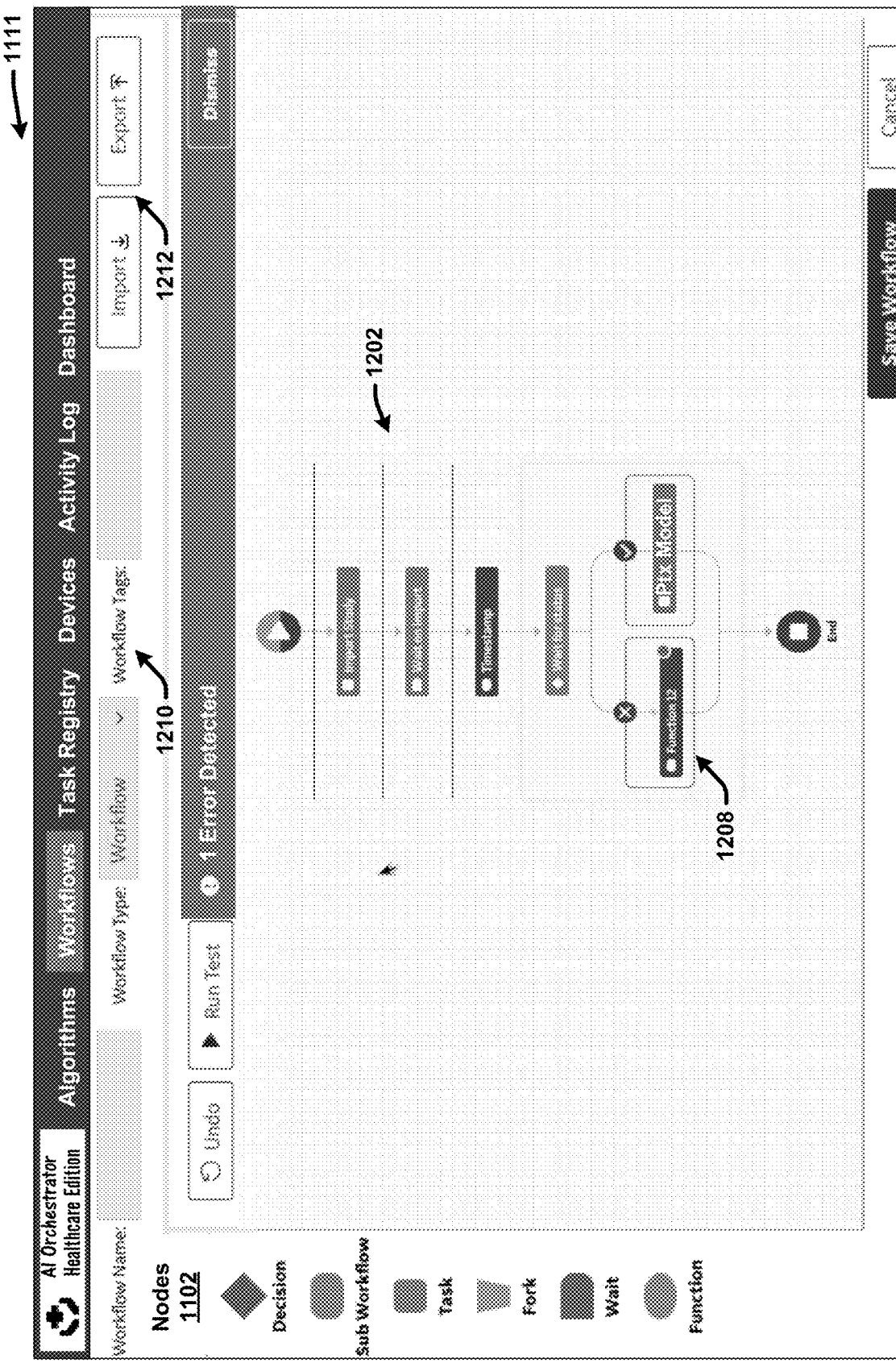

FIGS. 12A-12B illustrate a workflow simulation function of the algorithm orchestration management application accordance with one or more embodiments of the disclosed subject matter. With reference to FIGS. 5A and 12A-12B, after a workflow has ben created, the simulator component 542 can provide a simulation function that provides for running the workflow in a test mode within the workflow creation UI 1111. For example, in the embodiment shown in FIG. 12A, a "run test" icon 1204 has been added to the workflow creation UI 1111 that can be selected to initiate the simulation. In response to a request to run the workflow simulation, the simulator component 542 can direct the workflow execution engine 116 to run the workflow 1202 on one or more test images to ensure the nodes are configured property and to identify any issues with the workflow. The test images can include both images that satisfy and fail to satisfy any decision mode criterion.

For example, FIG. 12A depicts a workflow 1202 being executed in simulation mode in response to selection of the run test icon 1204. In response to selection of the "run test" icon 1204, a progression bar 1206 can be displayed that shows the progress of the test, which in this example is currently "running test data." FIG. 12B presents the results of the simulation. As exemplified in FIG. 12B, the simulator component 524 can identify any issues or errors with a workflow, such as issues that resulted in a node failing to be executed or executed properly. In this example, one error was detected at node 1208. The simulation component 542 can also generate and provide error messages with information regarding the detected error. For example, the error message can identify the node where the error occurred and the reason for the error. Some example errors can include, but are not limited to: "no content" (indicating no resources are available in the response); "bad request" (indicating that a request is invalid); "unauthorized (indicating the user/system is not authorized to access a resource or perform an action); "not found" (indicating the resource does not exist); "conflict" (indicating a resource cannot be created or modified as it conflicts with an existing resource); "internal server error" (indicating something unexpected happened); and "bad gateway" (indicating a dependency failed).

The simulation tool can be used to test run any previously generated workflow as well. For example, with reference again to FIG. 10B, in the embodiment shown, the simulator can be accessed and applied to a workflow directly from the workflow management UI 1001 via right clicking on a desired workflow and selecting the "run simulator" option from the pop-up window 1002.

With reference again to FIGS. 5A and 12B, the tag component 544 can also provide a workflow tagging function that can be accessed via the workflow creation UI 1111. For example, as shown in FIG. 12AB a "workflow tags" icon 1210 is provided that can be selected to apply tags (e.g., metadata tags) to the workflow. The metadata tags can include any attribute a developer or administrator would like to associate with the workflow. For example, the metadata tags can include tags regarding attributes of input images applicable to be processed by the workflow (e.g., modality, anatomical part, patient attributes, image orientation, etc.), tags regarding the algorithms included in the workflow, tags regarding the workflow creation process and the creator (e.g., timing, creator identity, collaborators, etc.), tags regarding the quality of the workflow, tags regarding the average execution duration of the workflow, and the like. Tags added to a workflow can be used to facilitate searching for and filtering workflows based on desired criteria. Tags added to a workflow can also be used by the orchestration conductor component 112 and/or the workflow execution engine 116 to identify applicable workflows for input images received in association with image processing requests. The workflow import and export functionality provided by the import/export component 548 can also be accessed via the workflow creation UI 1111 in association with selecting the correspond icons 1212.

Figure 12C:
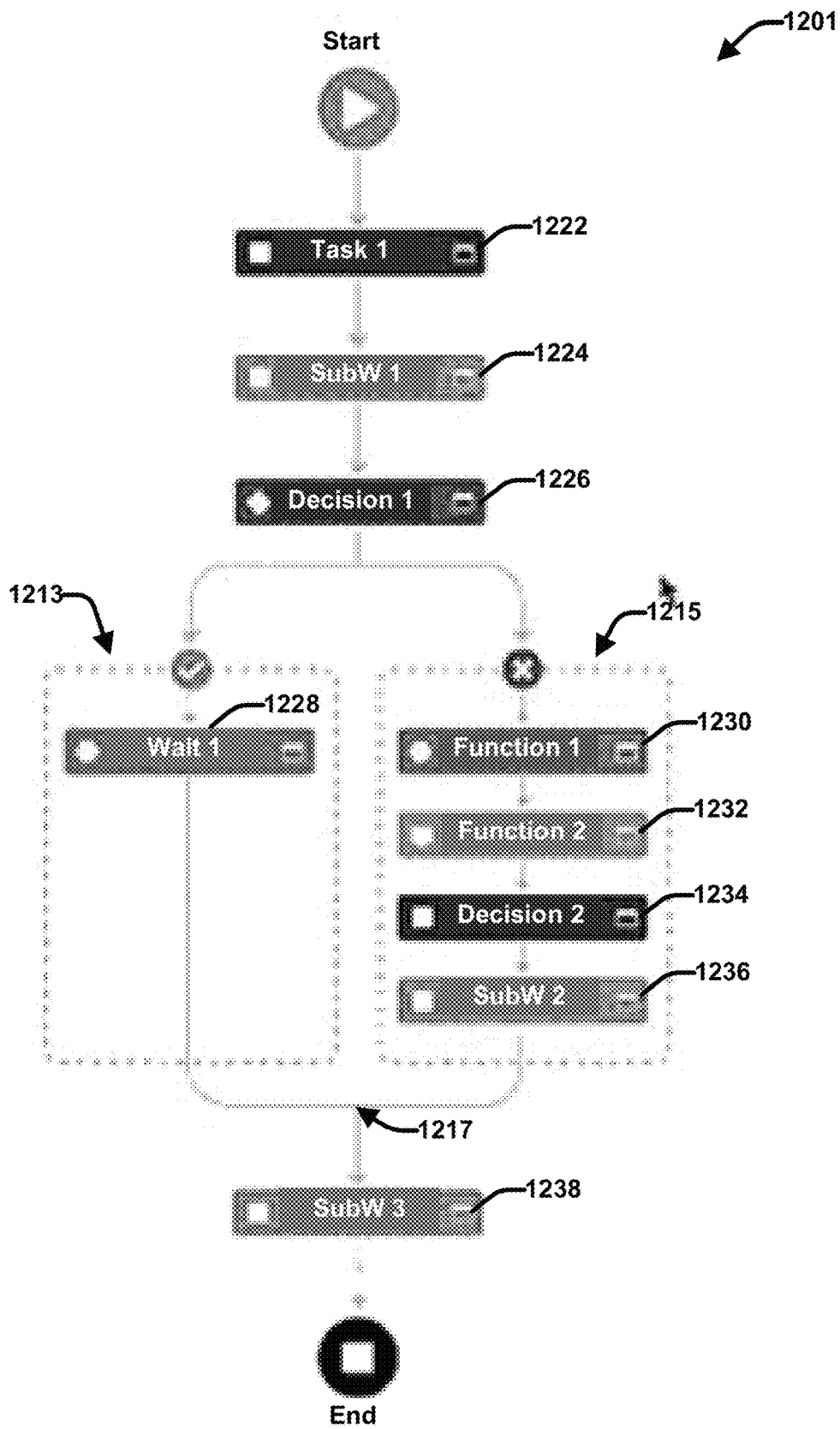
FIGS. 12C-12D present some additional example workflow diagrams in accordance with one or more embodiments of the disclosed subject matter.
Figure 12D:
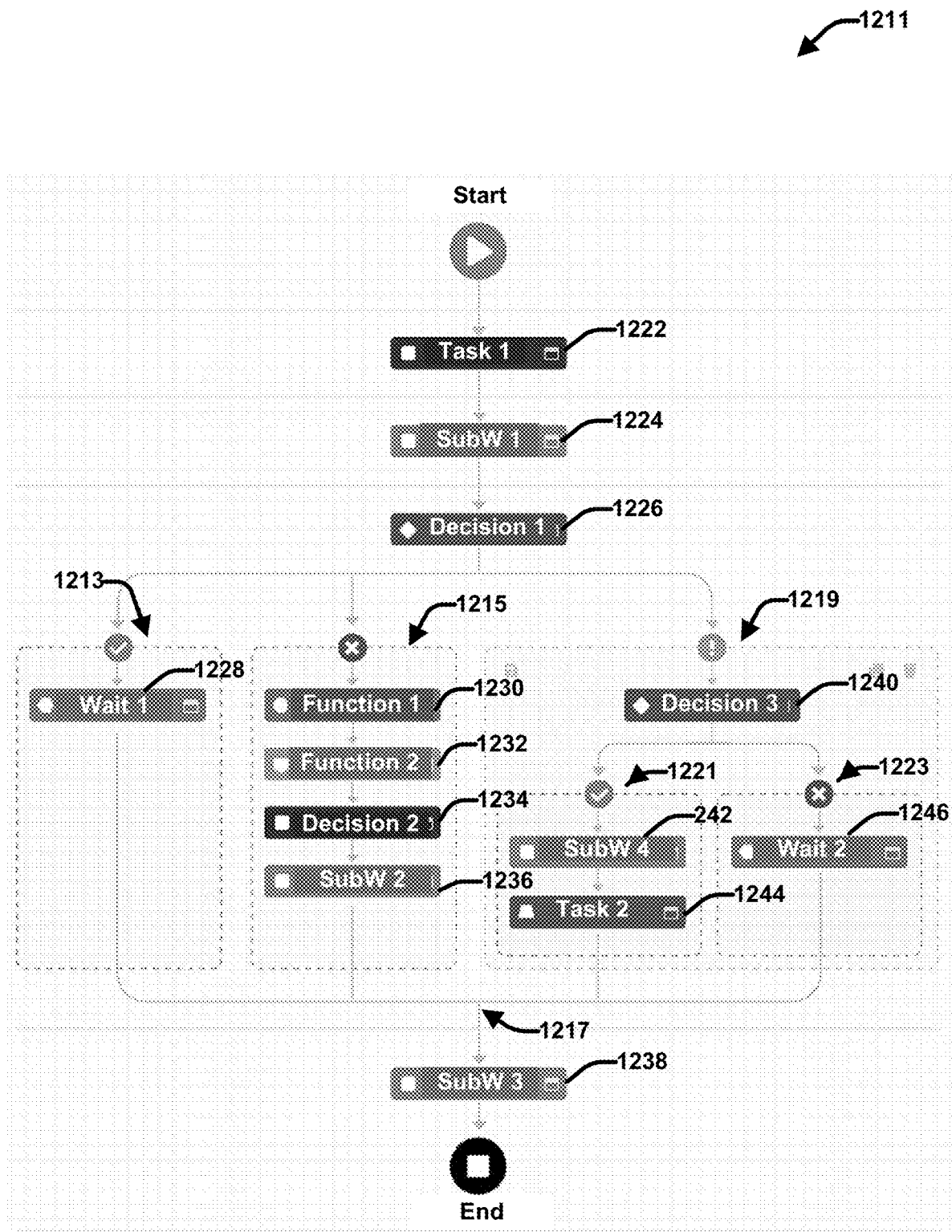

FIGS. 12C-12D present some additional example workflows that can be created using the workflow creation tools and functions provided by the workflow creation component 528 in accordance with one or more embodiments of the disclosed subject matter.

FIG. 12C illustrates an example of workflow 1201 having parallel branches and sub workflows in accordance with one or more examples of the disclosed subject matter. In accordance with workflow 1211, a start instruction begins the workflow 1211 and at 1222, a first task instruction is defined for workflow execution. At 1224, a first sub-workflow is defined for execution. As mentioned previously, a sub-workflow is separate workflow of execution instructions (e.g., models, parallel/serial branches, tasks, and so forth). At 1226, a first decision branch is executed followed by a fork that creates a true path 1213 and a false path 1215 for the first decision 1226. If the decision at 1226 is evaluated as true, a wait instruction 1228 (e.g., time delay, or wait for some other task completion) is executed. If the decision at 1226 is evaluated as false, branch 1215 executes. As shown, branch 1215 also contains a first function 1230, a second function 1232, a second decision 1234 and a second sub-workflow 1236. At 1217, a join instruction is executed to join processing paths from 1213 and 1215. At 1238, still yet another sub-workflow is executed and then the workflow ends.

FIG. 12D illustrates an example of the workflow depicted in FIG. 12C where an additional workflow processing branch 1219 is added in accordance with one or more examples of the disclosed subject matter. Due to the similarity to workflow 1211 with workflow 1201, each processing instruction of workflow 1211 is not described for purposes of brevity. At 1219 an additional branch is added. Instead of two parallel branches provided by the fork, a third branch 1219 is added to the existing branches of the workflow 1211. The third branch 1219 includes a third decision 1240 having a true path at 1221 and a false path at 1223. The true path 1221 includes a fourth sub-workflow at 1242 followed by a second task 1244. The false path 1223 includes a wait instruction 1246. The paths 1221 and 1223 are met at sub-workflow 1228 where the process ends thereafter.

With reference again to FIG. 5A, the task registry component 524 can provide for generating custom tasks that can be added to the workflow and task registry data 122 and used in workflows. The task registry component 524 adds the ability to employ custom task templates to define custom tasks in the system and assign them a name. Custom tasks can be directly selected via the task configuration pop-up window (See FIG. 11J and pop-up window 1118), thereby minimizing the amount of coding knowledge (e.g., to be able to determine the correct request method, input the request URL and header for example) and user input needed during workflow creation.

FIGS. 13A-13D presents example task registry UIs that illustrates the features and functionalities of the task registry component 524 in accordance with one or more embodiments of the disclosed subject matter.

FIG. 13A presents an example task registry UI 1301 that can be presented in response to selection of the task registry tab from the upper menu. The task registry UI 1301 presents a searchable and filterable list view of previously created custom task. The task registry UI 1301 provides information identifying the task name, the type, the latest update, the creator, a description of the task, and tags added to the task. The task registry UI 1301 also provide a "create a task template" button that can be selected to create a new custom task.

Figure 13B:
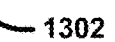

FIG. 13B presents an example custom task creation UI 1311 that can be presented in response to selection of the "create a task template" button from the task registry UI 1301. The custom task creation UI 1311 provides several data fields that can receive user input to define a custom task. These data fields provide for entering/receiving user input defining the task name, description, selecting a color for the task icon, selecting the type of task. In this example, the include an HTTP task, an asynchronous task, and a K8s-Job or Kubernetes job. Additionally, or alternatively, the task can include Lambda tasks. The remaining data entry fields can vary based on the type of task selected. In this example, the selected (and default) task type is an HTTP task type. For this task type, the remaining data entry fields include a request URL field (via which the request URL for the task is entered), a request method field, a request body field, and input variables field 1302, a request headers field and a tag entry field.

The input variables field 1302 can be selected to customize the input variables in implementations in which the task comprise an HTTP request to execute an algorithm/model (which in this case is a PTX detection model).

Figure 13C:
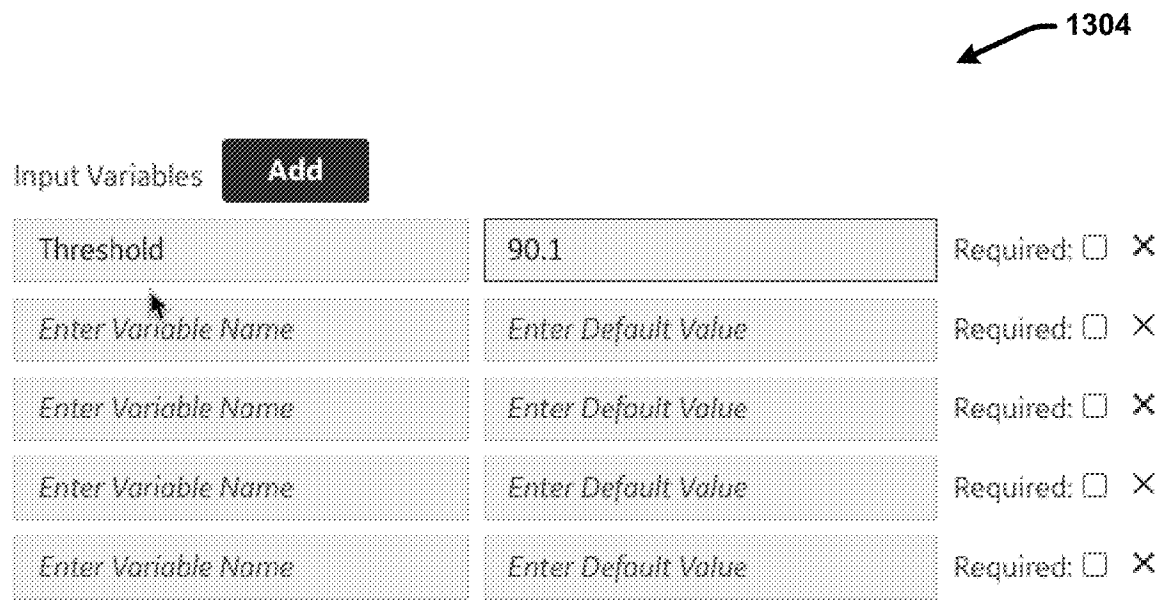

FIG. 13C provides an example drop-down menu 1304 that can be generated in response to selection of the input variables field 1302 "add" button. As shown in FIG. 13C, the drop-down menu 1304 provides for setting custom input variables requirements for algorithm/model. After the required data fields have been filled out, selection of the "save" option from the custom task creation UI 1311 can result in adding the custom task to the task registry (e.g., the workflow and task registry data 122) and returning the user back to the task registry UI 1301, as shown in FIG. 13D. As shown in FIG. 13D, a notification can be presented indicating the task has been successfully created/added. In this example, the newly added PTX detection task 1306 is now displayed as the first entry in the task registry.

Referring again to FIG. 5B, the system/device management component 554 can provide management functions regarding managing the systems and devices (e.g., the image provider systems/devise 102, the clinician device 302, the medical image storage system 306, and the like) that can access the algorithm orchestration component 110 and the services (e.g., workflows and algorithms) they are authorized to employ. In this regard, the algorithm orchestration component can receive image processing requests 106 from multiple system/devices (e.g., multiple instances of PACs and/or healthcare systems can send image processing requests to the algorithm orchestration component 110). As previously noted, the security component 508 and/or the access component 504 can restrict receiving and accepting requests to only authorized and validated devices/systems that have been added to the system/device registry data 126. In this regard, the discloses systems (e.g., system 100, system 300 and the like) can provide large (e.g. worldwide) interconnected network for receiving input data and sending output data for workflows, enabling the ability to execute a complete integrated workflow in a clinical setting.

In the embodiment shown, the system/device management component 554 can include device add/remove component 556 that can provide for adding and removing systems and devices from the system/device registry data 126. The device rules component 558 can further provide for defining custom rules and restrictions for specific systems and devices regarding what types of request the algorithm orchestration component will accept (e.g., regarding image type and image study size), and rules and restrictions regarding when and how the algorithm orchestration component 110 will fulfill the requests. For example, the device rules component 558 can be used to add rules regarding device/system priority for fulfilling requests, rules regarding the workflows and algorithms different systems/devices can access, rules regarding timing of access, rules regarding timing of provision of request results, and the like. In this regard, the device rules component 508 can be used to customize provision of services to different imaging providers. The device query component 560 can provide a search query tool to facilitate finding registered systems and devices for reviewing their service activity and customizing services.

Figure 14B:
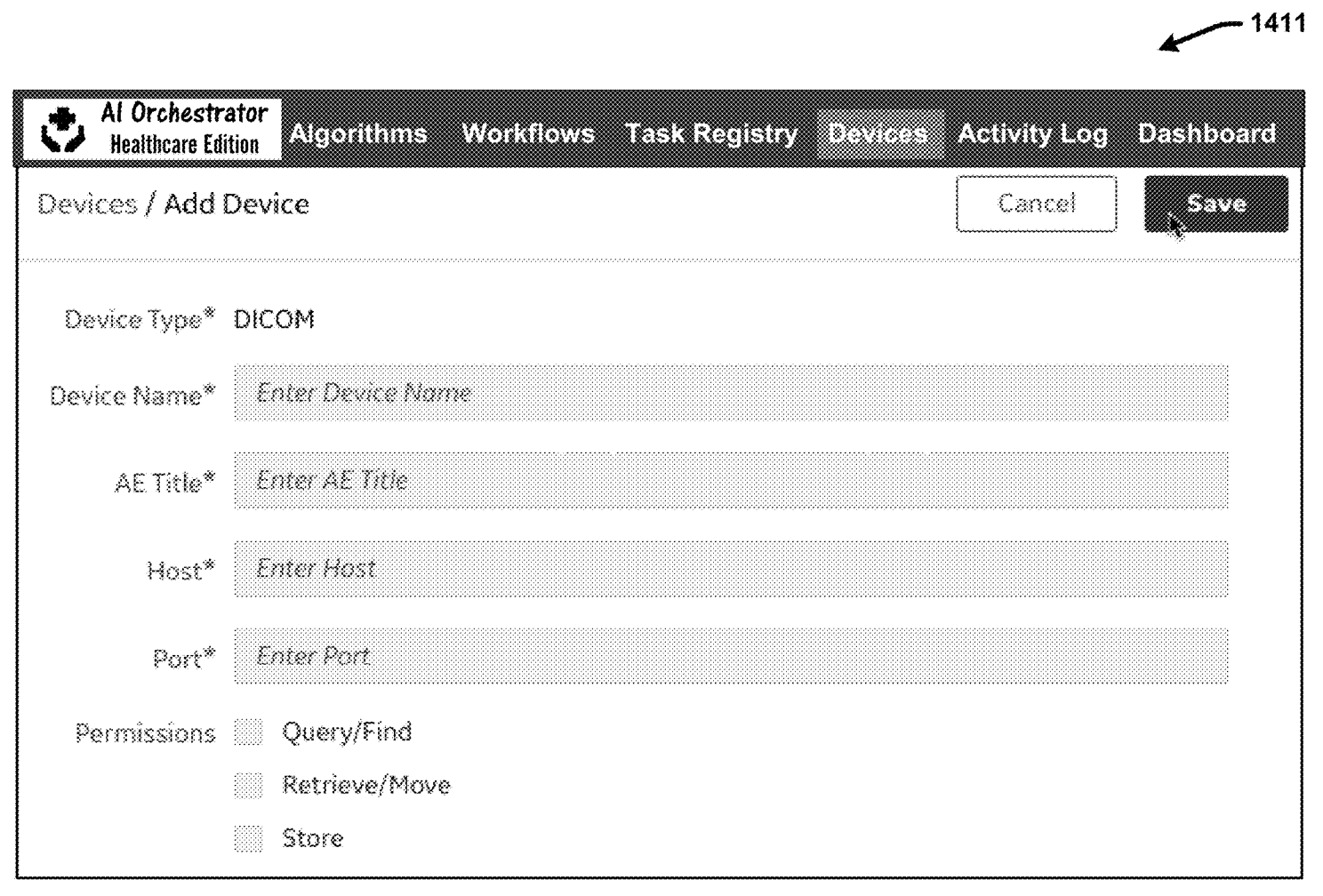

FIGS. 14A-14B present example device management UIs in accordance with one or more embodiments of the disclosed subject matter. FIG. A presents an example device management UI 1401 that can be presented in response to selection of the devices tab from the upper menu bar. The device management UI 1401 provides a searchable and filterable list of registered devices/systems from the algorithm management component 110 can receive image processing requests. The list view identifies the devise by name, indicates when their information was last updated, indicates the imaging type, the host ID and the port ID. The device management UI 1401 also provide for adding and removing a device.

FIG. 14B presents an example device management UI 1411 for adding a new device that can be generated in response to selection of the "add device" button from device management UI 1401. In the embodiment shown, the only accepted device type are DICOM devices (e.g., that provide DICOM formatted image data). To add a device, the device name, AE title, host ID and port ID are required. The device management UI 1411 also provides options for tailoring device permissions in association with adding the device.

With reference again to FIG. 5B the activity management component 562 can provide management functions regarding managing activity of the algorithm orchestration system (e.g., system 100, system 300 and the like), including activity information regarding image processing requests received and the workflows executed thereon. In the embodiment shown, the activity management component 562 can include activity logging component 564, auditing component 566, activity analysis component 568 and dashboard reporting component 570.

The activity logging component 564 can track and log the activity of the algorithm orchestration system (e.g., algorithm orchestration system 100, system 300 and the like). In particular, the activity logging component 564 can track activity information regarding all imaging processing requests 106 received and processed, including the system/device from which a request is received, the time/date when the request was received, the image data associated with the request (e.g., attributes of the image or images to be processed), the workflows executed, the algorithms executed (e.g., the algorithms included in the respective workflows that were successfully executed), the workflow results provided (e.g., the outputs of the one or more algorithms), and the timing of provision of the results. The activity logging component 564 can further tack and log detailed activity information regarding each workflow executed (or attempted to be executed but failed). In this regard, the activity logging component 564 can track information regarding timing of initiation and completion of a workflow as well as detailed information regarding the execution of each workflow node. For example, the activity logging component 564 can track the execution timing and status of each workflow task, sub-workflow, and function, including information regarding whether the task, sub-workflow and/or function was completed and executed successfully (e.g., status=completed) or unsuccessfully (e.g., status=failed).

The activity logging component 564 can also track or log any workflow execution errors detected within a workflow. In this regard, in addition to identifying execution errors and providing execution error information in association with workflow simulation, the workflow execution engine 116 can be configured to identify execution errors that arise in association with executing workflows for image processing requests 106. The workflow execution engine 116 can further generate error messages that identify the execution error that occurred, the workflow node/task where the error occurred, and the reason for the error (e.g., an error code identifying or indicating the reason for the error).

The activity logging component 564 can also track and log information regarding algorithm and workflow management. For example, the activity logging component 564 can track and log information regarding algorithms onboarded, updated, and removed. The activity logging component 564 can track and log information regarding workflow creation, activation/deactivation, updating and removal.

The activity management component 562 can further provide administers access to activity information tracked and logged by the activity logging component 564 via the algorithm orchestration management application. In some embodiments, the activity logging component 564 can generate activity logs for each received image processing request 106 that can be reviewed/viewed by the administrators to facilitate monitoring and auditing the system. An activity log for an image processing request can include any of the activity information discussed above. For example, an activity log for an image processing request can identify the image processing request (e.g., via an ID number or the like assigned to the request by the algorithm orchestration component 112), the time/date when the request was received, the system/device from which it was received, the workflows executed, the status of the workflows, any execution errors detected, and the like. The auditing component 566 can further provide an auditing function using the activity logs for performing root cause analysis regarding workflow execution errors encountered for one or more of the workflows.

Figure 15A:
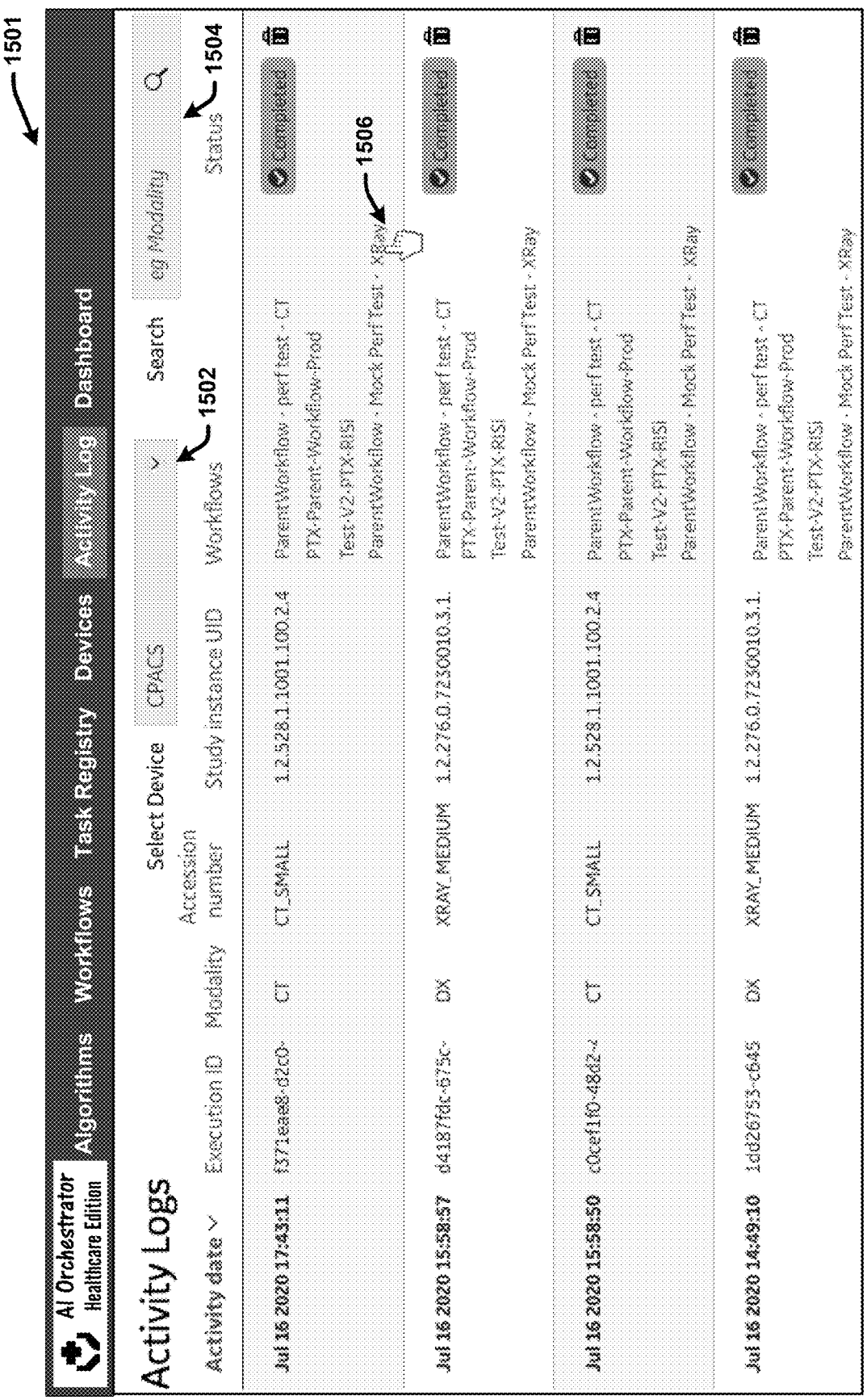

For example, FIGS. 15A-15B present example activity log UIs in accordance with one or more embodiments of the disclosed subject matter. FIG. 15A provides an example activity log UI 1501 that can be generated in response to selection of the activity log tab from the upper toolbar. The activity log UI 1501 provides a searchable/filterable list view of activity logs for image processing requests 106 fulfilled by the algorithm orchestration component 110. For example, in the embodiment shown, a device filter 1502 is provided via which the requests can be filed by source (e.g., the imaging provider system/device from which the requests were received). A search tool 1504 is also provided via which the requests can be search based on various criteria (e.g., modality, workflow type, a specific workflow, algorithm type, etc.). The activity logs respectively identify the exaction ID for the request (e.g., the request ID), the date/time of the request was received, the modality of the imaging study (or image) processed, the accession number, the study instance uniform ID number (UID), the workflows that were executed, and the status of the request fulfilment, which can be either completed, in-progress, or failed. In various embodiments, a request can be assigned a "failed" status if no workflow was determined to match the request and/or if no workflows were successfully completed. In this example, all four requests presented were completed. The workflows listed for each activity log can be selected to view detailed activity information for the workflow executed and to audit the workflow activity.

FIG. 15B provides an example workflow auditing UI 1511 that can be generated in response to selection of workflow 1506 for the first image processing request in the activity log UI 1501. The workflow auditing UI 1511 provides detailed information for the workflow, including the workflow name, the workflow type (e.g., which can be either a workflow or a sub-workflow), the workflow status, the workflow start time, the workflow duration, and the workflow version. The status of the workflow in this example is "failed," because at least one task (e.g., at least one node) in the workflow failed or otherwise did not execute properly. In this context, the status of a workflow or task does not refer to the inference/output generated by an associated algorithm, but the whether the workflow or task was executed and run as configured. In this regard, the workflow auditing tools provided by the workflow auditing UI 1511 and auditing component 566 are designed to be used by system technicians, engineers and administrators to find and correct technical issues in the system.

The workflow auditing UI 1511 can provide a detailed interactive list view of the different tasks included in the workflow, including the task start time, the task duration, the task name, the task type, the input data, the output data and the task status. In this context, a "task" refers to any node included in the workflow, not only task nodes. To facilitate root-cause analysis auditing, the tasks can be selected to view additional information about each task to determine why a task failed. The input and output data associated with each task can also be selected and viewed via the workflow auditing UI 1511. In this example, a sub-workflow task 1508 failed and a "join" task failed. In one or more embodiments, selection of the sub-workflow task 1508 can result in generation of another workflow auditing UI for the sub-workflow. The subsequent workflow auditing UI for the sub-workflow can provide the same type of information as workflow auditing UI 1511 yet include information for the tasks performed for the sub-workflow as opposed to the parent workflow. In this regard, the sub-workflow can be investigated further to determine what specific task or tasks performed therein failed to cause the sub-workflow to fail. The workflow auditing UI 1511 can also provide access to the simulator tool for running the workflow in test mode. For example, in the embodiment shown, the workflow auditing UI 1511 includes a "run test" button 1510 that can be selected to run the failed workflow in test mode. In some implementations, in response to selection of the "run test" button 1510, the interface component can present the workflow diagram for the workflow within the workflow creation UI and display the simulation therein (e.g., as shown in FIGS. 12A and 12B).

With reference again to FIG. 5B, the activity management component 562 can further include activity analysis component 568 and dashboard reporting component 570 to facilitate evaluating system activity and performance and providing a summarized view of the system's activity and performance via a dashboard UI 514. In this regard, in some embodiments, the activity analysis component 568 can analyze the activity information logged/tracked by the activity logging component 564 using various performance evaluation algorithms metrics to track the performance/activity of the system. For example, the activity analysis component 568 can determine/track the number of requests received and processed for a particular time period (e.g., per day, per week, etc.), per imaging provider, per modality, per image type, and other trackable criteria. In another example, the activity analysis component 568 can determine/track information regarding the different inferencing models executed, such as amount and/or frequency of execution of the respective models available. In another example, the activity analysis component 568 can determine/track information regarding the workflow execution errors (e.g., frequency of workflow failures, reasons for workflow failures, etc.). In another example, the activity analysis component 568 can determine/track information regarding request processing timing, including throughput (e.g., number of requests processed per hour, per day, etc.), processing duration, processing flow and backlog (e.g., request processing wait times), and the like.

The activity analysis component 568 can and/or the dashboard reporting component 570 can further generate performance reports comprising the system activity and performance information for presentation via an activity dashboard UI. In some embodiments, the activity analysis component 568 can also evaluate feedback received via the feedback component 515 regarding model performance accuracy and present this information in the activity dashboard. The activity dashboard UI can also provide results from AI model analysis with respect to actual radiological analysis of the same or similar images received via the feedback component 515. Such feedback allows a physician to gauge his own image analysis against the underlying model analysis and in view of other physicians analyzing similar images. This includes showing the number of available studies that were employed to generate the AI model analysis along with false positive rate versus true positive rate analysis. Compliance to desired diagnostic standards can be monitored in the activity dashboard where a given radiologist's actual diagnoses is compared to AI model output and/or other physicians determinations versus the respective model determinations.

Figure 16A:
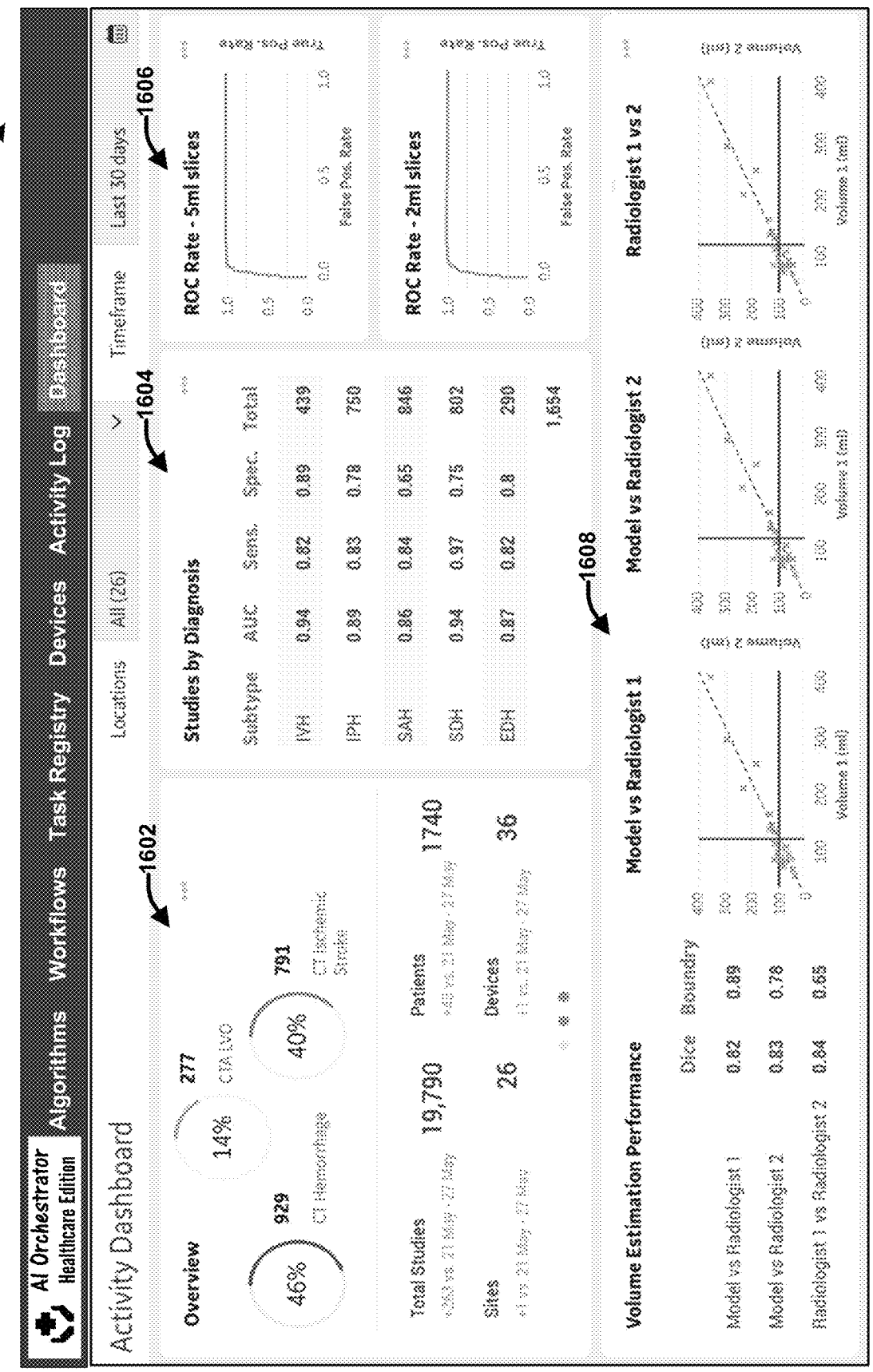
FIGS. 16A-16B present example activity dashboard UIs in accordance with one or more embodiments of the disclosed subject matter.
Figure 16B:
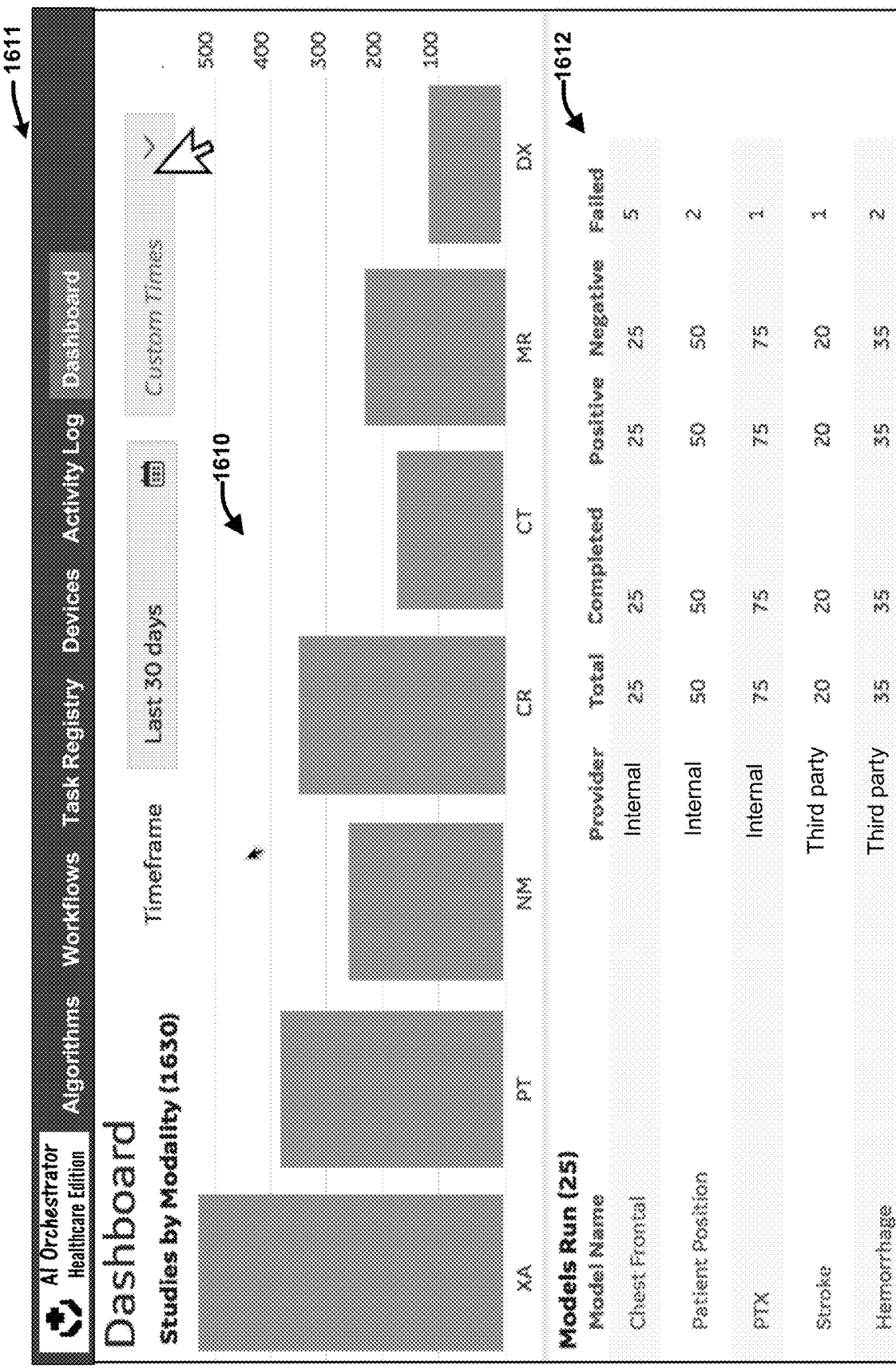

FIGS. 16A-16B present example activity dashboard UIs in accordance with one or more embodiments of the disclosed subject matter. FIG. 16A illustrates an example activity dashboard UI 1601 that provides algorithm statistics and comparison feedback with respect to radiologist's predictions and studies in accordance with one or more examples of the disclosed subject matter. The activity dashboard UI 1601 includes an overview section 1602 that includes information regarding number and percentage of application of some of the different models provided by the system, which in this example include a CT hemorrhage model, a CTALVO model and a CT schematic stroke model. The overview section 1602 also identifies the total number of studies received for processing (e.g., wherein each study corresponds to an image processing request), the total number of patients represented, the total number of sites from which the studies were received (e.g., imaging providers), and the total number of devices. The activity dashboard also summarizes the studies per diagnosis in section 1604. Also, the activity dashboard UI also includes a model performance evaluation section 1608 that can present information regarding the performance of a selected model. In this example, the model performance information compares an artificial intelligence model prediction of a medical diagnostic conditions versus that of two selected radiologists. The activity dashboard also includes receiver operating characteristic (ROC) curve graphs 1606 summarizing false positive diagnostic rates versus true positive diagnostic rates for all diagnostic models.

FIG. 16B presents another example activity dashboard UI 1611 that can generated and presented via the user interface component 1510 and/or the dashboard reporting component 570. In this example, the activity dashboard UI 1611 presents graphical information 1610 regarding the number of studies received for processing per modality per a selected timeframe (e.g., the last 30 days in this example). The activity dashboard UI 6111 also includes a model summary section 1612 that includes information regarding the models run within the past 30 days. In this example, the model summary section 1612 identifies the respective models by name, identifies the provider, the total number of times the model was run and completed, the number of positive results (assuming these are diagnostic model), the number of negative results (assuming these are diagnostic models), and the number of failed executions.

Figure 17:
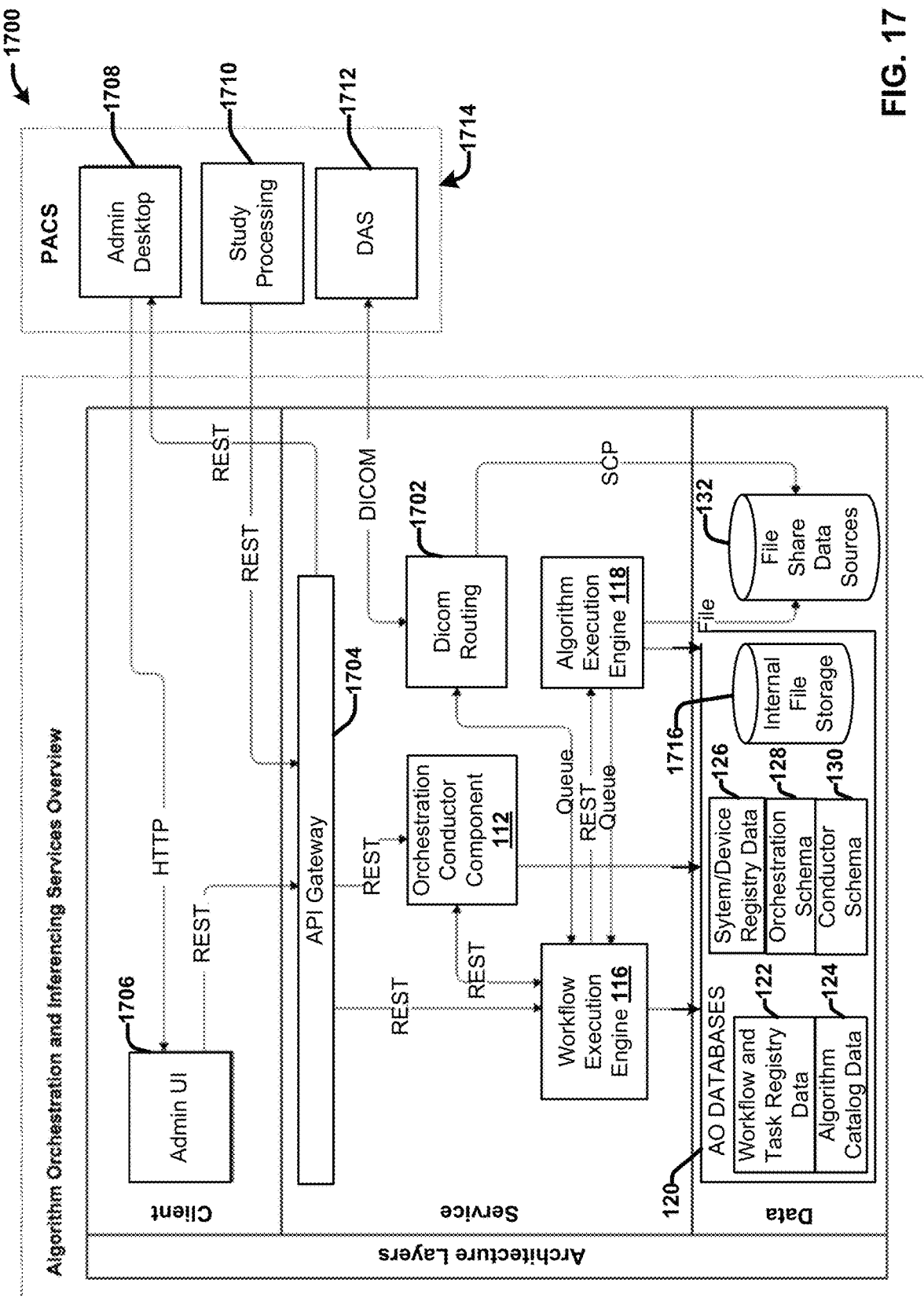
FIG. 17 presents an example algorithm orchestration system architecture in accordance with one or more embodiments of the disclosed subject matter.

FIG. 17 presents an example algorithm orchestration system architecture 1700 architecture in accordance with one or more embodiments of the disclosed subject matter. The system architecture 1700 provides an example architecture for implementing algorithm orchestration system 100 and/or algorithm orchestration system 300 in accordance with one or more examples of the disclosed subject matter. Repetitive description of like elements is omitted for sake of brevity.

In this example implementation, the architecture 1700 includes three layers, a data layer, a service layer and a client layer to execute the various orchestration components described herein including workflow development and processing. The data layer stores data for the services layer, including the data provided by the one or more AO databases 120, the file share data sources 132 and includes schemas for transporting files between the services layer and the data layer. The service layer includes the orchestration conductor component 112, the workflow execution engine 116 and the algorithm execution engine 118 and provides for executing the various workflows and algorithms provided in the data layer, includes a services layer to execute algorithm orchestration and the various algorithms described herein. The services layer also include a DICOM routing component 1702 that provides for transferring DICOM image files between and a direct-attached storage (DAS) 1712 element provided by a PACS 1714 and the workflow execution engine 116 and the algorithm execution engine 118. The DAS 1712 stores the medical images and metadata. The client layer includes an administrator user interface (UI) 1710 that for developing and executing workflows in accordance with an external PACS system 1714 that includes an administrator desktop 1708 (e.g., corresponding to the administrator device 104) that interacts with the administrator UI 1706 via an API gateway 1704 that provides an interface between the client layer and the services layer. The PACS system 714 also includes a study processing component 1710 for retrieving medical study data from the DAS 1712 for medical imaging analysis.

The API gateway 1704 interfaces with the orchestration conductor component 112 that orchestrates execution of the workflow execution engine 116 and the algorithm execution engine 118 as well as the various services provided by the algorithm orchestration component 110. The workflow execution engine 116 can communicate with the DICOM router 1702 that transfers image and metadata from the DAS 1712. The workflow execution engine 116 and the algorithm execution engine 118 can communicates the AO databases 120 and the file share data sources 132 to execute selected algorithms in accordance with the workflow instructions. In various embodiments, the data layer can operate as a structured query language (SQL) database and include an orchestration schema to interface to the orchestration services and an engine schema to interface to the orchestration conductor component 112. Various interface signals couple the components depicted in the system. These signals include queue signals, Representational State Transfer (REST) signals, and hypertext transfer protocol (HTTP) signals, and DICOM signals.

In an implementation example, when the PACS 1714 has a new study to be processed through the orchestration, this will send an HTTP request to a REST API exposed by the API Gateway 1704 called "study process notification" containing the study metadata in the payload. The API gateway 1704 will forward the request to the orchestration conductor component 112 that can validate the request payload and respond with an execution ID (e.g., a request ID) and a status. The orchestration conductor component 112 can direct the workflow exaction engine to invoke available/applicable workflows included in the workflow and task registry data 122. The respective workflows can be executed as a separate thread. Some workflows will start by validating the DICOM metadata to see if they match the workflow conditions (e.g., modality, view position, study description, and so forth) and, in case of a match, can transfer the study data from the PACS 1714 to an internal file storage 1716. When the transfer is completed, the algorithm execution engine 118 can execute the algorithms defined in the workflow. For each algorithm that is to be executed, the workflow execution engine 116 invokes the algorithm execution engine 118 and waits for a response. When the response of the selected algorithms is available, the orchestration conductor component 112 can transfer the output files produced by the algorithms back to the PACS 1714 and send a notification message indicating the processing of that study is complete. This notification message should also include the list of algorithms executed by the workflow execution engine 116 and the execution results for the respective algorithm selected.

Figure 18A:
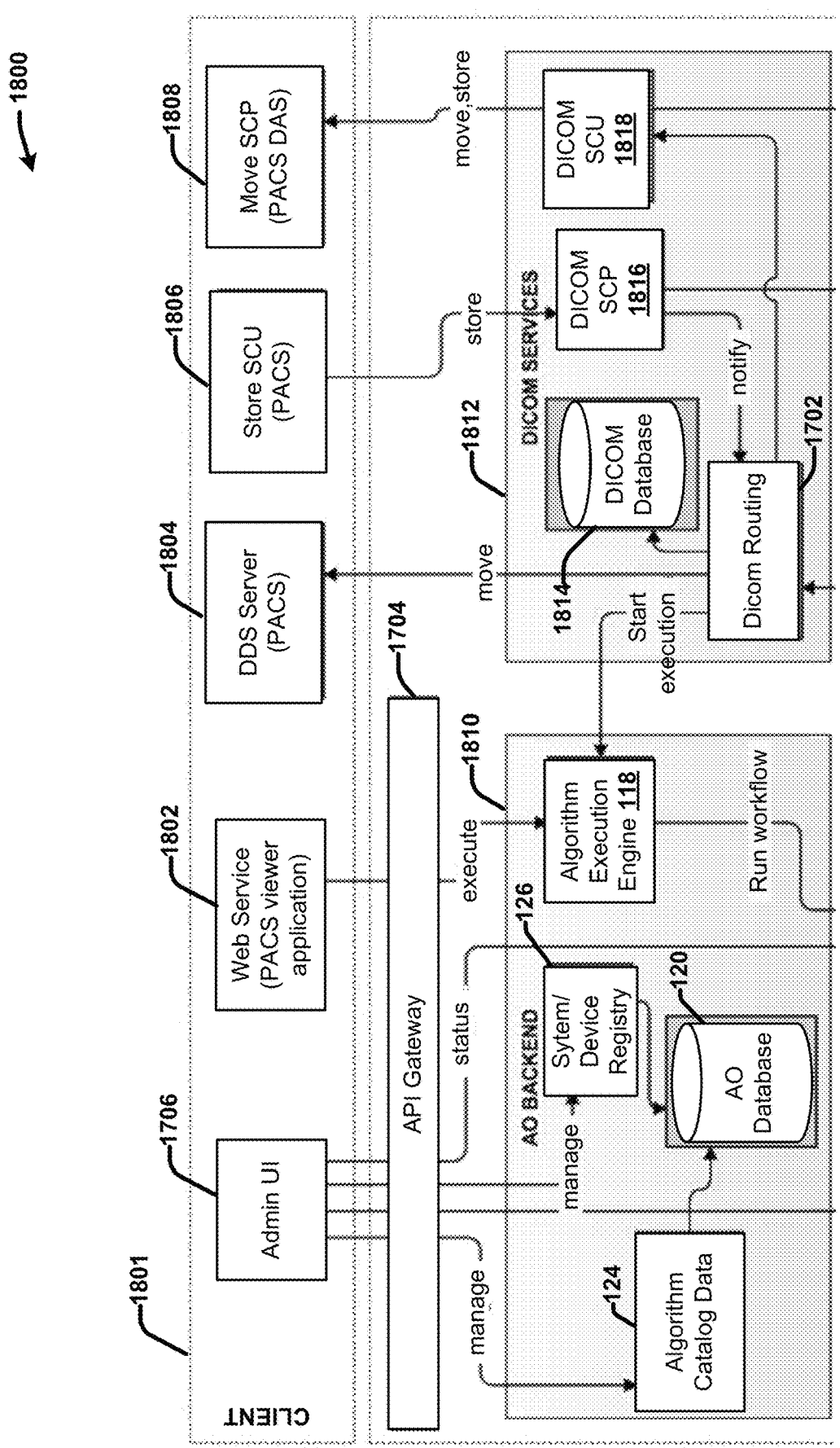
FIGS. 18A-18B present another example algorithm orchestration system architecture in accordance with one or more embodiments of the disclosed subject matter.
Figure 18B:
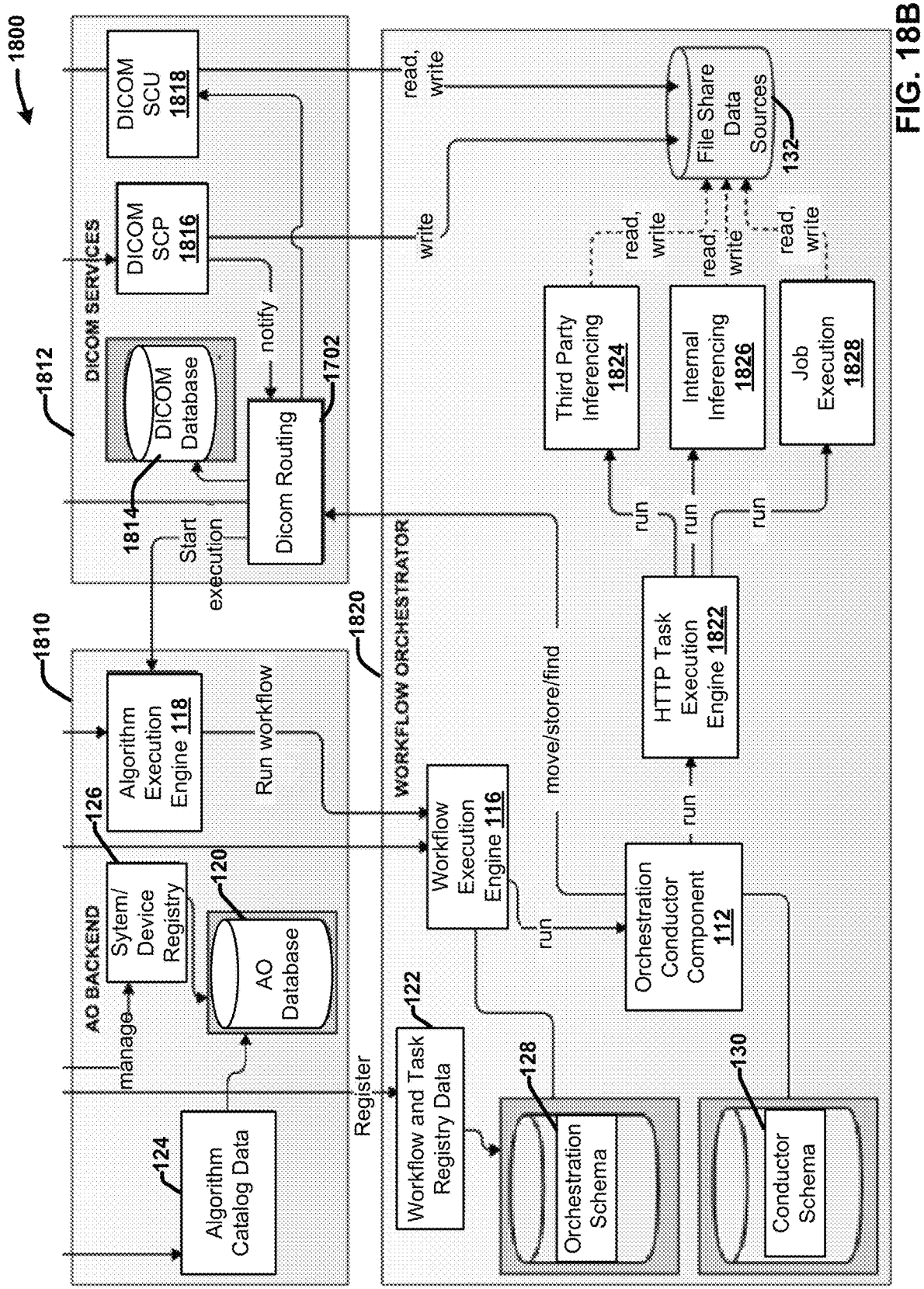

FIGS. 18A-18B present another example algorithm orchestration system architecture 1800 in accordance with one or more embodiments of the disclosed subject matter. The system architecture 1800 provides another example architecture for implementing algorithm orchestration system 100 and/or algorithm orchestration system 300 in accordance with one or more examples of the disclosed subject matter. Repetitive description of like elements is omitted for sake of brevity.

FIGS. 18A-18B present an example system architecture 1800 from the front end to the back end for users to access the system to initiate execution of workflows. In this example implementation, the system architecture 1800 includes four layers, a client layer 1802, an algorithm orchestration (AO) backend layer 1810, a DICOM services layer 1812, and layer a workflow orchestrator layer 1820. The client layer 1801 can include the administrator UI 1706, a web-service 1802 configured to interface with the API gateway (e.g., a PACS viewer with orchestration services), a data distribution service (DDS) server 1804, a store SCU 1806 and a move SCP 1808. There are different ways to start the same workflow execution depending on what APIs the client systems/devices support. In one implementation, the client system/device (e.g., a web-service client 1802) can send a web-service call (e.g., an HTTP call) through the API gateway 1704 to provide image processing requests. An administrator can also access the AO backend layer 1810 and the algorithm orchestrator layer 1820 via the administrator UI 1706 and the API gateway 1704.

The system architecture 1800 also supports accessing the AO backend layer 1810 and the orchestration layer 1820 via a DICOM services layer 1812. In this example, the DICOM services layer 1812 can include a DICOM database 1814 including the medical images to be processed via the workflows, the DICOM routing component 1702, a DICOM service class provider (SCP) 1816, and a DICOM service class user (SCU). This channel can be used by any DICOM compliant system to push a DICOM image/study to the AO backend layer 1810 and the workflow orchestrator layer 1820 to start the same workflow logic.

With this example implementation, the workflow execution starts at the workflow orchestrator layer 1820. When a client system/device calls the orchestrator through the web-service 1802, the channel comes through the AO backend layer 1810, which then invokes the algorithm execution engine 118, the workflow execution engine 116 and the HTTP task execution 1822 as orchestrated/conducted by the orchestration conductor component. In various embodiments, the HTTP task execution engine 1822 can be or correspond to a version of the algorithm execution engine 118 configured to handle execution of asynchronous HTTP workflow tasks and jobs defined in the file share data sources 132, including third-party inferencing tasks 1824 involving calling and running third-party inferencing models (e.g., third-party algorithms 136), internal inferencing tasks 1826 involving calling and running internal inferencing models (e.g., internal algorithms 134) and jobs execution tasks 1828. When a client system/device submits image processing requests 106 via the DICOM API, the (back-end) DICOM services layer 1812 will send a notification to the DICOM routing component 1702 which in turn will call the AO backend layer 1810 and eventually access the workflow orchestrator layer 1820.

Various operational commands/signals that describe the interaction between the respective system components are further provided. These operational commands/signals include: manage, status (notifications), execute, move, store, notify, start execution, run workflow, run, find, and read/write.

Figure 19:
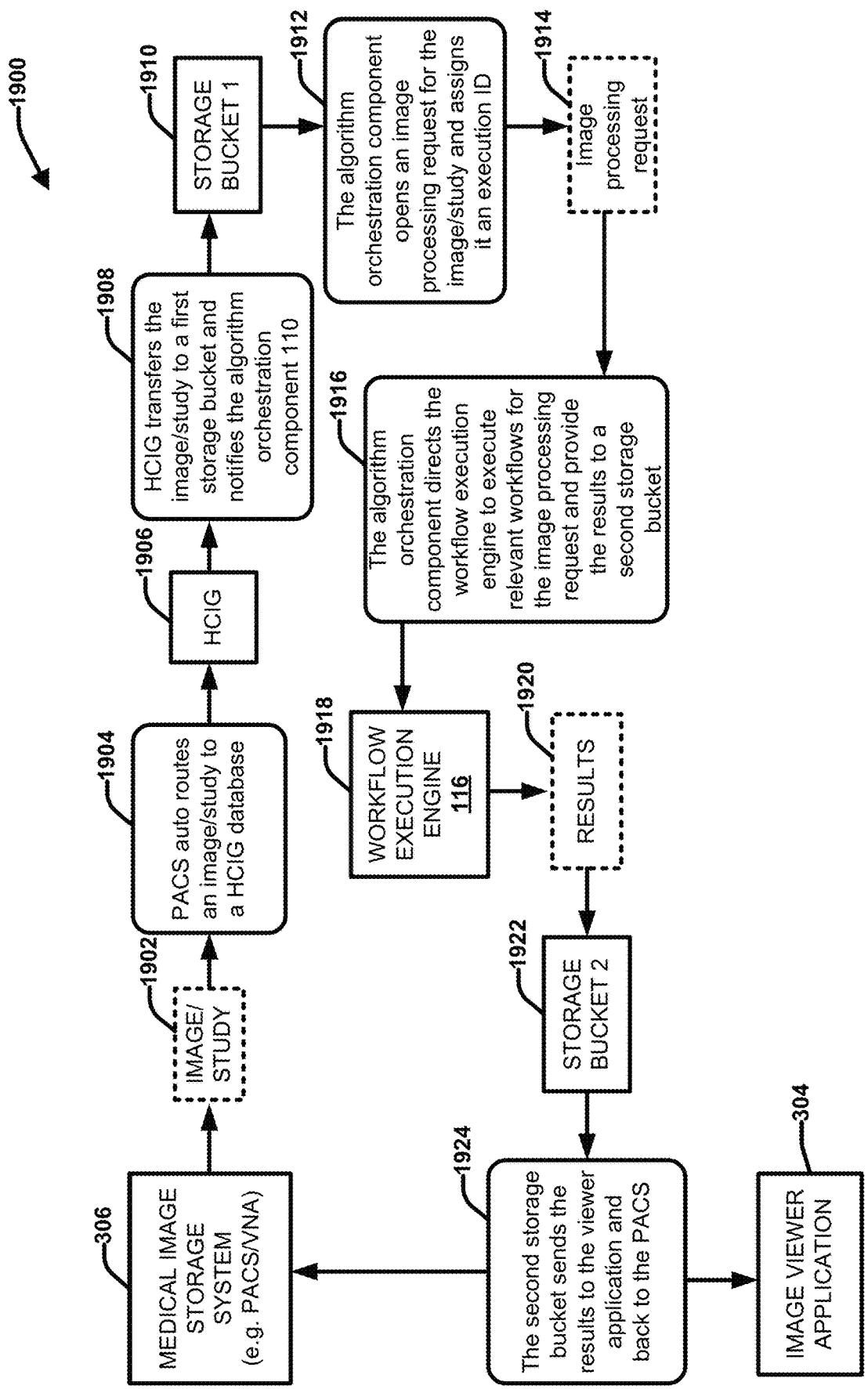
FIG. 19 illustrates a block diagram of a workflow process and computing stages for analyzing medical images and metadata in accordance with one or more embodiments of the disclosed subject matter.

FIG. 19 illustrates a block diagram of a workflow process 1900 and computing stages for analyzing medical images and metadata in accordance with one or more embodiments of the disclosed subject matter. In this example implementation, an image/study 1902 and associated metadata is passed from the medical image storage system 306 (e.g., a PACS, VNA or the like) to a health care interest group (HCIG) database and processor for preprocessing and formatting before passing the image/study on to a first storage bucket 1910. In this regard, at 1904, the PACS can auto route the image/study the HCIG database. At 1908, the HCIG database transfers the image/study to a first storage bucket 1910 and notifies the algorithm orchestration component 110. At 1912, the algorithm orchestration component opens an image processing request 1914 for the image/study and assigns it an execution ID. At 1916, the algorithm orchestration component directs the workflow execution engine 116 to execute relevant workflows for the image processing request and provide the results 1920 to a second storage bucket 1922. The results 1920 from the storage bucket can be viewed using an image viewer application 304 which can also be passed back as results feedback to the medical image storage system 306 (i.e., a PACS). In this regard, at 1924, the second storage bucket sends the results to the viewer application and back to the PACS.

Figure 20:
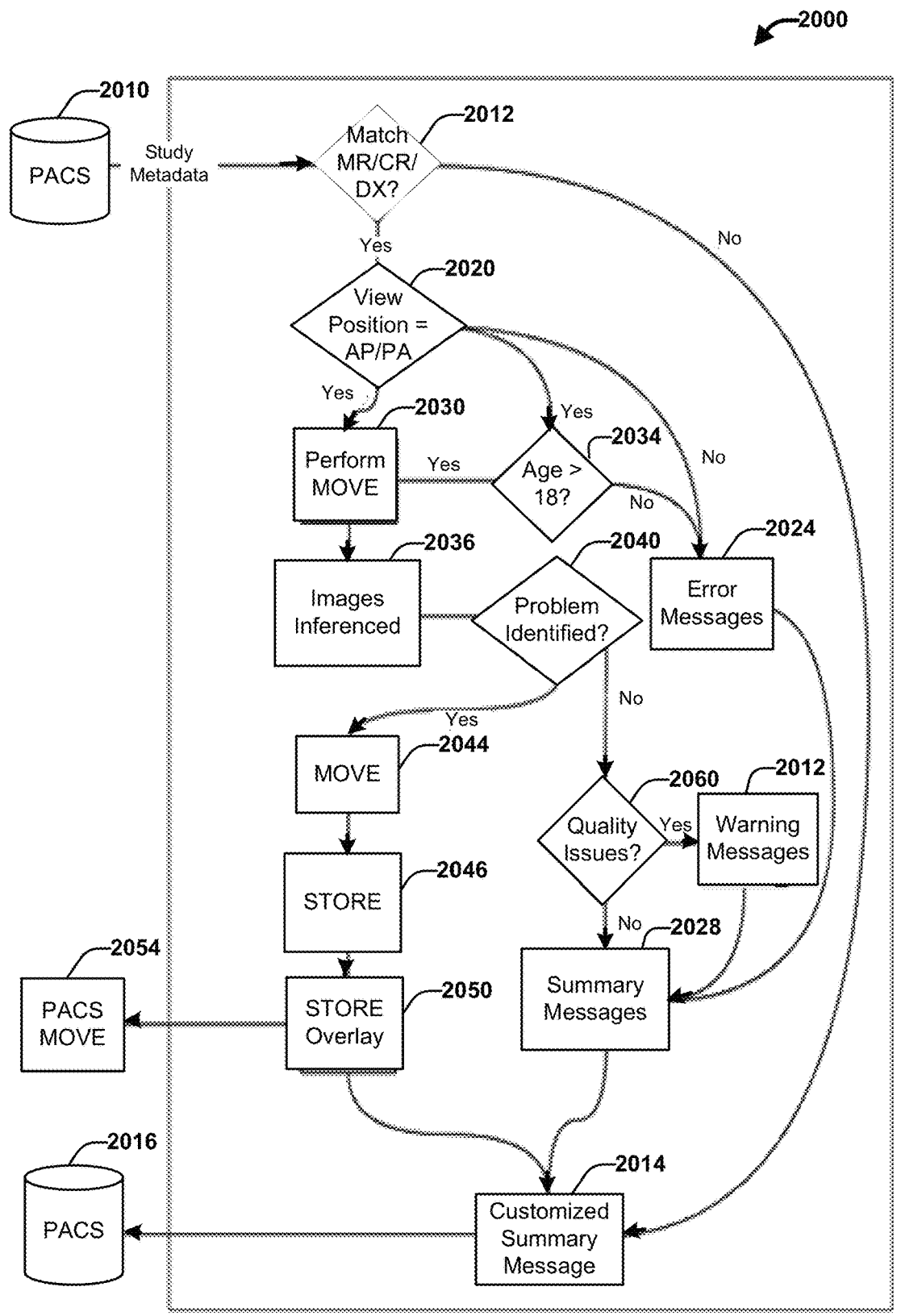
FIG. 20 is an example of a workflow process as executed by an algorithm orchestration component and its interactions with other components of the workflow in accordance with one or more embodiments of the disclosed subject matter.

FIG. 20 is an example of a workflow process 2000 as executed by the algorithm orchestration component 110 and its interactions with other components of the workflow in accordance with one or more embodiments of the disclosed subject matter. At 2010, study metadata is retrieved from the PACS (e.g., by the orchestration conductor component 112) and a decision performed at 2012 to determine if the study matches a first workflow/algorithm criterion (e.g., whether the modality is MR/CR/DX). If false at 2012, the process 2000 proceeds to 2014 where a customized summary message is generated that is provided back to another PACS 216. If true at 2012, the process proceeds to 2020. At 2020, the process performs another decision to determine whether the image satisfies a second decision criterion (e.g., whether the view position is AP/PA). If false at 2020, the process proceeds to 2024 and generates an error message and then proceeds to 2028 and generates a summary message. If true at 2020, the process proceeds in parallel to 2030 and 2034. At 2030, the process performs a move operation followed by inferencing the images at 2036. At 2034, a decision is made as to the patient's age. If not greater than age 18 at 2034, the process proceeds to 2024 and generates an error message. If greater than age 18 at 2034, the process proceeds to 2030.

After inferencing at 2036, the process proceeds to 2040 where a determination is made whether a given medical problem has been identified. If yes at 2040, the process proceeds to 2044 and performs a move operation, followed by a store operation at 2046, and subsequently followed by a store overlay operation at 2050 which ends as a PACS move at 2054. If the medical problem was not identified at 2040, the process proceeds to 2060 where quality metrics are run to determine the quality of the medical decision determined by the inferencing engine at 2036. If suitable quality, the process proceeds to 2064 and generates a warning message before proceeding to 2028. If quality metrics are not suitable, the process proceeds to 2028 and generates a summary message indicating the problem could not be detected.

Figure 21:
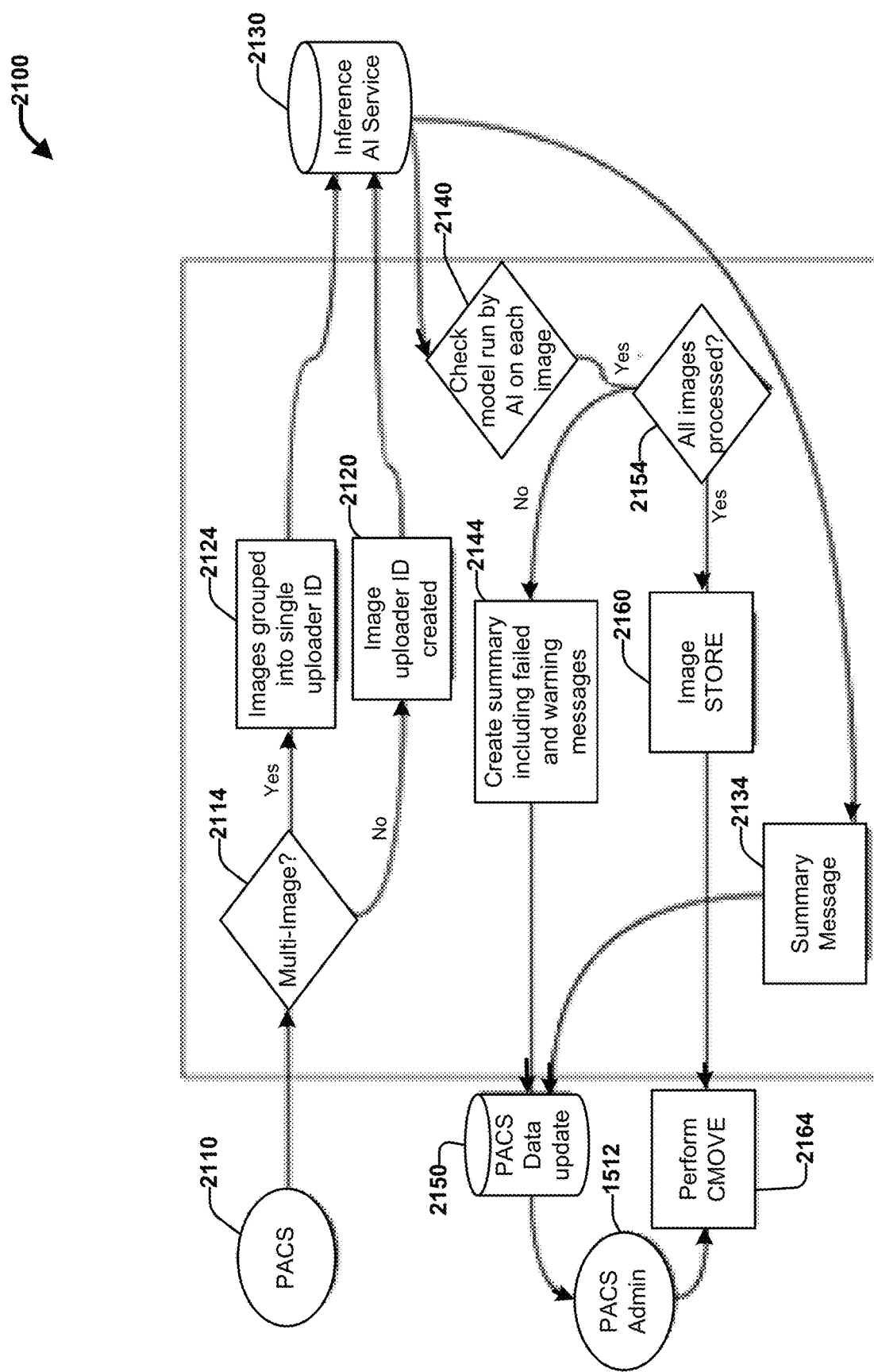
FIG. 21 is an example of an algorithm management process as executed by an algorithm management component and its interactions with other components of the process in accordance with one or more embodiments of the disclosed subject matter.

FIG. 21 is an example of an algorithm management process 2100 as executed by an algorithm management component and its interactions with other components of the process in accordance with one or more embodiments of the disclosed subject matter. At 2110, a PACS acquisition for a medical image (or images) us initiated where a determination is performed at 2114 whether multiple images are involved (e.g., a study/series). If a single image is acquired at 2114, the process proceeds to 2120 an image uploader identifier is created. If multiple images are detected at 2114, the images are grouped into a single uploader identifier at 2124. After the identifiers are created at 2120 and 2124 respectively, the process proceeds to an inference AI service, which corresponds to usage of the workflow execution engine 116 and the algorithm execution engine 118 to execute one or more AI models on the image data in accordance with one or more applicable workflows. Output from the AI service 2130 is fed to a summary message generator at 2134 and processed by a decision at 2140. At 2140, a determination is made whether to check the model run on each AI image. If no at 2130, the process proceeds to 2144 and creates a summary including failed and warning messages, followed by a PACS update at 2150. If yes at 2140, the process proceeds to 2154 where a determination is made whether all the image has been processed. If not at 2154, the process proceeds to 2144. If yes at 2154, the process proceeds to 2160 and performs a store to PACS of the image. Output of 2160 is fed to 2164 where a PACS move is performed. As shown, a PACS administrator has control over the components 2150 and 2164, respectively.

Figure 22:
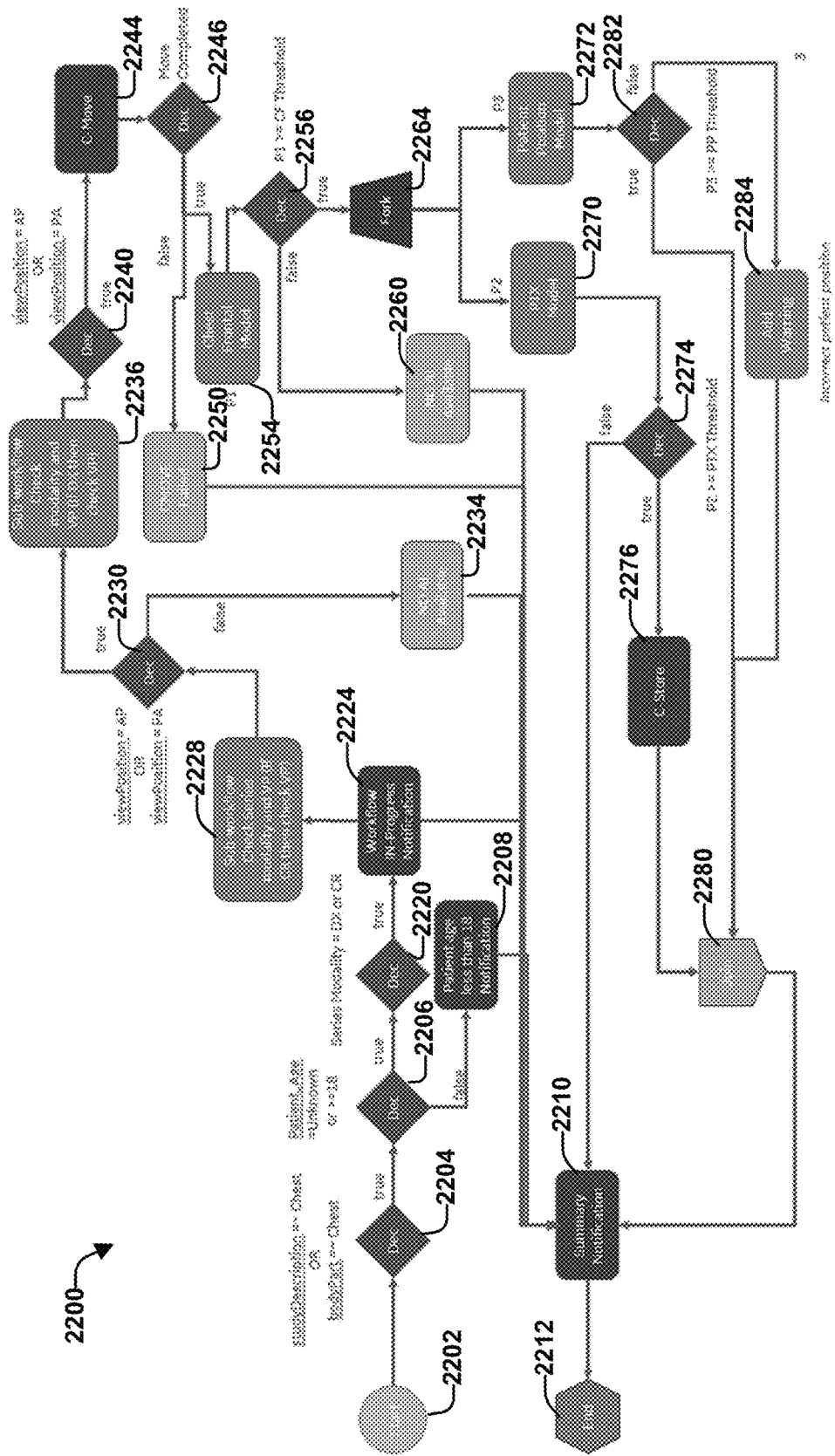
FIG. 22 illustrates an example of a workflow implementation analyzing a chest X-Ray for a pneumothorax (PTX) condition in accordance with one or more embodiments of the disclosed subject matter.

FIG. 22 illustrates an example of a workflow implementation 2200 analyzing a chest X-Ray for a pneumothorax (PTX) condition in accordance with one or more embodiments of the disclosed subject matter. At 2202, the workflow begins. At 2204, a decision decides if a study description of a chest or a chest image is to be analyzed. 2206, a decision is made as to whether the patient age is greater than or equal to 18. If not, the workflow 2200 proceeds to 2208 where a notification is generated indicating the patient is underage for the analysis of the workflow 2200. After 2208 the process 2200 proceeds to 2210 and generates a summary notification and then ends at 2212. If the decision is true at 2206, the process 2200 proceeds to 2220 where a decision is made as to the type of modality that captured the image (e.g., DX, CR). At 2224, the process 2200 generates a notification that the workflow is in process. At 2228, a sub workflow is executed to determine the modality and to perform a check if the modality was determined CR at 2220. At 2230, a decision is executed to determine whether the view position for the image was AP or PA. If either both false, the process proceeds to 2234 and generates a notification that no AI models are available.

If the decision is true at 2230, the process 2200 proceeds to 2236 and performs a sub workflow to check modality and VP. At 2240, a decision is made as to whether the view position is Ap or PA. If true, the process proceeds to 2244 and performs a move to transfer data. At 2246, the process 2200 proceeds to 2246 and determines if the move was completed. If false, the process 2200 proceeds 2250 where a notification is generated that the move failed. If true at 2246, the process proceeds to 2254 and runs a chest frontal model. After model execution at 2254, the process 2200 proceeds to 2256 where a decision is made as to whether the model analysis run at 2254 exceeds a probability threshold. If false at 2256, the process 2200 proceeds to 2260 and reports that no AI is available. If true at 2256, a fork instruction creates parallel model branches 2270 and 2272.

After a PTX model is executed at 2270, the process 2200 proceeds to 2274 where a decision is made as to the prediction made by the PTX model at 2270. If false (e.g., below a probability threshold), the process proceeds to 2210 and generates a summary notification of the false (non-positive) results. If true at 2274, the process proceeds to perform a store operation and ends at a join operation 2280. At branch 2272, a patient position model is executed in parallel to the branch at 2270. At 2282, a decision is made the patient position is greater than or equal to a patient position threshold. If true at 182, the branch ends at join 2280. If false at 2282, a warning is added at 2284 and the branch then ends at join 2280. Output from join 2280 is passed to 2210 where a summary notification (e.g., report) is generated.

Figure 23:
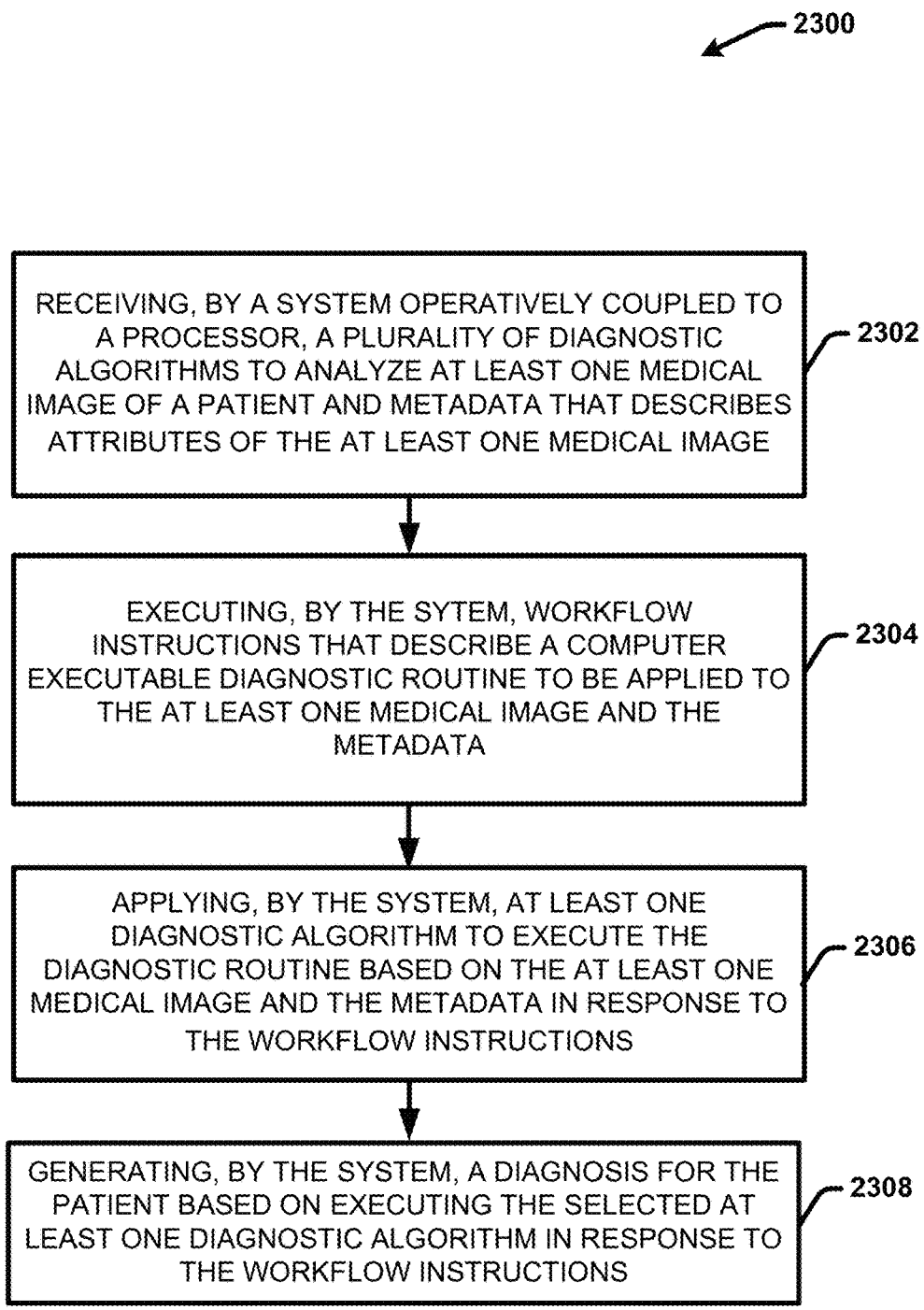
FIG. 23 presents a high-level flow diagram of another example computer implemented method for executing workflow instructions to analyze a medical image and associated metadata in accordance with one or more embodiments of the disclosed subject matter.

FIG. 23 presents a high-level flow diagram of another example computer implemented method 2300 for executing workflow instructions to analyze a medical image and associated metadata in accordance with one or more embodiments of the disclosed subject matter. At 2302, the method 2300 includes receiving, by a system operatively coupled to a processor (e.g., system 100, system 300, system 1700, system 1800 and the like), a plurality of diagnostic algorithms to analyze at least one medical image of a patient and metadata that describes attributes of the at least one medical image (e.g., via the algorithm orchestration component 110). At 2304, the method 2300 includes executing, by the system, workflow instructions that describe a computer executable diagnostic routine to be applied to the at least one medical image and the metadata (e.g., via the workflow execution engine 116). At 2306, method 2300 includes applying, by the system, at least one diagnostic algorithm to execute the diagnostic routine based on the at least one medical image and the metadata in response to the workflow instructions (e.g., by the algorithm execution engine 118). At 2308, method 2300 includes generating, by the system, a diagnosis (e.g., wherein the algorithm results include a diagnosis) for the patient based on executing the selected at least one diagnostic algorithm in response to the workflow instructions.

Figure 24:
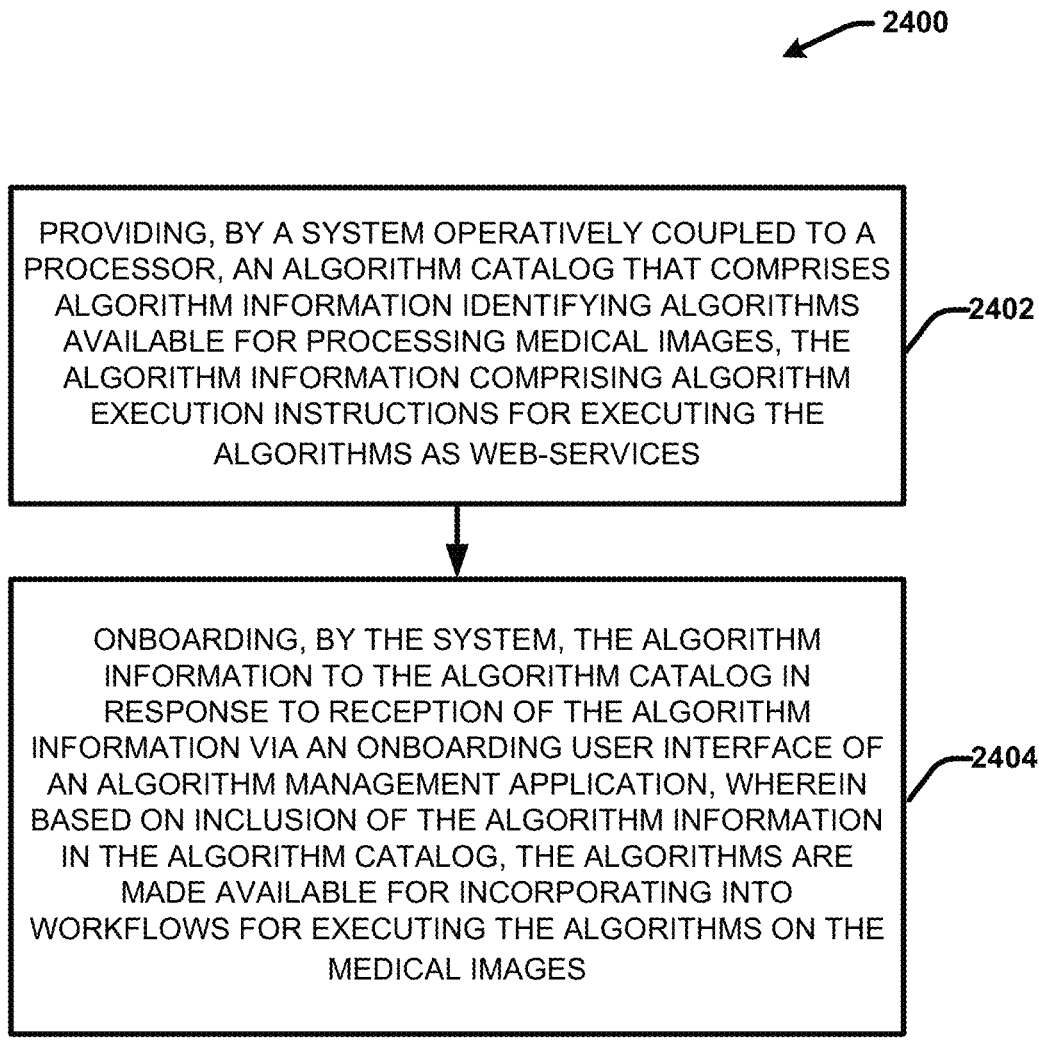
FIG. 24 presents a high-level flow diagram of an example computer implemented method for workflow algorithm management in accordance with one or more embodiments of the disclosed subject matter.

FIG. 24 presents a high-level flow diagram of an example computer implemented method 2400 for workflow algorithm management in accordance with one or more embodiments of the disclosed subject matter.

At 2402, a system operatively coupled to a processor (e.g., system 100, system 300, system 1700, system 1800, or the like), provides an algorithm catalog (e.g., algorithm catalog data 124) that comprises algorithm information identifying algorithms available for processing medical images, the algorithm information comprising algorithm execution instructions for executing the algorithms as webservices. At 2404, the system onboards (e.g., via onboarding component 518) the algorithm information to the algorithm catalog in response to reception of the algorithm information via an onboarding user interface (e.g., algorithm onboarding UI 901) of an algorithm management application (e.g., an algorithm management application that provides the management tools 114), wherein based on inclusion of the algorithm information in the algorithm catalog, the algorithms are made available (e.g., by the algorithm orchestration component 110) for incorporating into workflows (e.g., workflows included in the workflow and task registry data 122) for executing the algorithms on the medical images.

Figure 25:
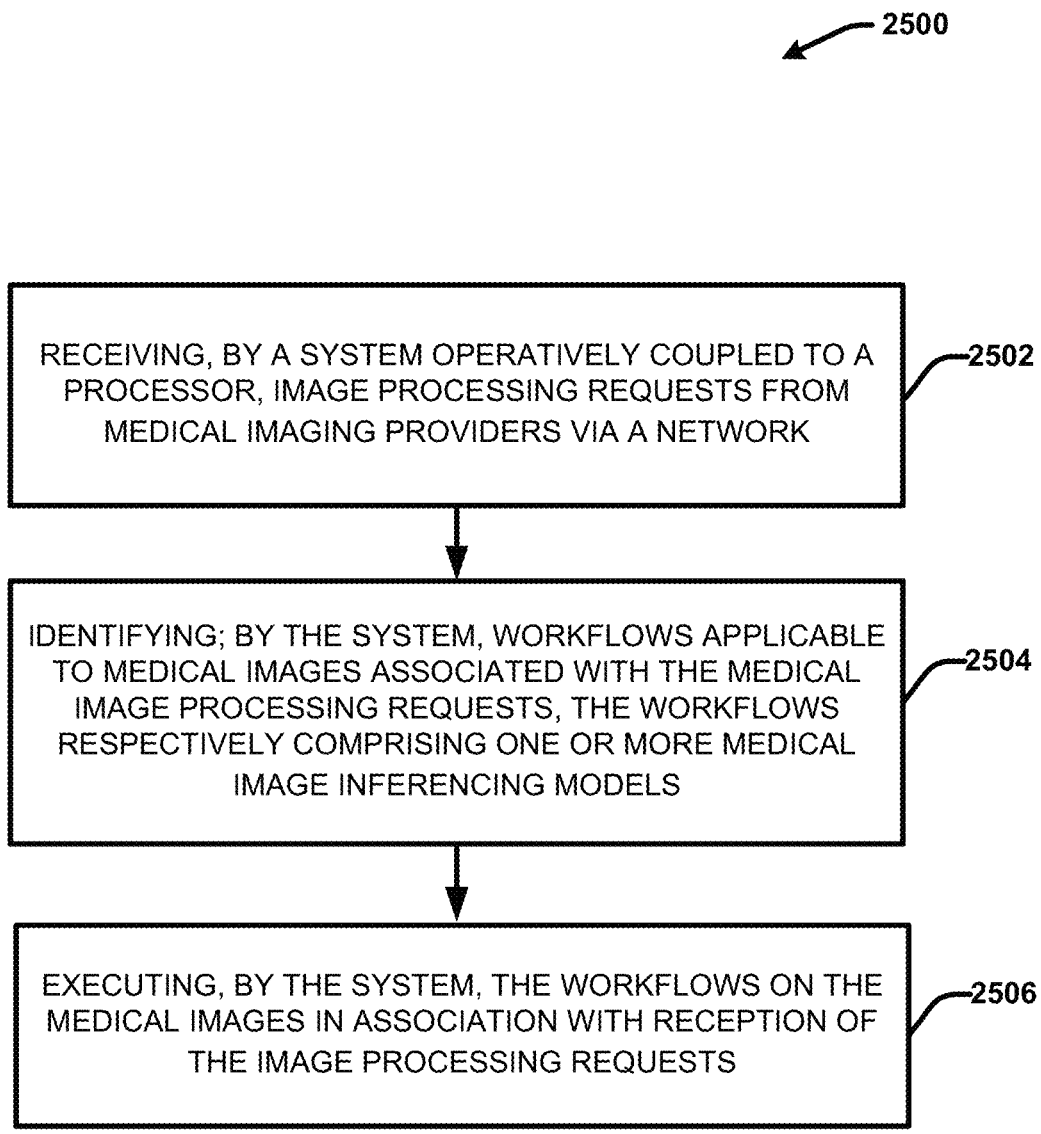
FIG. 25 presents a high-level flow diagram of an example computer implemented method for orchestrating execution of algorithms on medical images according to pre-defined workflows in accordance with one or more embodiments of the disclosed subject matter.

FIG. 25 presents a high-level flow diagram of an example computer implemented method 2500 for orchestrating execution of algorithms on medical images according to pre-defined workflows in accordance with one or more embodiments of the disclosed subject matter.

At 2502, a system operatively coupled to a processor (e.g., system 100, system 300, system 1700, system 1800 and the like), receives image processing requests from medical imaging providers via a network (e.g., via algorithm orchestration component 110). At 2504, the system identifies (e.g., via orchestration conductor component 112 and/or workflow execution engine 116) workflows applicable to medical images associated with the medical image processing requests, the workflows respectively comprising one or more medical image inferencing models (e.g., one or more internal algorithms 134 and/or one or more third party algorithms 136). At 2506, the system executes the workflows on the medical images in association with reception of the image processing requests (e.g., using workflow execution engine 116 and/or algorithm execution engine 118).

Figure 26:
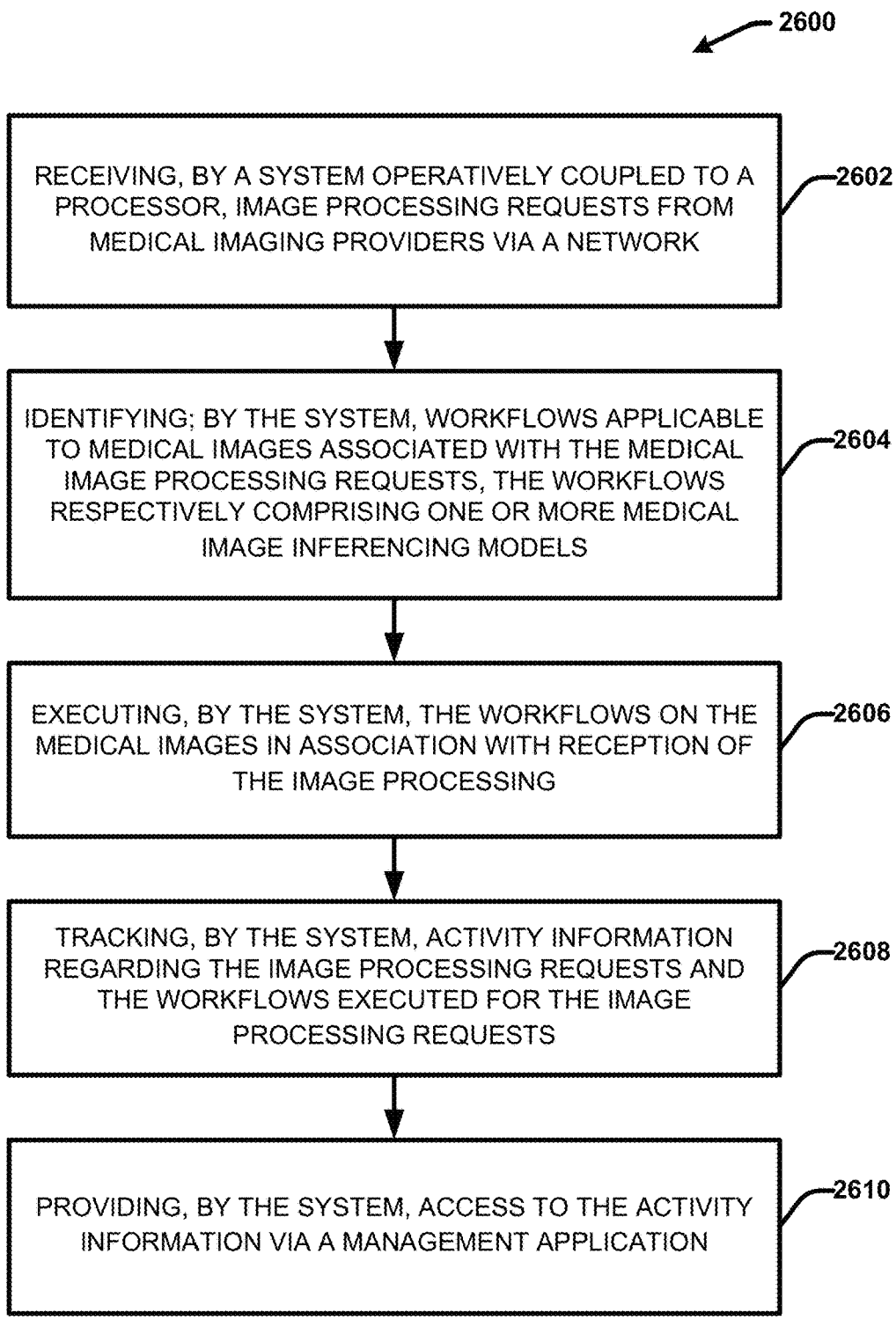
FIG. 26 presents a high-level flow diagram of an example computer implemented method for orchestrating execution of algorithms on medical images according to pre-defined workflows and managing workflow and model execution in accordance with one or more embodiments of the disclosed subject matter.

FIG. 26 presents a high-level flow diagram of an example computer implemented method 2600 for orchestrating execution of algorithms on medical images according to pre-defined workflows and managing workflow and model execution in accordance with one or more embodiments of the disclosed subject matter.

At 2602, a system operatively coupled to a processor (e.g., system 100, system 300, system 1700, system 1800 and the like), receives image processing requests from medical imaging providers via a network (e.g., via algorithm orchestration component 110). At 2604, the system identifies (e.g., via orchestration conductor component 112 and/or workflow execution engine 116) workflows applicable to medical images associated with the medical image processing requests, the workflows respectively comprising one or more medical image inferencing models (e.g., one or more internal algorithms 134 and/or one or more third party algorithms 136). At 2606, the system executes the workflows on the medical images in association with reception of the image processing requests (e.g., using workflow execution engine 116 and/or algorithm execution engine 118). At 2608, the system tracks activity information regarding the image processing requests and the workflows executed for the image processing requests (e.g., via activity logging component 564). At 2610, the system provides access to the activity information via a management application 2610 (e.g., an algorithm management application that provides the management tools 114).

One or more examples can be a system, a method, and/or a computer program product at any possible technical detail level of integration. The computer program product can include a computer readable storage medium (or media) having computer readable program instructions thereon for causing a processor to carry out one or more aspects of the present examples.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the entity's computer, partly on the entity's computer, as a stand-alone software package, partly on the entity's computer and partly on a remote computer or entirely on the remote computer or server. In the latter scenario, the remote computer can be connected to the entity's computer through any type of network, including a local area network (LAN) or a wide area network (WAN), or the connection can be made to an external computer (for example, through the Internet using an Internet Service Provider). In some examples, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to examples of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various examples of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 27, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 27:
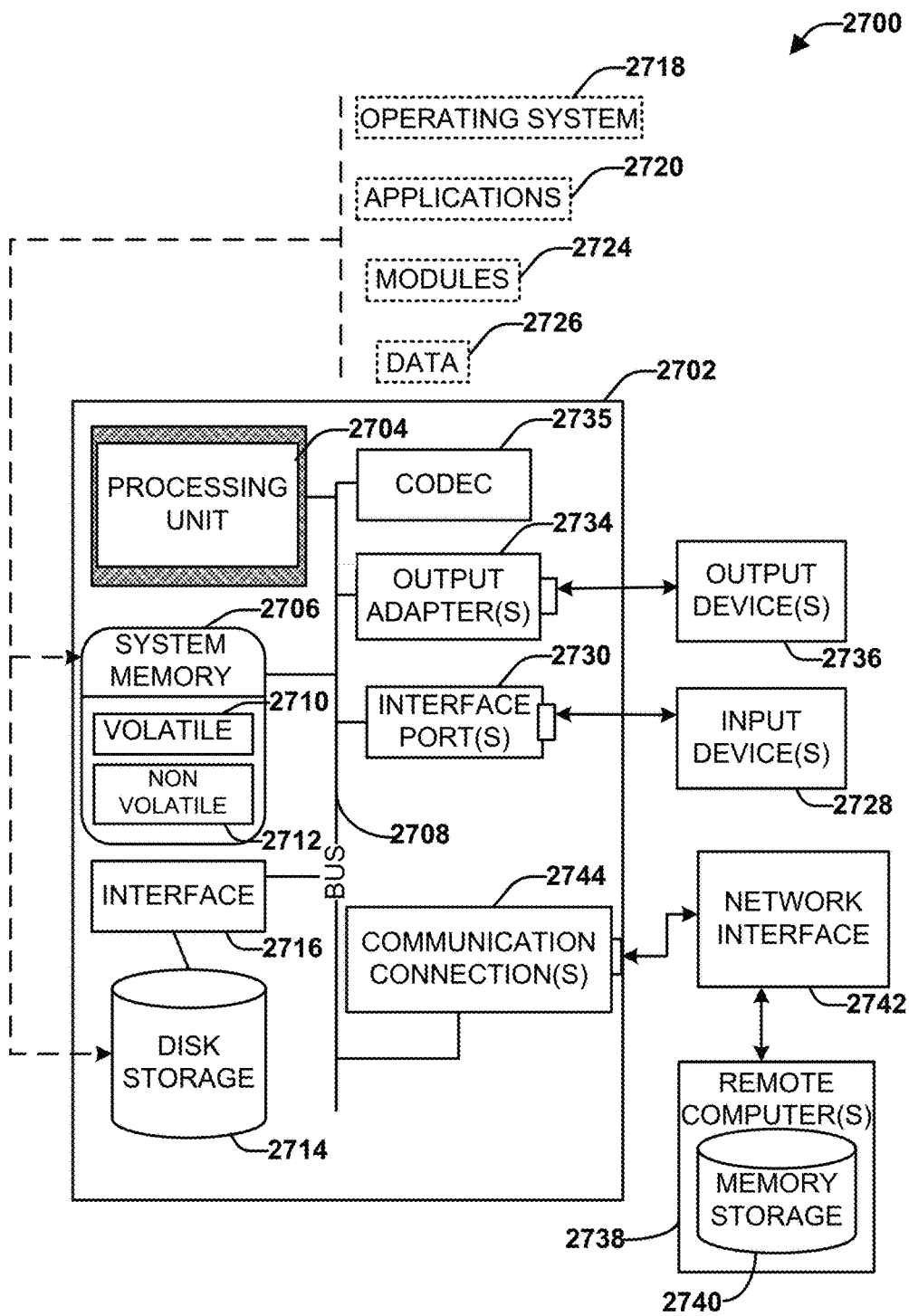
FIG. 27 illustrates a block diagram of an example, non-limiting operating environment in which one or more examples described herein can be facilitated.

With reference to FIG. 27, an example environment 2700 for implementing various aspects of the claimed subject matter includes a computer 2702. The computer 2702 includes a processing unit 2704, a system memory 2706, a codec 2735, and a system bus 2708. The system bus 2708 couples system components including, but not limited to, the system memory 2706 to the processing unit 2704. The processing unit 2704 can be any of various available processors. Dual microprocessors and other multiprocessor architectures also can be employed as the processing unit 2704.

The system bus 2708 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13154), and Small Computer Systems Interface (SCSI).

The system memory 2706 includes volatile memory 2710 and non-volatile memory 2712, which can employ one or more of the disclosed memory architectures, in various examples. The basic input/output system (BIOS), containing the basic routines to transfer information between elements within the computer 2702, such as during start-up, is stored in non-volatile memory 2712. In addition, according to present innovations, codec 2735 can include at least one of an encoder or decoder, wherein the at least one of an encoder or decoder can consist of hardware, software, or a combination of hardware and software. Although, codec 2735 is depicted as a separate component, codec 2735 can be contained within non-volatile memory 2712. By way of illustration, and not limitation, non-volatile memory 2712 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 2712 can employ one or more of the disclosed memory devices, in at least some examples. Moreover, non-volatile memory 2712 can be computer memory (e.g., physically integrated with computer 2702 or a mainboard thereof), or removable memory. Examples of suitable removable memory with which disclosed examples can be implemented can include a secure digital (SD) card, a compact Flash (CF) card, a universal serial bus (USB) memory stick, or the like. Volatile memory 2710 includes random access memory (RAM), which acts as external cache memory, and can also employ one or more disclosed memory devices in various examples. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 2702 can also include removable/non-removable, volatile/non-volatile computer storage medium. FIG. 27 illustrates, for example, disk storage 2714. Disk storage 2714 includes, but is not limited to, devices like a magnetic disk drive, solid state disk (SSD), flash memory card, or memory stick. In addition, disk storage 2714 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 2714 to the system bus 2708, a removable or non-removable interface is typically used, such as interface 2716. It is appreciated that disk storage 2714 can store information related to an entity. Such information might be stored at or provided to a server or to an application running on an entity device. In one example, the entity can be notified (e.g., by way of output device(s) 2736) of the types of information that are stored to disk storage 2714 or transmitted to the server or application. The entity can be provided the opportunity to opt-in or opt-out of having such information collected or shared with the server or application (e.g., by way of input from input device(s) 2728).

It is to be appreciated that FIG. 27 describes software that acts as an intermediary between entities and the basic computer resources described in the suitable operating environment 2700. Such software includes an operating system 2718. Operating system 2718, which can be stored on disk storage 2714, acts to control and allocate resources of the computer system 2702. Applications 2720 take advantage of the management of resources by operating system 2718 through program modules 2724, and program data 2726, such as the boot/shutdown transaction table and the like, stored either in system memory 2706 or on disk storage 2714. It is to be appreciated that the claimed subject matter can be implemented with various operating systems or combinations of operating systems.

An entity enters commands or information into the computer 2702 through input device(s) 2728. Input devices 2728 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 2704 through the system bus 2708 via interface port(s) 2730. Interface port(s) 2730 include, for example, a serial port, a parallel port, a game port, and a universal serial bus (USB). Output device(s) 2736 use some of the same type of ports as input device(s) 2728. Thus, for example, a USB port can be used to provide input to computer 2702 and to output information from computer 2702 to an output device 2736. Output adapter 2734 is provided to illustrate that there are some output devices 2736 like monitors, speakers, and printers, among other output devices 2736, which require special adapters. The output adapters 2734 include, by way of illustration and not limitation, video and sound cards that provide a means of connection between the output device 2736 and the system bus 2708. It should be noted that other devices or systems of devices provide both input and output capabilities such as remote computer(s) 2738.

Computer 2702 can operate in a networked environment using logical connections to one or more remote computers, such as remote computer(s) 2738. The remote computer(s) 2738 can be a personal computer, a server, a router, a network PC, a workstation, a microprocessor based appliance, a peer device, a smart phone, a tablet, or other network node, and typically includes many of the elements described relative to computer 2702. For purposes of brevity, only a memory storage device 2740 is illustrated with remote computer(s) 2738. Remote computer(s) 2738 is logically connected to computer 2702 through a network interface 2742 and then connected via communication connection(s) 2744. Network interface 2742 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 2744 refers to the hardware/software employed to connect the network interface 2742 to the bus 2708. While communication connection 2744 is shown for illustrative clarity inside computer 2702, it can also be external to computer 2702. The hardware/software necessary for connection to the network interface 2742 includes, for exemplary purposes only, internal and external technologies such as, modems including regular telephone grade modems, cable modems and DSL modems, ISDN adapters, and wired and wireless Ethernet cards, hubs, and routers.

The illustrated aspects of the disclosure may also be practiced in distributed computing environments where certain tasks are performed by remote processing devices that are linked through a communications network. In a distributed computing environment, program modules can be located in both local and remote memory storage devices.

Figure 28:
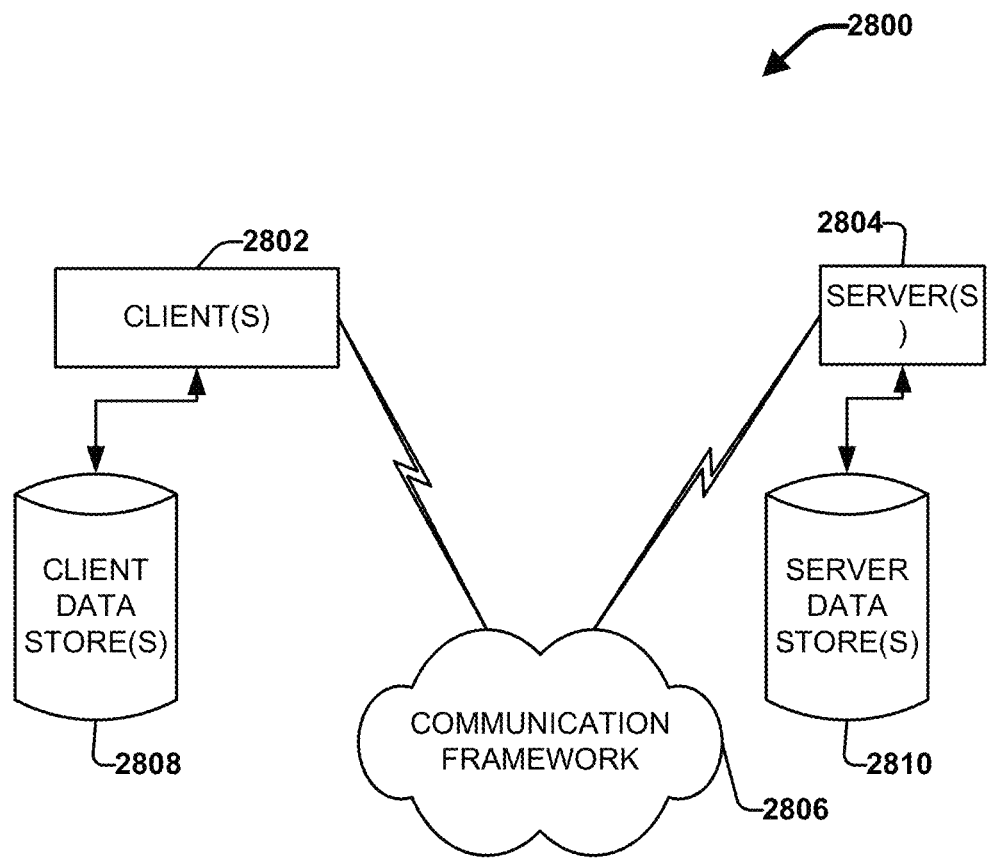
FIG. 28 illustrates a block diagram of another example, non-limiting operating environment in which one or more examples described herein can be facilitated.

Referring to FIG. 28, there is illustrated a schematic block diagram of a computing environment 2800 in accordance with this disclosure in which the subject systems (e.g., systems 100, 300, 1700, 1800 and the like), methods and computer readable media can be deployed. The computing environment 2800 includes one or more client(s) 2802 (e.g., laptops, smart phones, PDAs, media players, computers, portable electronic devices, tablets, and the like). The client(s) 2802 can be hardware and/or software (e.g., threads, processes, computing devices). The computing environment 2800 also includes one or more server(s) 2804. The server(s) 2804 can also be hardware or hardware in combination with software (e.g., threads, processes, computing devices). The servers 2804 can house threads to perform transformations by employing aspects of this disclosure, for example. In various examples, one or more components, devices, systems, or subsystems of system 1800, 2200 and 2400, can be deployed as hardware and/or software at a client 2802 and/or as hardware and/or software deployed at a server 2804. One possible communication between a client 2802 and a server 2804 can be in the form of a data packet transmitted between two or more computer processes wherein the data packet may include healthcare related data, training data, AI models, input data for the AI models and the like. The data packet can include a metadata, e.g., associated contextual information, for example. The computing environment 2800 includes a communication framework 2806 (e.g., a global communication network such as the Internet, or mobile network(s)) that can be employed to facilitate communications between the client(s) 2802 and the server(s) 2804.

Communications can be facilitated via a wired (including optical fiber) and/or wireless technology. The client(s) 2802 include or are operatively connected to one or more client data store(s) 2808 that can be employed to store information local to the client(s) 2802 (e.g., associated contextual information). Similarly, the server(s) 2804 are operatively include or are operatively connected to one or more server data store(s) 2810 that can be employed to store information local to the servers 2804.

In one example, a client 2802 can transfer an encoded file, in accordance with the disclosed subject matter, to server 2804. Server 2804 can store the file, decode the file, or transmit the file to another client 2802. It is to be appreciated, that a client 2802 can also transfer uncompressed file to a server 2804 and server 2804 can compress the file in accordance with the disclosed subject matter. Likewise, server 2804 can encode video information and transmit the information via communication framework 2806 to one or more clients 2802.

Figure 29:
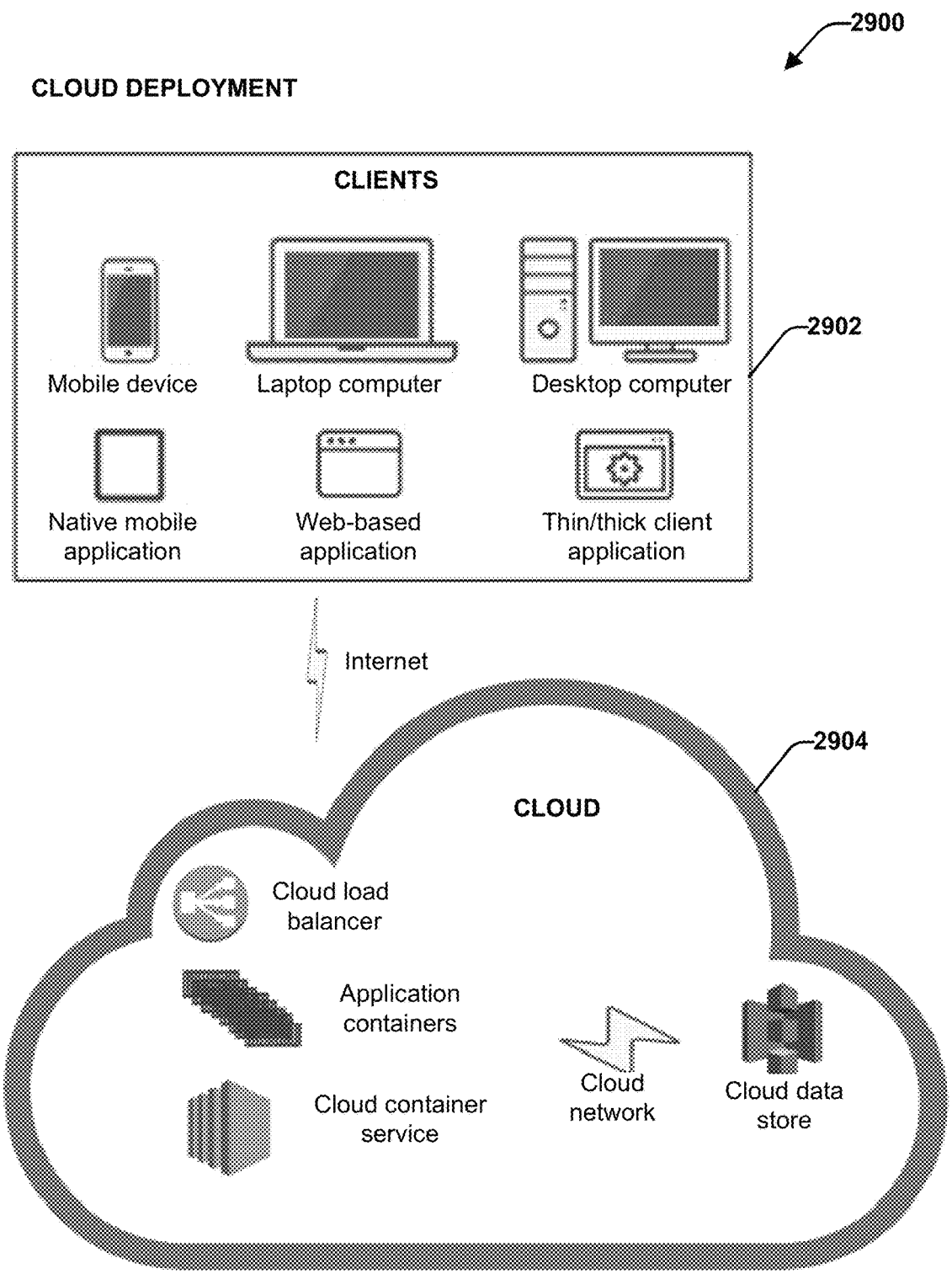
FIG. 29 illustrates a block diagram of another example, non-limiting operating environment in which one or more examples described herein can be facilitated.

FIG. 29 illustrates a schematic block diagram of another example computing environment 2900 in accordance with this disclosure in which the subject systems (e.g., systems 100, 300, 1700, 1800 and the like), methods and computer readable media can be deployed. The computing environment 2900 includes a cloud deployment architecture consisting of one or more clients 2902 that can be communicatively coupled to a system cloud 2904 via a network (e.g., the Internet). The system cloud 2904 can include a cloud load balances, one or more application container, one or more cloud service containers, a cloud data store, and a cloud network that communicatively couples the one or more cloud components to the cloud data store. In accordance with the cloud deployment architecture, the clients 2902 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject native/reconstructed medical imaging systems (e.g., systems 100, 300, 1700, 1800 and the like) deployed in the system cloud 2904. In various implementations, the one or more components of systems 100, 300, 1700, 1800 can be distributed between the clients 2902 and the system cloud 2904.

Figure 30:
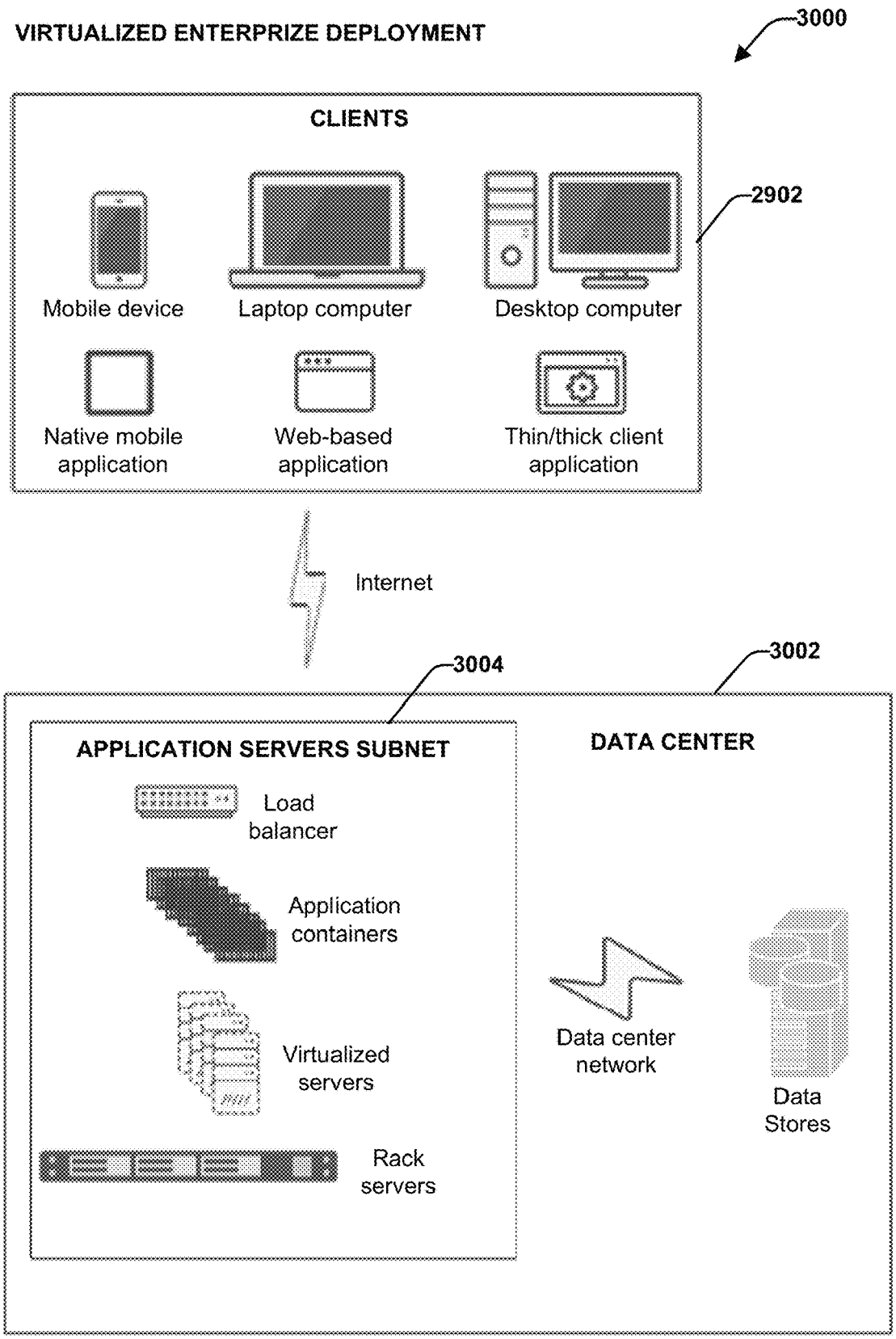
FIG. 30 illustrates a block diagram of another example, non-limiting operating environment in which one or more examples described herein can be facilitated.

FIG. 30 illustrates a schematic block diagram of another example computing environment 3000 in accordance with this disclosure in which the subject systems (e.g., systems 100, 300, 1700, 1800 and the like), methods and computer readable media can be deployed. The computing environment 3000 includes a virtualized enterprise deployment consisting of one or more clients 2902 that can be communicatively coupled to a remote data center 3002 via a network (e.g., the Internet). The remote data center 3002 can include an application servers subnet 3004 which can provide a load balancer, one or more application containers, one or more virtualized servers and one or more rack servers. The data center 3002 can also include one or more data stores that can be communicatively coupled to the application servers subnet 3004 via a data center network. In accordance with the virtualized enterprise deployment, the clients 2902 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject native/reconstructed medical imaging systems (e.g., system 100, 300, 1700, 1800 and the like) deployed in the data center 3002 and application servers subnet 3004. In various implementations, the one or more components of systems 100, 300, 1700, 1800 can be distributed between the clients 2902 and the application servers subnet 3004 and the data center 3002.

Figure 31:
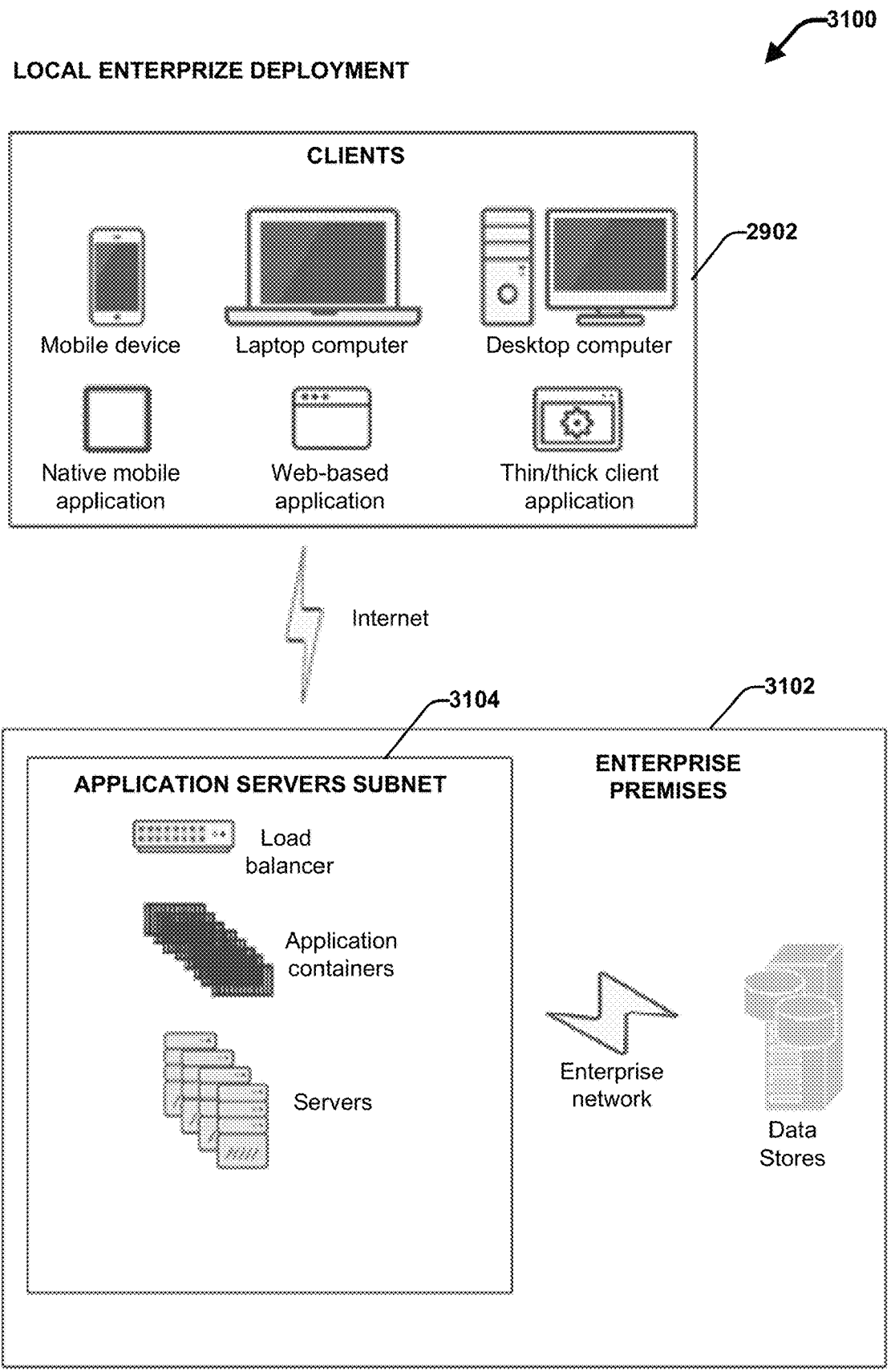
FIG. 31 illustrates a block diagram of another example, non-limiting operating environment in which one or more examples described herein can be facilitated.

FIG. 31 illustrates a schematic block diagram of another example computing environment 3100 in accordance with this disclosure in which the subject systems (e.g., systems 100, 300, 1700, 1800 and the like), methods and computer readable media can be deployed. The computing environment 3100 includes a local enterprise deployment consisting of one or more clients 2902 that can be communicatively coupled to an application servers subnet 3104 via a network (e.g., the Internet). In accordance with this example, the application servers subnet 3104 can be provided at the enterprise premises 3102 (e.g., as opposed to a remote data center 3102). The application servers subnet 3104 can include a load balancer, one or more application containers and one or more servers. The application servers subnet 3104 can be communicatively coupled to one or more data stores provided at the enterprise premises 3102 via an enterprise network. Similar to the cloud and virtualized enterprise deployments, the clients 2902 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject native/reconstructed medical imaging systems (e.g., systems 100, 300, 1700, 1800 and the like) deployed at the enterprise premises 3102 and the application servers subnet 3104. In various implementations, the one or more components of systems 100, 300, 1700, 1800 can be distributed between the clients 2902 and the application servers subnet 3104 and the enterprise premises 3102.

Figure 32:
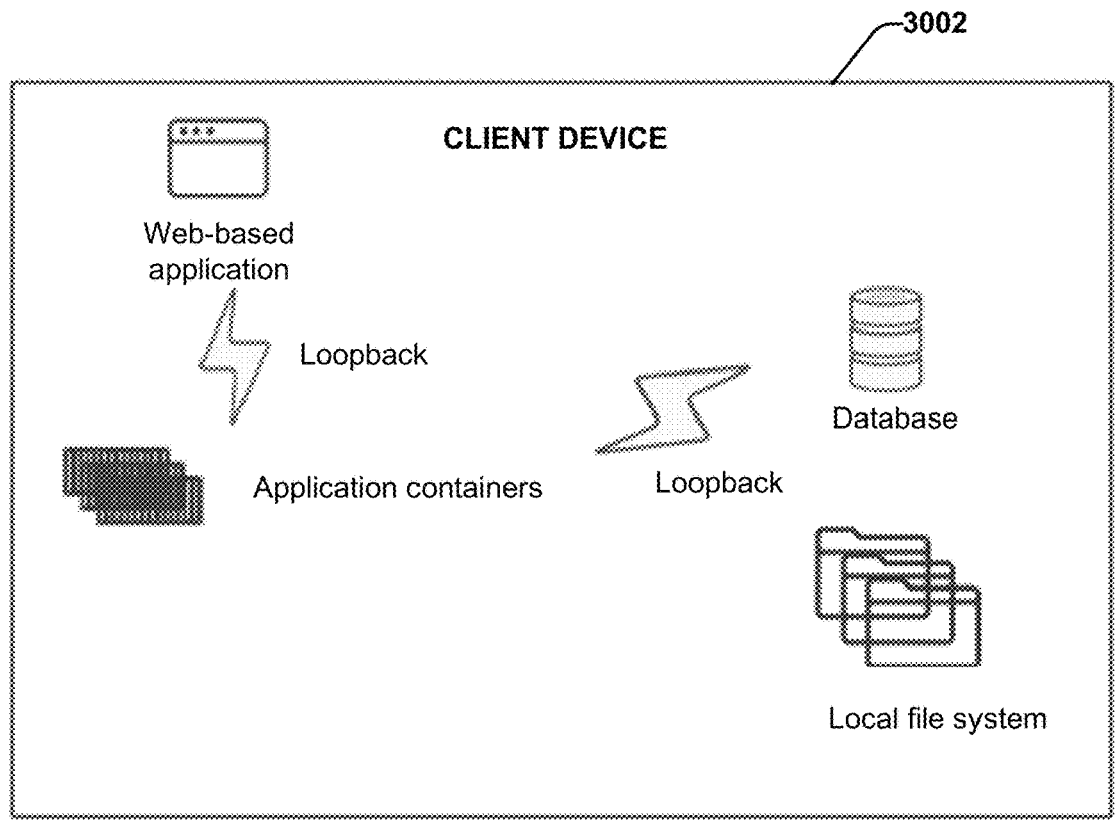
FIG. 32 illustrates a block diagram of another example, non-limiting operating environment in which one or more examples described herein can be facilitated.

FIG. 32 illustrates a schematic block diagram of another example computing environment 3200 in accordance with this disclosure in which the subject systems (e.g., systems 100, 300, 1700, 1800 and the like), methods and computer readable media can be deployed. The computing environment 3200 includes a local device deployment in which all of the components of system 100, 300, 1700 and 1800 are provided at a single client device 3202. With this implementation, the client device 3202 can include a web-based application which can be communicatively coupled via a loopback to one or more application containers. The one or more application containers can be communicatively coupled via a loopback to one or more databases and/or one or more local file systems.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "subsystem" "platform," "layer," "gateway," "interface," "service," "application," "device," and the like, can refer to and/or can include one or more computer-related entities or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various examples have been presented for purposes of illustration, but are not intended to be exhaustive or limited to the examples disclosed. Many modifications and variations can be apparent to those of ordinary skill in the art without departing from the scope and spirit of the described examples. The terminology used herein was chosen to best explain the principles of the examples, the practical application or technical improvement over technologies found in the marketplace, or to enable others of ordinary skill in the art to understand the examples disclosed herein.

What is claimed is:

1. A system, comprising:
a memory that stores computer-executable components; and
a processor that executes the computer-executable components stored in the memory, wherein the computer executable components comprise:
an algorithm catalog that comprises algorithm information identifying algorithms available for application to medical images, the algorithm information comprising algorithm execution instructions for executing the algorithms in association with invoking the algorithms at respective network accessible systems where the algorithms are stored; and
a workflow creation component that provides a workflow creation application that facilitates creating a workflow made available by the system for application to one or more of the medical images, the workflow comprising workflow information defining a set of computer-executable processing steps to be applied to the one or more of the medical images,
wherein the workflow creation application comprises a graphical user interface that facilitates creating the workflow using graphical nodes in association with receiving user input dragging and dropping the graphical nodes onto a workflow creation area of the graphical user interface, connecting the graphical nodes using one or more connection lines to define relationships between the graphical nodes, and configuring the graphical nodes, and
wherein the graphical nodes comprise different types of graphical nodes respectively corresponding to different types of computer-executable processing steps available for processing the medical images, including a task node corresponding to an algorithm execution task, wherein based on selection of the task node, the workflow creation application provides a selectable list of the algorithms included in the algorithm catalog and integrates a selected algorithm from the selectable list into the workflow in association with importing the algorithm execution instructions corresponding to the selected algorithm into the workflow information from the algorithm catalog, and
wherein the different types of graphical nodes are selected from the group consisting of: the task node, a decision node, a sub-workflow node, a wait node, a fork node, a join node and a function node.

2. The system of claim 1, wherein the computer-executable components further comprise:
a workflow execution component that controls execution of the workflow on the one or more medical images in association with reception of an image processing request from a medical image provider via a network and returns workflow results to the medical imaging provider generated in association with the execution of the workflow, the workflow results comprising output data of the selected algorithm.

3. The system of claim 2, wherein at least some of the algorithms employ a different format that is not compatible with the workflow execution component, and wherein the computer-executable components further comprise:
an onboarding component that adds the algorithm information to the algorithm catalog in response to reception of the algorithm information via an onboarding user interface of an algorithm management application, wherein based on inclusion of the algorithm information in the algorithm catalog, the system makes the algorithms available for incorporating into workflows created using the workflow creation application; and
a translation component that generates mapping information defining a mapping operation that controls translating between the different format and a format that is compatible with the workflow execution component in association with the onboarding, and wherein the onboarding component includes the mapping information with corresponding algorithm execution instructions for the at least some of the algorithms in the algorithm catalog.

4. The system of claim 3, wherein the workflow execution component employs the mapping information in association with controlling the application of the at least some of the algorithms.

5. The system of claim 1, wherein the algorithms comprise medical image inferencing models.

6. The system of claim 3, wherein the algorithms comprise medical image inferencing models, wherein the algorithm management application further provides for adjusting one or more parameters and thresholds of the algorithms in association with receiving the algorithm information, wherein the onboarding component stores settings information with the algorithm information defining the one or more parameters and thresholds, wherein the workflow execution component applies the settings information in association the execution of the algorithms, and wherein the thresholds include a criticality threshold for at least some of the medical image inferencing models.

7. The system of claim 1, wherein the computer-executable components further comprise:
a simulator component that runs the workflow in a test mode on one or more test images and identifies execution errors.

8. The system of claim 1, wherein the computer-executable components further comprise:
a workflow management component that provides, via an algorithm management application, access to collective workflow information defining workflows available by the system for application to the medical images, as created via the workflow creation application, and workflow management functions related to the workflows.

9. The system of claim 8, wherein the workflow management functions include an activation/deactivation function that provides for selectively activating and deactivating one or more of the workflows.

10. A method, comprising:
providing, by a system operatively coupled to a processor, an algorithm catalog that comprises algorithm information identifying algorithms available for application to medical images and algorithm execution instructions for executing the algorithms in association with invoking the algorithms at respective network accessible systems where the algorithms are stored; and
providing, by the system, a workflow creation application that facilitates creating workflows made available by the system for application to the medical images, the workflows respectively comprising workflow information defining a set of computer-executable processing steps to be applied to one or more of the medical images,
wherein the workflow creation application comprises a graphical user interface that facilitates creating the workflows using graphical nodes in association with receiving user input dragging and dropping the graphical nodes onto a workflow creation area of the graphical user interface, connecting the graphical nodes using one or more connection lines to define relationships between the graphical nodes, and configuring the graphical nodes, and
wherein the graphical nodes comprise different types of graphical nodes respectively corresponding to different types of computer-executable processing steps available for processing the medical images, including a task node corresponding to an algorithm execution task, wherein based on selection of the task node, the workflow creation application provides a selectable list of the algorithms included in the algorithm catalog and integrates a selected algorithm from the selectable list into the workflows in association with importing the algorithm execution instructions corresponding to the selected algorithm into the workflow information from the algorithm catalog, and
wherein the different types of graphical nodes are selected from the group consisting of: the task node, a decision node, a sub-workflow node, a wait node, a fork node, a join node and a function node.

11. The method of claim 10, further comprising:
storing, by the system, the workflows created using the workflow creation application;
receiving, by the system, image processing requests from medical imaging providers via a network;
controlling, by the system, execution of the workflows on the medical images in association with reception of image processing requests;
generating, by the system, workflow results based on the execution, the workflow results comprising outputs of respective algorithms integrated therein; and
returning, by the system, the workflow results to the medical imaging providers via the network.

12. The method of claim 10, wherein the algorithms comprise medical image inferencing models.

13. The method of claim 10, further comprising:
running, by the system, the workflows in a test mode on one or more test images; and
determining, by the system, whether execution errors exist in the workflows based on the running.

14. The method of claim 10, further comprising:
providing, by the system via an algorithm management application, access to collective workflow information defining the workflows and management functions related to the workflows.

15. The method of claim 14, wherein the wherein the workflow management functions include an activation/deactivation function that provides for selectively activating and deactivating one or more of the workflows.

16. A non-transitory machine-readable storage medium, comprising executable instructions that, when executed by a processor associated with an algorithm orchestration system, facilitate performance of operations, comprising:

providing an algorithm catalog that comprises algorithm information identifying algorithms available for application to medical images and algorithm execution instructions for executing the algorithms in association with invoking the algorithms at respective network accessible systems where the algorithms are stored;

providing a workflow creation tool that facilitates creating workflows made available by the algorithm orchestration system for application to the medical images, the workflows respectively comprising workflow information defining a set of computer-executable processing steps to be applied to one or more of the medical images, wherein the workflow creation tool comprises a graphical user interface that facilitates creating the workflows using graphical nodes in association with receiving user input dragging and dropping the graphical nodes onto a workflow creation area of the graphical user interface, connecting the graphical nodes using one or more connection lines to define relationships between the graphical nodes, and configuring the graphical nodes, and wherein the graphical nodes comprise different types of graphical nodes respectively corresponding to different types of computer-executable processing steps available for processing the medical images, including a task node corresponding to an algorithm execution task, wherein based on selection of the task node, the workflow creation tool provides a selectable list of the algorithms included in the algorithm catalog and integrates a selected algorithm from the selectable list into the workflows in association with importing the algorithm execution instructions corresponding to the selected algorithm into the workflow information from the algorithm catalog, and wherein the different types of graphical nodes are selected from the group consisting of: the task node, a decision node, a sub-workflow node, a wait node, a fork node, a join node and a function node.

17. The non-transitory machine-readable storage medium of claim 16, the operations further comprising:

storing the workflows created using the workflow creation tool;

receiving image processing requests from medical imaging providers via a network;

controlling execution of the workflows on the medical images in association with reception of the image processing requests;

generating workflow results based on the execution, the workflow results comprising one or more of outputs of respective algorithms incorporated therein; and returning the workflow results to the medical imaging providers via the network.

18. The system of claim 2, wherein the workflow execution component retrieves the one or more medical images from one or more source storage systems and loads the one or more medical images into a local storage system based on reception of the image processing request and a determination that the workflow is applicable to the one or more medical images, and wherein the execution component controls the execution of the workflow on the one or more medical images in association with accessing the one or more medical images from the local storage system.

19. The system of claim 1, wherein the execution instructions control the application of the algorithms to the medical images as web-services.

20. The system of claim 1, wherein the execution instructions control the application of the algorithms to the medical images as Kubernetes jobs.

21. The system of claim 1, wherein the different types of graphical nodes further include other types of nodes corresponding to other types of the different types of the computer-executable steps available for processing the medical images, including at least one of, a medical image filtering step, a data retrieval step, a data moving step, or a data deletion step.

22. The system of claim 1, wherein the different types of graphical nodes are visually distinctive from one another.

23. The system of claim 1, wherein the different types of graphical nodes comprise different shapes or symbols.

24. The system of claim 1, wherein the different types of nodes respectively correspond to different computer-executable code.

* * * * *